(12) United States Patent
Kiesel et al.

(10) Patent No.: US 8,153,949 B2
(45) Date of Patent: Apr. 10, 2012

(54) OBTAINING SENSING RESULTS INDICATING TIME VARIATION

(75) Inventors: Peter Kiesel, Palo Alto, CA (US); Joerg Martini, San Francisco, CA (US); Michael Bassler, Erlangen (DE); Markus Beck, Palo Alto, CA (US); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 485 days.

(21) Appl. No.: 12/337,737

(22) Filed: Dec. 18, 2008

(65) Prior Publication Data

US 2010/0155577 A1    Jun. 24, 2010

(51) Int. Cl.
  *G01J 1/42* (2006.01)
  *F21V 9/16* (2006.01)
  *G01N 21/25* (2006.01)

(52) U.S. Cl. .......... 250/208.2; 250/459.1; 356/417

(58) Field of Classification Search .......... 250/231.1, 250/231.16, 223 B, 223 R, 288, 343, 364, 250/373, 564, 428, 432 R, 437, 432, 458.1, 250/208.1, 214 R, 231.18, 459.1, 208.2, 573; 341/8, 9, 13, 14, 133; 356/73, 318, 343, 356/410, 419, 417; 359/890, 238; 422/82.08, 422/82.05

See application file for complete search history.

(56) References Cited

U.S. PATENT DOCUMENTS

| | | | |
|---|---|---|---|
| 4,081,277 A | 3/1978 | Brault et al. | |
| 4,536,762 A * | 8/1985 | Moates | 340/870.02 |
| 4,764,670 A | 8/1988 | Pace et al. | |
| 5,151,585 A | 9/1992 | Siebert | |
| 5,254,919 A * | 10/1993 | Bridges et al. | 318/560 |
| 5,324,401 A | 6/1994 | Yeung et al. | |
| 5,370,842 A | 12/1994 | Miyazaki et al. | |
| 5,674,698 A | 10/1997 | Zarling et al. | |
| 5,682,038 A | 10/1997 | Hoffman | |
| 5,760,900 A | 6/1998 | Ito et al. | |

(Continued)

FOREIGN PATENT DOCUMENTS

WO    WO 95/20144 A1    7/1995

(Continued)

OTHER PUBLICATIONS

Office communication in U.S. Appl. No. 12/024,490, mailed Nov. 2, 2009, 14 pages.

(Continued)

*Primary Examiner* — Georgia Y Epps
*Assistant Examiner* — Don Williams
(74) *Attorney, Agent, or Firm* — Stanzione & Kim, LLP

(57) ABSTRACT

In response to objects having relative motion within an encoding/sensing region relative to an encoder/sensor that, e.g., photosenses emanating light or performs impedance-based sensing, sensing results can indicate sensed time-varying waveforms with information about the objects, about their relative motion, about excitation characteristics, about environmental characteristics, and so forth. An encoder/sensor can include, for example, a non-periodic arrangement of sensing elements; a longitudinal sequence of sensing elements with a combined sensing pattern that approximates a superposition or scaled superposition of simpler sensing patterns; and/or IC-implemented sensing elements that include photosensing arrays on ICs and readout/combine circuitry that reads out photosensed quantities from cells in groups in accordance with cell-group sensing patterns and combines the readout photosensed quantities to obtain the sensing results. Objects can move fluidically as in flow cytometry, through scanning movement as in document scanning, or in other ways.

26 Claims, 21 Drawing Sheets

U.S. PATENT DOCUMENTS

| | | | |
|---|---|---|---|
| 5,793,485 | A | 8/1998 | Gourley |
| 5,872,655 | A | 2/1999 | Seddon et al. |
| 5,880,474 | A | 3/1999 | Norton et al. |
| 5,945,676 | A | 8/1999 | Khalil et al. |
| 6,040,578 | A | 3/2000 | Malin et al. |
| 6,091,502 | A | 7/2000 | Weigl et al. |
| 6,429,022 | B1 | 8/2002 | Kunz et al. |
| 6,558,945 | B1 | 5/2003 | Kao |
| 6,580,507 | B2 | 6/2003 | Fry et al. |
| 6,628,390 | B1 | 9/2003 | Johnson |
| 6,747,285 | B2 | 6/2004 | Schueller et al. |
| 6,816,257 | B2 | 11/2004 | Goix |
| 6,839,140 | B1 | 1/2005 | O'Keefe et al. |
| 6,867,420 | B2 | 3/2005 | Mathies et al. |
| 6,906,792 | B2 | 6/2005 | Ortyn et al. |
| 7,034,933 | B2 | 4/2006 | Walker et al. |
| 7,195,797 | B2 | 3/2007 | Mearini et al. |
| 7,248,361 | B2 | 7/2007 | Kiesel et al. |
| 7,252,360 | B2 | 8/2007 | Hersch et al. |
| 7,268,868 | B2 | 9/2007 | Kiesel et al. |
| 7,274,011 | B2 | 9/2007 | Tennant et al. |
| 7,291,824 | B2 | 11/2007 | Kiesel et al. |
| 7,298,478 | B2 | 11/2007 | Gilbert et al. |
| 7,305,112 | B2 | 12/2007 | Curry et al. |
| 7,355,699 | B2 | 4/2008 | Gilbert et al. |
| 7,358,476 | B2 | 4/2008 | Kiesel et al. |
| 7,365,022 | B2 | 4/2008 | Wong et al. |
| 7,386,199 | B2 | 6/2008 | Schmidt et al. |
| 7,420,677 | B2 | 9/2008 | Schmidt et al. |
| 7,433,552 | B2 | 10/2008 | Kiesel et al. |
| 7,440,101 | B2 | 10/2008 | Auer et al. |
| 7,456,953 | B2 | 11/2008 | Schmidt et al. |
| 7,466,409 | B2 | 12/2008 | Scherer et al. |
| 7,471,399 | B2 | 12/2008 | Kiesel et al. |
| 7,479,625 | B2 | 1/2009 | Kiesel et al. |
| 7,502,123 | B2 | 3/2009 | Schmidt et al. |
| 7,522,786 | B2 | 4/2009 | Kiesel et al. |
| 7,547,904 | B2 | 6/2009 | Schmidt et al. |
| 7,554,673 | B2 | 6/2009 | Kiesel et al. |
| 7,701,580 | B2 | 4/2010 | Bassler et al. |
| 2002/0155485 | A1 | 10/2002 | Kao |
| 2003/0169311 | A1* | 9/2003 | Kong Leong et al. .......... 347/19 |
| 2003/0235924 | A1 | 12/2003 | Adams et al. |
| 2004/0027462 | A1 | 2/2004 | Hing |
| 2004/0038386 | A1 | 2/2004 | Zesch et al. |
| 2004/0067167 | A1 | 4/2004 | Zhang et al. |
| 2007/0046301 | A1 | 3/2007 | Kasapi |
| 2007/0076210 | A1 | 4/2007 | Kiesel et al. |
| 2007/0146704 | A1 | 6/2007 | Schmidt et al. |
| 2007/0166725 | A1* | 7/2007 | McBride et al. ................. 435/6 |
| 2008/0013092 | A1 | 1/2008 | Maltezos et al. |
| 2008/0181827 | A1 | 7/2008 | Bassler et al. |
| 2008/0183418 | A1 | 7/2008 | Bassler et al. |
| 2008/0186488 | A1 | 8/2008 | Kiesel et al. |
| 2008/0186492 | A1 | 8/2008 | Kiesel et al. |
| 2008/0186500 | A1 | 8/2008 | Schmidt et al. |
| 2008/0186503 | A1 | 8/2008 | Kiesel et al. |
| 2008/0186504 | A1 | 8/2008 | Kiesel et al. |
| 2008/0197272 | A1 | 8/2008 | Kiesel et al. |
| 2008/0299327 | A1 | 12/2008 | Salleo et al. |
| 2009/0190121 | A1 | 7/2009 | Hegyi et al. |
| 2009/0194705 | A1 | 8/2009 | Kiesel et al. |
| 2009/0195773 | A1 | 8/2009 | Bassler et al. |
| 2009/0195852 | A1 | 8/2009 | Bassler et al. |
| 2009/0220189 | A1 | 9/2009 | Kiesel et al. |

FOREIGN PATENT DOCUMENTS

| | | | |
|---|---|---|---|
| WO | WO 99/54730 | A1 | 10/1999 |
| WO | WO 00/62050 | A1 | 10/2000 |
| WO | WO 02/25269 | A2 | 3/2002 |

OTHER PUBLICATIONS

Office communication in U.S. Appl. No. 11/698,409, mailed Nov. 17, 2009, 18 pages.
Office communication in U.S. Appl. No. 12/025,394, mailed Jan. 22, 2010, 7 pages.
Office communication in U.S. Appl. No. 12/023,436, mailed Feb. 5, 2010, 16 pages.
Amendment in U.S. Appl. No. 12/023,436, submitted Mar. 23, 2010, 24 pages.
Office communication in U.S. Appl. No. 12/023,436, mailed Apr. 16, 2010, 8 pages.
Amendment in U.S. Appl. No. 12/025,394, submitted Apr. 22, 2010, 17 pages.
Amendment in U.S. Appl. No. 11/698,409, submitted May 17, 2010, 16 pages.
Shapiro, H. M., Practical Flow Cytometry, Fourth Edition, Wiley-Liss, 2003, Table of Contents and pp. 49-59, 124-183, 191-197, 345, and 364-366.
Hoffman, R. A., "Flow Cytometry: Instrumentation, Applications, Future Trends and Limitations", Springer Series on Fluorescence, vol. 6, 2008, pp. 307-342.
Office communication in U.S. Appl. No. 12/023,436, mailed Dec. 23, 2008, 15 pages.
Amendment in U.S. Appl. No. 12/023,436, submitted Mar. 23, 2009, 22 pages.
Office communication in U.S. Appl. No. 12/022,485, mailed Jan. 16, 2009, 18 pages.
Amendment in U.S. Appl. No. 12/022,485, submitted Apr. 15, 2009, 30 pages.
Office communication in U.S. Appl. No. 12/024,490, mailed Dec. 24, 2008, 12 pages.
Amendment in U.S. Appl. No. 12/024,490, submitted Mar. 24, 2009, 32 pages.
Bassler, et al., U.S. Appl. No. 12/025,394, Feb. 4, 2008, 61 pages.
Bracewell, R. N., The Fourier Transform and Its Applications, Second Edition, McGraw-Hill, 1978, Table of Contents and pp. 24-50, 98-126, and 177-188.
Office communication in U.S. Appl. No. 11/698,409, mailed Jun. 11, 2010, 21 pages.
Office communication in U.S. Appl. No. 12/022,485, mailed Jul. 31, 2009, 5 pages.
Response to Restriction Requirement in U.S. Appl. No. 12/022,485, submitted Aug. 27, 2009, 20 pages.
Office communication in U.S. Appl. No. 12/023,436, mailed Jun. 12, 2009, 20 pages.
Amendment in U.S. Appl. No. 12/023,436, submitted Sep. 3, 2009, 29 pages.
Office communication in U.S. Appl. No. 12/024,490, mailed Jul. 22, 2009, 16 pages.
Amendment After Final Rejection in U.S. Appl. No. 12/024,490, submitted Sep. 22, 2009, 28 pages.
Adams, M.L., Enzelberger, M., Quake, S., and Scherer, A., "Microfluidic integration on detector arrays for absorption and fluorescence micro-spectrometers," Sensors and Actuators, 2003, pp. 25-31.
Bassler, M., Schmidt, O., Kiesel, P., Johnson, N.M., "Class Identification of Bio-Molecules Based on Multi-Color Native Fluorescence Spectroscopy", International Journal of High Speed Electronics and Systems (IJHSES), vol. 17, Issue 4, 2007, pp. 671-680.
Cheung, K., Gawad, S., and Renaud, P., "Impedance Spectroscopy Flow Cytometry: On-Chiip Label-Free Cell Differentiation", Cytometry Part A, vol. 65A, 2005, pp. 124-132.
"Flow Cytometry", printed from www.wellscenter.iupui.edu/MMIA on Jan. 29, 2008, 4 pages.
"Lab-on-a-Chip, Advances in Microarray TEchnology and Advances in Biodefense Technology", brochure, May 7-8, 2008, 6 pages.

* cited by examiner

OBTAINING SENSING RESULTS INDICATING TIME VARIATION

The following applications, each of which is hereby incorporated by reference in its entirety, might be regarded as related to this application: "Sensing Photon Energies Emanating from Channels or Moving Objects", U.S. patent application Ser. No. 11/315,386, now published as U.S. Patent Application Publication No. 2007/0146704; "Method and System for Evaluation of Signals Received from Spatially Modulated Excitation and Emission to Accurately Determine Particle Positions and Distances", U.S. patent application Ser. No. 11/698,338, now published as U.S. Patent Application Publication No. 2008/0183418; "Method and System Implementing Spatially Modulated Excitation or Emission for Particle Characterization with Enhanced Sensitivity", U.S. patent application Ser. No. 11/698,409, now published as U.S. Patent Application Publication No. 2008/0181827; "Obtaining Information From Optical Cavity Output Light", U.S. patent application Ser. No. 11/702,249, now published as U.S. Patent Application Publication No. 2008/0186500; "Photosensing Optical Cavity Output Light", U.S. patent application Ser. No. 11/702,250, now published as U.S. Patent Application Publication No. 2008/0186503; "Distinguishing Objects", U.S. patent application Ser. No. 11/702,328, now published as U.S. Patent Application Publication No. 2008/0186488; "Encoding Optical Cavity Output Light", U.S. patent application Ser. No. 11/702,363, now published as U.S. Patent Application Publication No. 2008/0186492; "Moving Analytes and Photosensors", U.S. patent application Ser. No. 11/702,470, now published as U.S. Patent Application Publication No. 2008/0186504; "Surface Energy Control Methods for Color Filter Printing", U.S. patent application Ser. No. 11/755,717; "Producing Sandwich Waveguides", U.S. patent application Ser. No. 11/777,661; "Producing Fluidic Waveguides", U.S. patent application Ser. No. 11/777,712; "Obtaining Information from Time Variation of Sensing Results", U.S. patent application Ser. No. 12/022,485; "Providing Time Variation in Emanating Light", U.S. patent application Ser. No. 12/023,436; "Transmitting/Reflecting Emanating Light with Time Variation", U.S. patent application Ser. No. 12/024,490; "Producing Filters with Combined Transmission and/or Reflection Functions", U.S. patent application Ser. No. 12/025,394; "Sensing Photons From Objects in Channels", U.S. patent application Ser. No. 12/098,584, now published as U.S. Patent Application Publication No. 2008/0197272; "Obtaining Sensing Results and/or Data in Response to Object Detection", U.S. patent application Ser. No. 12/337,771 and "Causing Relative Motion", U.S. patent application Ser. No. 12/337,796.

BACKGROUND OF THE INVENTION

The present invention relates generally to techniques that obtain sensing results indicating time variation; for example, such sensing results can be obtained in response to objects that have relative motion, such as objects that move relative to a sensing component and/or an encoding component. More specifically, techniques can respond to objects that have relative motion, providing sensing results that indicate time-varying waveforms that are non-periodic or that have time variation in accordance with one or more sensing patterns.

Various techniques have been proposed for sensing moving objects. For example, U.S. Pat. No. 7,358,476 describes a fluidic structure with a channel along which is a series of sensing components to obtain information about objects traveling within the channel, such as droplets or other objects carried by fluid. A sensing component includes a set of cells that photosense a range of photon energies that emanate from objects; in a pair of cells that includes a reference cell and a subrange cell, one cell can have a different sensing area or a different coating than the other to obtain signal strengths of the same order. A processor can receive information about objects from the sensing components and use it to obtain spectral information. Similar techniques are described, for example, in U.S. Pat. Nos. 7,291,824, 7,386,199, and 7,420,677 and in U.S. Patent Application Publication Nos. 2007/0146704 and 2008/0197272.

It would be advantageous to have improved techniques for obtaining time-varying sensing results, such as in response to moving objects.

SUMMARY OF THE INVENTION

The invention provides various exemplary embodiments, including articles, methods, systems, and apparatus. In general, the embodiments involve obtaining sensing results that indicate time-varying waveforms in response to objects that have relative motion.

These and other features and advantages of exemplary embodiments of the invention are described below with reference to the accompanying drawings.

DETAILED DESCRIPTION

Figure 1:
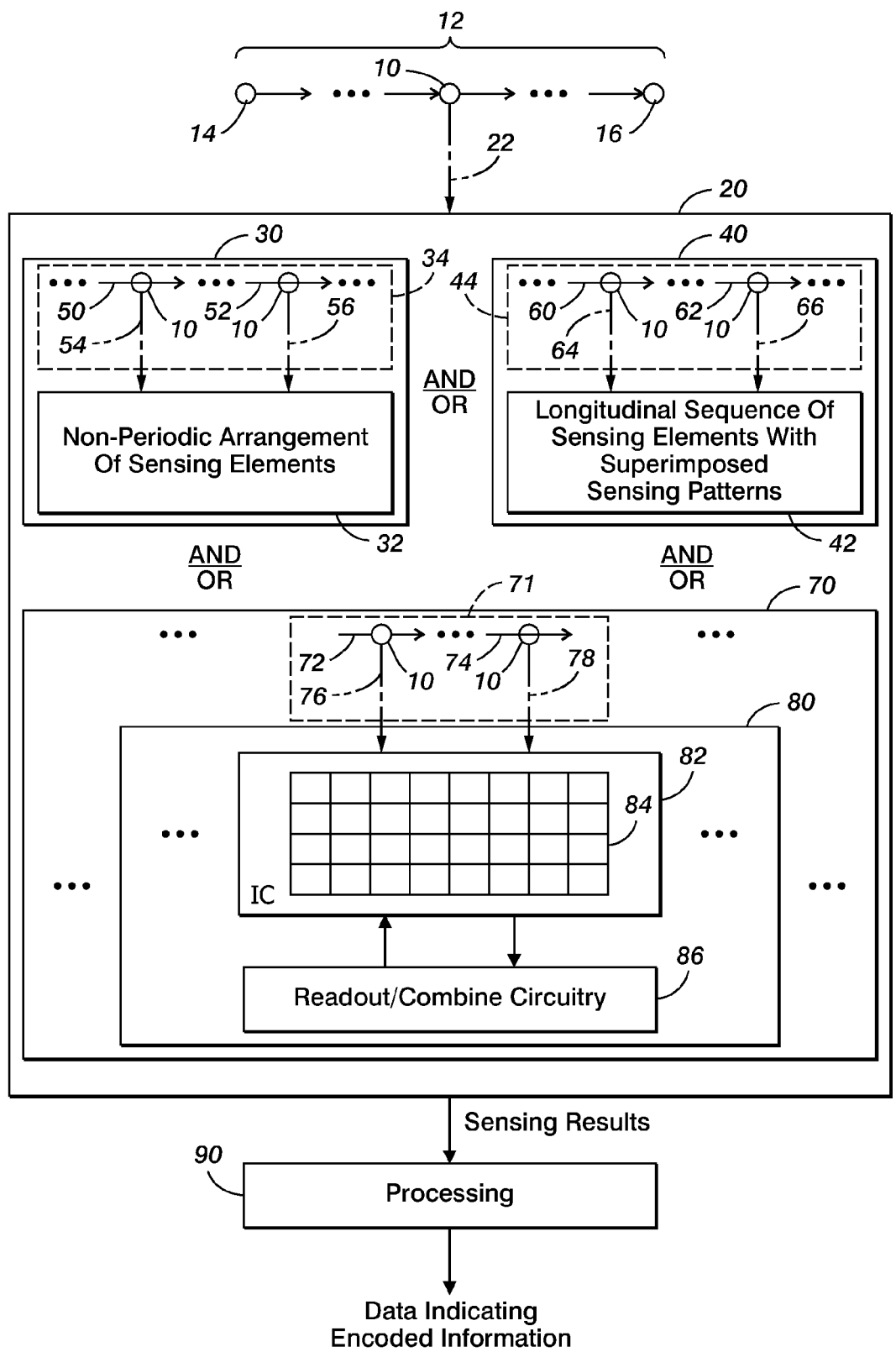
FIG. 1 is a schematic diagram showing features of techniques that, in response to objects that have relative motion, obtain sensing results that indicate time-varying waveforms.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. Light that can include information is sometimes referred to herein as an "optical signal".

The term "sensing" is used herein in the most generic sense of obtaining information from a physical stimulus; sensing therefore includes actions such as detecting, measuring, and so forth. A "sensor" is a device that performs sensing. Data or other signals that indicate or include results of sensing are sometimes referred to herein as "sensing results". An operation "obtains" sensing results if the operation makes the sensing results available in any appropriate way in the context; for example, an operation could obtain sensing results by producing sensing results, by providing or transferring sensing results from one position or time to another, by accessing sensing results that are stored in computer memory or on a storage medium or captured in any other machine-accessible form, or in any other way appropriate to the context.

"Photosensing" is sensing of light. A "photosensor" is accordingly an electronic device that performs photosensing. More specifically, if optical signals include information, a photosensor that receives the optical signals may be able to sense the information and provide sensing results that indicate or include the information; sensing results from a photosensor often indicate "photosensed quantities", meaning quantities that indicate a characteristic of photosensed light, such as an intensity, a spectral characteristic, etc. A surface at which photosensing occurs is referred to herein as a "photosensitive surface".

Another type of sensing relevant to some exemplary implementations described below is "impedance-based sensing", meaning sensing that obtains information from variation in resistance (or inversely, conductivity), capacitance, inductance, or another form of electrical impedance that varies in response to a physical stimulus such as an electrical or magnetic characteristic of an object or of an object's environment. As used herein, "impedance-based sensing" includes sensing with Hall effect sensors and similar types of sensors.

Photosensors, impedance-based sensors, and other types of sensors can be combined and configured in many different ways, and all such combinations and configurations of one or more sensors are encompassed herein by the general term "sensing arrangement". A sensing arrangement can include, for example, one or more "sensing elements", in which case it may be referred to as a "sensing element arrangement"; while the term "sensing component" is generic, referring to any component that performs sensing (including, for example, a component that includes a sensor together with at least some related circuitry), the terms "sensing element arrangement" and "sensing element" are related and therefore a bit more specific, in that a sensing element arrangement is a sensing component that includes one or more sensing elements, while a sensing element is a sensor that generally does not include other sensing elements within it. The more abstract term "sensing pattern" is used herein to refer to a pattern that a sensing element arrangement could have in one or more dimensions of space and/or time; in general, a number of differently implemented sensing element arrangements could have the same or approximately the same sensing pattern. As used herein, the terms "IC-implemented sensing element" or "IC-implemented sensing arrangement" refer to sensing elements or arrangements that include one or more integrated circuits (ICs) with circuitry that performs sensing; for example, an IC-implemented sensing element or arrangement could include an IC that includes an array of photosensing cells.

In general, the various types of sensors described herein provide sensing results in the form of electrical signals unless otherwise indicated or required by the context. The term "electrical signal" is used herein to encompass any signal that transfers information from one position or region to another in an electrical, electronic, electromagnetic, or magnetic form. Electrical signals may be conducted from one position or region to another by electrical or magnetic conductors, but the broad scope of electrical signals also includes light and other electromagnetic forms of signals and other signals transferred through non-conductive regions due to electrical, electronic, electromagnetic, or magnetic effects. In general, the broad category of electrical signals includes both "analog" and "digital" signals: An "analog" electrical signal includes information in the form of a continuously variable physical quantity, such as voltage; a "digital" electrical signal, in contrast, includes information in the form of discrete values of a physical characteristic, which could also be, for example, voltage.

In a system in which encoding and/or sensing are performed, an object moves relative to a region or component or feature of the system or "has relative motion" if the object has a succession of positions over time with respect to the region, component, or feature; the succession of positions is sometimes referred to herein as the object's "path", even though the object may not itself be moving in an absolute sense but only relative to the region, component, or feature. More generally, the term "path" is used herein in the general sense of a series of positions and/or configurations that a relatively moving and/or varying object can have during its relative motion and/or variation. For generality, a part of an object's relative motion, such as a part of a path, is sometimes referred to herein as a "segment", which could encompass any continuous series of one or more positions and/or configurations within the relative motion.

In this context, the term "region" refers to a connected set of points or positions in space. In several exemplary implementations described below, an encoding/sensing region is a region that is "relative to" a component or device, meaning that the region has an approximately constant spatial relationship to the component or device and accordingly would move with the component or device if the component or device moved. An encoding/sensing region may be thought of as the region relative to an encoder/sensor within which an object can interact with the encoder/sensor such that information can be encoded and sensed through the interaction to an appropriate level of accuracy for a given application.

The various exemplary implementations described below address problems that arise in obtaining sensing results that indicate time variation in response to objects that have relative motion; the objects could, for example, be biological cells, molecules, submolecular complexes, and other such objects, as in flow cytometry, or other types of objects as in other applications. Many sensing techniques provide sensing results in response to moving objects, but available techniques have limitations.

Flow cytometry has become an indispensable tool in clinical diagnostics, such as in diagnosing cancer, AIDS, and infectious diseases during outbreaks, and also in microbiology and other areas. The cost and size of existing cytometers preclude their use in field clinics, water monitoring, agriculture/veterinary diagnostics, and rapidly deployable biothreat detection.

A number of commercially available flow cytometers use multiple excitation sources, each focused on a well-defined location or region separate from the others. Light emitted from each source's region is typically analyzed with a series of beam splitters, filters, and photomultiplier tubes (PMTs) in order to detect and distinguish differently stained cells or cells that concurrently carry multiple dyes. Cells are typically stained in solution with different dyes prior to insertion into a cytometer, and the measurement takes place in a fluidic channel in which cells traverse a detection region, typically at a speed of up to several meters per second. In the detection region, focused laser light (typically with an elliptical focus of 80 μm×40 μm) excites the dyes on the cells. The resulting fluorescent light can be collected by a microscope lens, sorted by band pass filters, and detected by PMTs or avalanche photodiodes (APDs). For each spot excitation, a respective set of filters and detectors is needed, which is costly and leads to bulky devices with strict requirements necessary to maintain optical alignment. Since the detection region is small and objects traverse it rapidly (typical dwell times are around 10 μsec), such flow cytometers have serious signal-to-noise (S/N) ratio issues for weakly fluorescing cells. These issues become more acute if multiple targets must be characterized and distinguished in some way, such as by counting.

A major cost in flow cytometry applied in clinical diagnostics is cost of reagents (e.g. antibodies and conjugated dyes). There are two ways to reduce the amount of consumables: First, one can reduce the required amount of analyte, e.g. by employing microfluidic techniques; and second, one can reduce the amount of consumable per analyte volume. Reducing amounts used would, however, reduce fluorescent intensity. It would be valuable to be able to overcome this constraint with a cost-effective and reliable technique to detect and distinguish weakly emitting cells.

Previous proposals to address these problems have involved spatially modulated single-color excitation to improve S/N ratios and to shift the detection limit toward weaker emitting cells. Spatial resolution can be maintained or improved in comparison with previous flow cytometry techniques, because fluorescing light is spatially modulated over a comparably large detection region; this is helpful because spatial resolution affects maximum detection or count rate of a device. But single-color techniques are limited, whether excitation is performed in a black/white approach or with a single-color interference pattern from a light source. Also, single-color techniques can encounter problems with wavelength sensitivity and bleaching of dyes. Because of low wavelength sensitivity, many flow cytometers with filter-PMT combinations are also constrained to use dyes with substantially different fluorescence wavelengths.

In addressing such problems, exemplary implementations described below obtain sensing results that indicate time-varying waveforms in response to objects that have relative motion. For example, exemplary implementations obtain such sensing results in one or more of three ways: A first way is to obtain sensing results that indicate a non-periodic time-varying waveform, as would be indicated by sensing results from a non-periodic arrangement of sensing elements; a second way is to obtain sensing results that indicate a superposition time-varying waveform, as would be indicated by sensing results from a longitudinal sequence of sensing elements with a combined sensing pattern that is approximately equal to a superposition or scaled superposition of a set of simpler sensing patterns; and a third way is to read out and combine photosensed quantities from photosensing cells in groups in accordance with cell-group sensing patterns, obtaining sensing results that indicate time-varying waveforms in accordance with the sensing patterns.

Such techniques, by themselves or in combination with other techniques, make it possible to provide a robust variety of sensing results indicating time-varying waveforms, permitting many possibilities that would otherwise be difficult to achieve. The resulting sensing results can then be subjected to any of a wide variety of information extraction techniques to obtain information of various kinds. In addition, some of these techniques can be implemented to maintain higher spatial resolution, possibly making spectral characterization of particles feasible.

The term "photon" refers herein to a quantum of light, and the term "photon energy" refers herein to the energy of a photon. Light can be described as having a "photon energy distribution" or, more commonly, a "spectrum", meaning the combination of photon energies that are included in the light; highly monochromatic light, for example, has a photon energy distribution or spectrum with one peak energy value.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where the speed of light in a medium M is a constant $c_M$ less than c, then M has an index of refraction $n_M = c/c_M$.

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry, and a given hardware component can similarly be replaced by equivalent processor operations controlled by software.

Circuitry can be described based on its operation or other characteristics. For example, circuitry that performs control operations is sometimes referred to herein as "control circuitry" and circuitry that performs processing operations is sometimes referred to herein as "processing circuitry". Also, "readout circuitry" refers herein to circuitry that operates to read out photosensed quantities, while "readout/combine circuitry" refers herein to circuitry operates as readout circuitry and also operates to combine readout quantities. As used herein, an operation "combines" quantities in any way that includes the quantities in a single item of data, a single data structure, or a single combination of items of data or data structures that can be accessed together, such as in sequence; for example, two quantities can be combined by arithmetic operations such as addition, subtraction, multiplication, division, averaging, and so forth, or by concatenating them, linking them, or otherwise ordering them into a sequence or data structure.

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

In general, sensors, processors, and other such items may be included in a system in which they are operated automatically or partially automatically. As used herein, the term "system" refers to a combination of two or more parts or components that can perform an operation together. A system may be characterized by its operation.

Within a system, device, or other article, components and parts may be referred to in a similar manner, such as a "sensing component", as described above, or an "encoding component" that operates to encode information. More specifically, a sensing or encoding component could be an "encoding/sensing component", in some cases referred to as an "encoding/sensing arrangement" or simply an "encoder/sensor", in each case meaning that the component, arrangement, or encoder/sensor operates both to encode and sense information, providing sensing results that indicate the encoded information. Also, a "relative motion component" operates to cause some sort of relative motion; a "processing component" performs processing operations; and various other components are described below. In addition, a component or part may be identified by characteristics other than its operation.

In FIG. 1, object 10 is one of series 12 of objects 14 through 16 that have relative motion with respect to component 20, which could be described as a sensing component, an encoding component, or an encoding/sensing component, depending on context. Each of the objects in series 10 could be described as having a respective path.

As object 10 moves relative to component 20, it interacts with one or more sensing elements in component 20, as indicated by arrow 22. For example, light could emanate from object 10, such as by emission, scattering (including, e.g. reflection), or transmission, and a portion of the emanating light could be received by photosensors in component 20. In general, such emanating light includes light within an application's range of photon energies, meaning that techniques as in FIG. 1 can be successfully used in a given application, e.g. flow cytometry, bio-chip readout, or any suitable kind of analyte detection, even though emanating light might also include photon energies that are outside the application's range and that might not interact with photosensors in component 20 in the same way as light in the application's range. In another example, object 10 could interact electrically or magnetically with impedance-based sensing elements in component 20. In general, a sensor of any kind obtains sensing results "from" objects in a sensing region when the sensing results include information resulting from any such interaction between the sensor and the objects while the objects are in the sensing region.

The term "object" is used herein in the general sense of any distinguishable thing about which information can be obtained by a sensor and included in its sensing results. In some implementations, sensors can obtain information about objects by receiving signals from them; for example, signals in the form of light can emanate from an object, whether through emission (e.g. radiation, fluorescence, incandescence, chemoluminescence, bioluminescence, cathodoluminescence, other forms of luminescence, etc.), elastic or inelastic scattering (e.g. reflection, deflection, diffraction, refraction, etc.), or transmission, and can be sensed by a photosensor. The light "emanates from" or is simply "from" the object, and may be referred to herein as "emanating light". An object from which light is emanating may be referred to herein as a "light-emanating object". In other implementations, sensors can obtain information about objects in other ways, some of which are mentioned herein; in particular, impedance-based sensors can obtain information about objects in various ways, resulting from, for example, interactions between objects and an arrangement of electrodes or an arrangement of Hall effect sensors.

Examples of objects that could occur in implementations as described below include droplets, small volumes of fluid, single molecules, agglomerated molecules, molecule clusters, cells, viruses, bacteria, lengthy polymers such as DNA or protein chains, submolecular complexes such as tags on DNA or protein chains, microparticles, nanoparticles, beads or other small particles that can bind and carry specific chemicals or other analytes, emulsions, any such type of object in an array such as an array of sample wells, and a distinguishable region of a surface such as a small area of a sheet of paper or other image-bearing medium; a distinguishable region, could, for example, be a colored spot. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet or other object can act as a fluorescent, absorbent, or scattering component. Analyte that is otherwise homogeneously distributed, for example, can be localized by binding to carrier beads, resulting in a moving object that emanates light or provides other signals in a way that depends on the analyte.

With respect to a light-emanating object, the expressions "characteristic of an object" and "emanating light including information" have related meanings: The term "characteristic" refers to a trait, quality, or property of an object that can be measured and that persists with a given value or within a given range or other subset of possible values while light that "includes information about the characteristic" is emanating from the object. In appropriate implementations, characteristics of an object could include mass, volume, density, cross-section or other shape, chemical composition, position, speed, acceleration, direction of movement, spin axis, directional or angular velocity or momentum, net charge, charge polarity, absorption spectrum, emission spectrum, scattering spectrum, and so forth. Therefore, emanating light "includes" information about a characteristic of an object if information included in the emanating light indicates a value, range, or other measure of the characteristic. Similar terminology can apply to types of interactions other than emanating light, such as interactions with impedance-based sensors.

Emanating light or signals resulting from other types of interactions can "include information" in many ways, some of which are described below in relation to specific implementations. Various criteria could be used to determine whether emanating light or a signal resulting from another type of interaction includes specified information, and such criteria can be referred to as "encoding criteria". Some encoding criteria, for example, involve comparison of magnitude of a signal with noise magnitude, e.g. signal-to-noise (S/N) ratios, because S/N ratio can affect whether specified information can be recovered from sensing results obtained by photosensing emanating light. Other types of encoding criteria could be used as appropriate. Where emanating light or a signal resulting from another type of interaction satisfies an appropriate encoding criterion for specified information, the light or signal may be said to "encode" the information.

Similarly, sensing results, whether from photosensing emanating light, from impedance-based sensing (e.g. with electrodes or Hall effect sensors), or from another type of sensing, can "include information" in many ways, and similar encoding criteria could be applied as with signals. Where sensing results indicate one or more time-varying waveforms, the sensing results can be referred to as having "encoded time variation" or as "indicating time variation".

The term "waveform" is used herein in the general sense of any set of values that varies over one or more dimensions, whether continuous or discrete, whether analog or digital, and whether measured or obtained in any other way; a "time-varying waveform" is a waveform that varies over a time dimension. Some of the time-varying waveforms described below in relation to exemplary implementations include intensity values, but the expression "time-varying waveforms" also encompasses other values that vary over time, including purely numerical values with no specified units or other physical significance. A "sensed time-varying waveform" is a time-varying waveform that is indicated by sensing results obtained over time. For example, if a photosensor provides sensed quantities that indicate intensity of received light, its sensing results could indicate a time-varying waveform indicating intensity sensed over time.

A moving object's path is treated herein as providing a directional orientation as follows: A direction parallel or approximately parallel to the path is sometimes referred to as a "longitudinal" or "lengthwise" direction, while a direction perpendicular or approximately perpendicular to the path is sometimes referred to as a "radial", "lateral", or "transverse" direction. The lengthwise direction in which the object is moving is sometimes referred to as "forward" or "downstream", while the opposite direction is sometimes referred to as "backward" or "upstream". A radial direction away from the path is "out" or "outward", while a radial direction toward the path is "in" or "inward". Light propagating toward the path may be referred to as "incoming" or "incident", while light propagating away from the path may be referred to as "outgoing". A component or arrangement of components is "along" the path if it is disposed near the path and has some extent in a longitudinal direction. A component or arrangement of components is "around" the path if, in a plane transverse to the path, it intersects multiple radial directions, at least two of which are separated by approximately 180 degrees of arc. A direction that similarly goes around the path is sometimes referred to herein as a "rotation" direction. In general, it should be understood that the above directional orientation is arbitrary and only for ease of description, and that a moving object's path may have any appropriate orientation.

Emanating light that includes information about an object's relative motion is sometimes referred to herein as "motion-affected" light, as including "motion-dependent information", or as having "motion-dependent encoding". For example, an object could have relative motion by being conveyed in fluid, such as liquid, gas, or aerosol, along a path in which it emanates light that is transmitted and/or reflected by a filter arrangement to include information about the object's motion, thus becoming motion-affected light; in such a case the object may be referred to as being "carried" by fluid. In another example, an object contained in or otherwise supported by a support structure could have relative motion due to relative scanning movement between the support structure and a filter component or another component such as a photosensor, and it could emanate light that is transmitted and/or reflected so that it becomes motion-affected light.

Similarly, sensing results or signals that include information about an object's relative motion are sometimes referred to herein as "motion-affected", as including "motion-dependent information", or as having "motion-dependent encoding". If the motion-dependent information depends on a moving object's speed, it may be referred to more specifically as "speed-dependent information"; where an object is carried by fluid, for example, sensing results or signals could include speed-dependent information indicating the object's speed as it is carried by fluid. In another example, an object contained in or otherwise supported by a support structure could have relative motion due to relative scanning movement between the support structure and an encoding and/or sensing component, and sensing results or signals could include speed-dependent information indicating speed of the object relative to the encoding and/or sensing component.

More generally, sensing results are obtained "from" or "in response to" a stimulus such as an object or an object's relative motion if the sensing results result from the stimulus and the sensing results include information about the stimulus, e.g. about one or more characteristics of the object or about the object's relative motion. For example, sensing results can "indicate time-varying waveforms in response to" objects, relative motion of objects, or another stimulus if the sensing results are obtained in response to the stimulus and indicate time-varying waveforms that include information about the stimulus; more specifically, sensing results can indicate time-varying waveforms that "depend on" an object's relative motion within an encoding/sensing region, meaning that the waveforms include encoded information resulting from the object's relative motion within the encoding/sensing region. An encoder/sensor can obtain sensing results in response to an object and/or an object's relative motion in many different ways.

Sensing elements of various kinds could be included in encoding/sensing components, sensing components, sensing arrangements, and/or other combinations and configurations of sensors, in a wide variety of ways. Within a given configuration of sensors, relationships between sensors can be described in a number of ways. A "longitudinal sequence" of sensing elements, for example, is a sequence that extends in a longitudinal direction as defined above; for example, interactions occurring in each of a sequence of segments of an object's path could be sensed by a respective sensing element in a longitudinal sequence. In other configurations, sensing elements may be "parallel", meaning that the sensing elements are not entirely in a longitudinal sequence, so that interactions occurring in at least one segment of an object's path could be sensed concurrently by more than one or all of the parallel sensing elements or alternatively by different subcombinations of the parallel sensing elements.

Several other categories of sensing arrangements and/or sensing patterns are described below in relation to exemplary implementations, including periodic and non-periodic sensing patterns, chirp patterns, random patterns, and so forth, and various other categories could be identified. As used herein, the term "random" refers to a pattern that is non-periodic over the entire length of a longitudinal sequence of sensing elements; in contrast, a "periodic" sensing arrangement has at least one pattern that repeats more than once across the arrangement's longitudinal length; and "chirp" patterns meet the above definition of random but can, with linearly varying time scaling, meet the above definition of periodic, in effect being a sequence of periods of linearly changing frequency or wavelength. A "cell-group sensing pattern" is a sensing pattern obtained by reading out photosensing cells in one or more arrays in groups in accordance with the cell-group sensing pattern, and cell-group sensing patterns can also be non-periodic arrangements, longitudinal sequences, periodic patterns, non-periodic patterns, chirp patterns, random patterns, and so forth. Any of these types of sensing arrangements and/or sensing patterns can be used to obtain "spatially modulated" emanating light or other interactions, meaning interactions that vary in time depending on position of an object involved in the interactions.

Implementations of ICs and photosensing components described herein include features characterized as "cells" (or "elements") and "arrays", terms that are used with related meanings: An "array" is an arrangement of "cells" or "elements"; unless otherwise indicated by the context, such as for a biological cell, the words "cell" and "element" are used interchangeably herein to mean a cell or an element of an array. An IC includes a "photosensor array" if the IC includes an array of cells, and at least some of the cells include respective photosensors.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

As used herein, the term "white", in a given implementation, refers to light with a spectrum that approximates maximum intensities across the implementation's full range of photon energies (which could be broad band, a combination of red, green, and blue, or another appropriate combination); the term "black" refers to the opposite of white, i.e. minimum available intensities across the full range, with the ideal being no light and therefore zero intensities. In emanating spectra, for example, light without maximal intensities across the full range as in white may be characterized as having a "gray level", such as one of the gray levels between white and black, or as having a "color", such as if it includes predominantly photon energies in a subrange, e.g. one of the colors in the visible range of wavelengths or in the infrared or ultraviolet ranges, or possibly a combination of such colors.

As illustrated by exemplary implementations described below, sensing patterns can vary in color sensing in one or more dimensions, in which case they may be referred to as "spectrally-dependent sensing patterns." Similarly, sensing patterns can vary in sensitivity to light intensity in one or more dimensions, in which case they may be referred to as "intensity-dependent sensing patterns." As with certain other features of sensing patterns, these are not incompatible, and a sensing pattern could be both spectrally-dependent and intensity-dependent. Within a spectrally-dependent sensing pattern, a photosensing element could photosense emanating light in a respective subrange of the range of emanating light, and subranges of photosensing elements could be "different", meaning that they are spectrally different by having not having identical sensing bands or in any other way. Within an intensity-dependent sensing pattern, a photosensing element could have a ratio between photosensed quantity and emanating light intensity, a "sensed intensity ratio" that is analogous to measures of photosensing efficiency such as "quantum efficiency", sometimes defined as the percentage of photons hitting a photoreactive surface that will produce an electron-hole pair.

Component 20 includes one or more of three specified combinations or configurations of sensors: Component 30 includes arrangement 32 that includes, or responds to objects in encoding/sensing region 34 by obtaining sensing results approximating, a non-periodic arrangement of sensing elements; component 40 includes arrangement 42 that includes, or responds to objects in encoding/sensing region 34 by obtaining sensing results approximating, a longitudinal sequence of sensing elements that has a combined sensing pattern that is approximately equal to a superposition or scaled superposition of two or more simpler sensing patterns; and sensing component 70 includes one or more IC-implemented sensing elements, each with one or more arrays that include photosensing cells and with readout/combine circuitry that reads out photosensed quantities from a set of the photosensing cells in groups in accordance with one or more cell-group sensing patterns and combines the readout photosensed quantities to produce sensing results. In each case, sensing results are obtained that indicate one or more time-varying waveforms, such as a non-periodic time-varying waveform, a superposition time-varying waveform, and/or one or more time-varying waveforms with time variation in accordance with cell-group sensing patterns. As a result of the sensing patterns, information can be encoded in time variation of interactions between objects such as object 10 and sensing elements in component 20.

Sensing elements and sensing patterns that include them or are approximated by reading them out can, of course, be different from each other in various ways. For example, sensing elements or parts of sensing patterns can differ in "extent", meaning that the elements or pattern parts extend over different distances, such as in a longitudinal direction. Photosensing elements can also differ in "color", meaning that they have different sensing bands or sensing spectra that are otherwise different in some way, either due to their own structure or due to coatings or other filters on or over them; also, photosensing spectra that have the same or approximately the same shape across a relevant range can differ in "intensity", meaning that they have different sensed intensity ratios. Also, simpler sensing patterns that are superimposed to provide a combined sensing pattern can have different sensing spectra or other differences; in FIG. 1, two simpler sensing patterns superimposed to provide the combined sensing pattern of arrangement 42 could, for example, be different from each other.

The term "optical filter" or simply "filter" refers herein to a light-transmissive or light-reflective part or component that transmits and/or reflects light in accordance with a respective criterion, sometimes referred to herein as a filter's "type". For example, one general category of filters is "band pass filters", referring to types of filters that, across some application's range of photon energies, e.g. a range of wavelengths or frequencies such as the visible range, preferentially transmit and/or reflect light within a subrange, sometimes referred to as a "band"; a band pass filter's type can therefore be specified by specifying the band or subrange of photon energies in which it transmits and/or reflects. A "blocking filter", which does not transmit or reflect any light in an application's range, can be viewed as a band pass filter with a band of zero bandwidth, while a "transparent filter", which transmits and/or reflects all light in an application's range, can be viewed as a band pass filter with a band that includes the entire range.

Filters can be combined and configured in many different ways, and all such combinations and configurations of one or more filters are encompassed herein by the general term "filter arrangement". In addition to filter arrangements described herein, other examples of filter arrangements are described in co-pending U.S. patent application Ser. No. 12/024,490, entitled "Transmitting/Reflecting Emanating Light with Time Variation", incorporated herein by reference in its entirety. More generally, however, the terms "sensing arrangement" and "sensing pattern" can encompass arrangements and patterns of photosensors together with filters structured and/or positioned to provide differences in color and/or intensity of photosensors within the arrangements and patterns.

Different sensing elements and sensing patterns can also be combined in a number of ways. For example, in a longitudinal sequence of photosensing elements, their sensing spectra are similarly combined into a sequence. On the other hand, sensing patterns can be "superimposed", meaning that both or all sensing patterns affect sensing results concurrently. As used herein, a sensing pattern is "simpler" than a combined sensing pattern in which it is superimposed with at least one other sensing pattern, except in cases where the combined sensing pattern and all of the superimposed sensing patterns have the same spectral shape or where the superimposed sensing patterns have related shapes that result in uniform loss of detail when superimposed in specific phase relationships; although there are many abstract examples of superpositions that result in uniform loss of detail (e.g. two square waves of the same period and at opposite phase would have a flat line superposition) simplifying superpositions are very unlikely to occur between sensing patterns with disparate shapes, such as random and periodic, random and chirped, chirped and periodic, and so forth—some detail might be lost locally in such cases, but most detail is preserved. Simpler sensing patterns can be superimposed to obtain a combined sensing patterns in various ways; for example, the direction in which the sensing patterns vary, sometimes referred to herein as "variation directions", can all be approximately aligned so that they are at least approximately parallel, and the patterns can then be superimposed.

As shown within component 30, as object 10 has relative motion through each a series of segments of its path including segment 50 and segment 52, respective interactions occur with sensing elements in arrangement 32, as indicated by arrows 54 and 56. Because of the non-periodic arrangement of sensing elements, these interactions encode information in time variation of sensing results, producing sensing results that indicate a non-periodic time-varying waveform.

Similarly, as shown within component 40, as object 10 has relative motion through each of a series of segments that includes segments 60 and 62, respective interactions occur with sensing elements in arrangement 42, as indicated by arrows 64 and 66. Because of the longitudinal sequence of sensing elements with a combined sensing pattern that is a superposition or approximate superposition of a set of simpler sensing patterns, these interactions also encode information in time variation of sensing results, so that the sensing results indicate a superposition time-varying waveform with time variation in accordance with all of the simpler sensing patterns in the set.

In some exemplary implementations below, for example, a sensing arrangement combines a periodic or chirp sensing pattern that can encode information about an object's position, speed, or other displacement rate with a random sensing pattern that can encode information about an object's spectrum or type. Sensing results are concurrently encoded with both types of information.

Also similarly, as shown within encoding sensing region 71 relative to array 84, as object 10 has relative motion through each of a series of segments that includes segments 72 and 74, respective interactions occur with one or more sensing elements, illustratively through emanating light represented by arrows 76 and 78. The sensing elements include element 80, which has one or more arrays that include photosensing cells, with each array being on a respective IC, with IC 82 with array 84 including photosensing cells being illustratively shown. Sensing element 80 also includes readout/combine circuitry 86, which reads out photosensed quantities from a set of the photosensing cells in element 80 in groups in accordance with one or more cell-group sensing patterns; circuitry 86 also combines the readout photosensed quantities to produce sensing results that indicate one or more time-varying waveforms with time variation in accordance with the cell-group sensing patterns. Implementations of component 70 can be useful, for example, in approximating various sensing patterns that include discrete photosensors, but without the expense and difficulty of fabricating or configuring discrete photosensors in accordance with each pattern.

As suggested by the words "AND/OR" between components 30, 40, and 70, the three are not mutually exclusive, and could be implemented together in any suitable combination of two or in a combination of all three. As described below in relation to some exemplary implementations, a single sensing arrangement could encode information in sensing results in all three of the ways illustrated for components 30, 40, and 70.

In general, sensing results take the form of analog or digital electrical signals, depending on the structure and circuitry included in component 20, but could be converted to other forms, such as optical or other electromagnetic signals, such as for subsequent storage, transmission, and processing. The operation in box 90 uses the sensing results from component 20 to obtain data indicating some or all of the encoded information, and can therefore be referred to as a "decoding" operation. For example, the operation in box 90 can use sensing results from component 20 to obtain information about object 10, and could be performed after any appropriate transmission, storage, conversion, or other operations on the sensing results, provided the operations preserve encoded information from component 20, e.g. by indicating one or more sensed time-varying waveforms. Exemplary operations in box 90 can include waveform comparison, e.g. between sensed time-varying waveforms or between a sensed time-varying waveform and a reference waveform, and/or a transforming operation or other operation that obtains a periodicity value such as a frequency or wavelength, using techniques as described, for example, in co-pending U.S. patent application Ser. No. 12/022,485, entitled "Obtaining Information from Time Variation of Sensing Results", incorporated herein by reference in its entirety.

Decoded information, as obtained in box 90, can be used in a wide variety of ways for a wide variety of purposes. In exemplary implementations described below, such information can be information about the objects and can, for example, be used to distinguish objects. In some applications, such as where the distinguished objects are registration marks in documents or other images, appropriate subsequent operations can be controlled based on the results of distinguishing objects. In other exemplary implementations, such information can be information about one or more features of excitation or environment, such as a characteristic of illumination or of fluid that carries the objects, and the information can, for example, be used to monitor the fluid's composition or other characteristics, possibly including characteristics that reflect environmental stimuli. Accordingly, the terms "characteristics of excitation" and "excitation characteristics" are used herein to refer to characteristics of one or more excitations received by objects that have relative motion within an encoding/sensing region, such as characteristics of illumination or other excitation; similarly, the terms "characteristics of environment" and "environmental characteristics" are used herein to refer to characteristics of one or more environmental stimuli that affect objects that have relative motion within an encoding/sensing region, such as characteristics of fluid that carries the objects.

Sensing component 20 in FIG. 1 could be implemented in many different ways, some of which are described below. In some exemplary implementations below, for example, a sensing component includes one or more discrete photosensors with different extent and, in some cases, with different sensing spectra, different sensed intensity ratios, or different filter arrangements through which emanating light passes; in yet others, photosensing is performed by photosensing cells in arrays on one or more ICs. In yet others, a sensing component includes impedance-based sensing elements, such as electrodes, Hall effect sensors, inductors, or other components in an appropriate sensing pattern. These techniques can be implemented together. As a result of these techniques, sensing results will have time variation that can encode information about objects or about features of excitation or of the environment.

Figure 2:
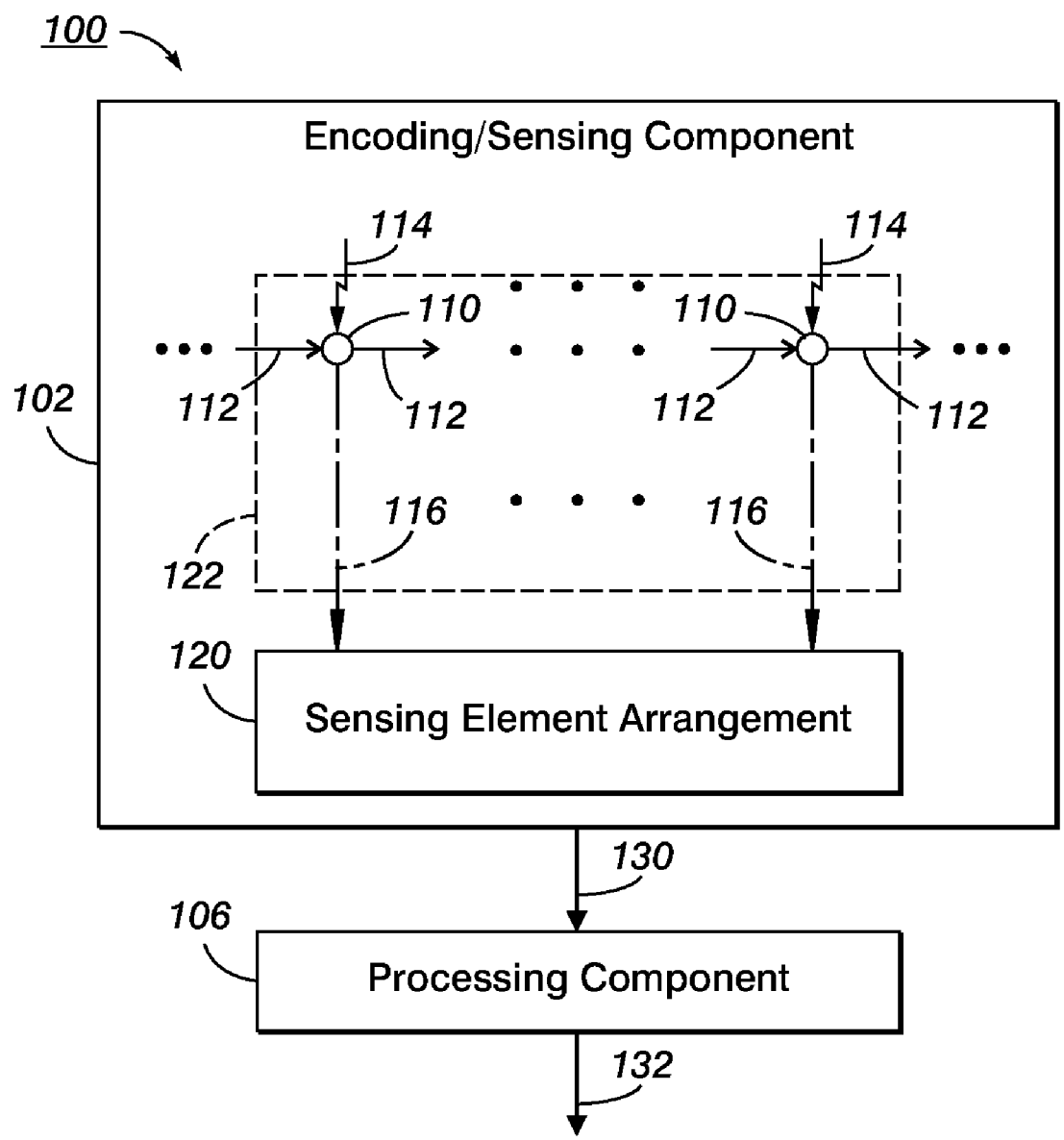
FIG. 2 is a schematic diagram showing components of a system in which an encoding/sensing component can respond to objects having relative motion within an encoding/sensing region.

FIG. 2 schematically illustrates general features of system 100, a system in which light emanating from a moving object can include information about characteristics of the object and in which features described above in relation to FIG. 1 can be implemented. As with other exemplary implementations described below, system 100 involves a combination of parts or components. Encoding/sensing component 102 illustratively includes sensing element arrangement 120, such as of one of the kinds discussed herein, which can provide sensing results such as in the form of electrical signals in response to objects in encoding/sensing region 122 relative to arrangement 120. Output signals from component 102 can be communicated to processing component 106, possibly after conversion to other forms, e.g. for storage, transmission, and processing, such as to optical or other electromagnetic signal forms. Processing component 106 can use the output signals from component 102 in any appropriate way, such as to obtain and/or provide characteristic data indicating information about one or more object characteristics or about excitation or environmental characteristics.

Object 110 illustratively has motion relative to encoding/sensing region 122 in a direction indicated by arrows 112, passing through a succession of positions, two of which are illustrated. In some positions, object 110 can receive excitation, illustrated by arrows 114, and, in response, light as illustrated by arrows 116 can emanate, such as from fluorescence of a dye or other "tag" attached to object 110 or from native fluorescence or autofluorescence of object 110 itself, e.g. due to ultraviolet light or other excitation of intrinsic cell material or other material in object 110; except as otherwise noted, however, implementations described herein can additionally or alternatively employ chemofluorescence, biofluorescence, absorption, scattering, or other phenomena that do not require concurrent excitation. More generally, excitation could take any appropriate form and is not limited to illumination, and excitation and emanation need not be concurrent or otherwise coincident, but could have any appropriate relationship in space and time. Some examples of excitation are described below in relation to exemplary implementations. In addition to encoding due to sensing patterns as described herein, information of various kinds could be encoded in emanating light as a result of excitation and/or filter arrangements, such as information about one or more object characteristics, as described, for example, in co-pending U.S. patent application Ser. No. 12/023,436, entitled "Providing Time Variation in Emanating Light", and co-pending U.S. patent application Ser. No. 12/024,490, entitled "Transmitting/Reflecting Emanating Light with Time Variation", both of which are incorporated herein by reference in their entireties.

Arrangement 120 receives a portion of emanating light represented by arrows 116 and, in response, produces sensing results such as electrical signals with encoded information in accordance with sensing patterns of one or more of the kinds described herein. Based on the sensing results, component 102 provides electrical output signals represented by arrow 130. The electrical output signals can also include at least some of the encoded information from the sensing results produced by arrangement 120, and can simply be the same as the sensing results or can be intermediate signals obtained from the sensing results by circuitry within component 102. As a result, processing component 106 can, in response to the electrical output signals, obtain and/or provide data or other signals; for example, component 106 can provide output signals as represented by arrow 132, and the output signals can include characteristic data indicating information about object characteristics or other types of data indicating, for example excitation or environmental characteristics.

Figure 3:
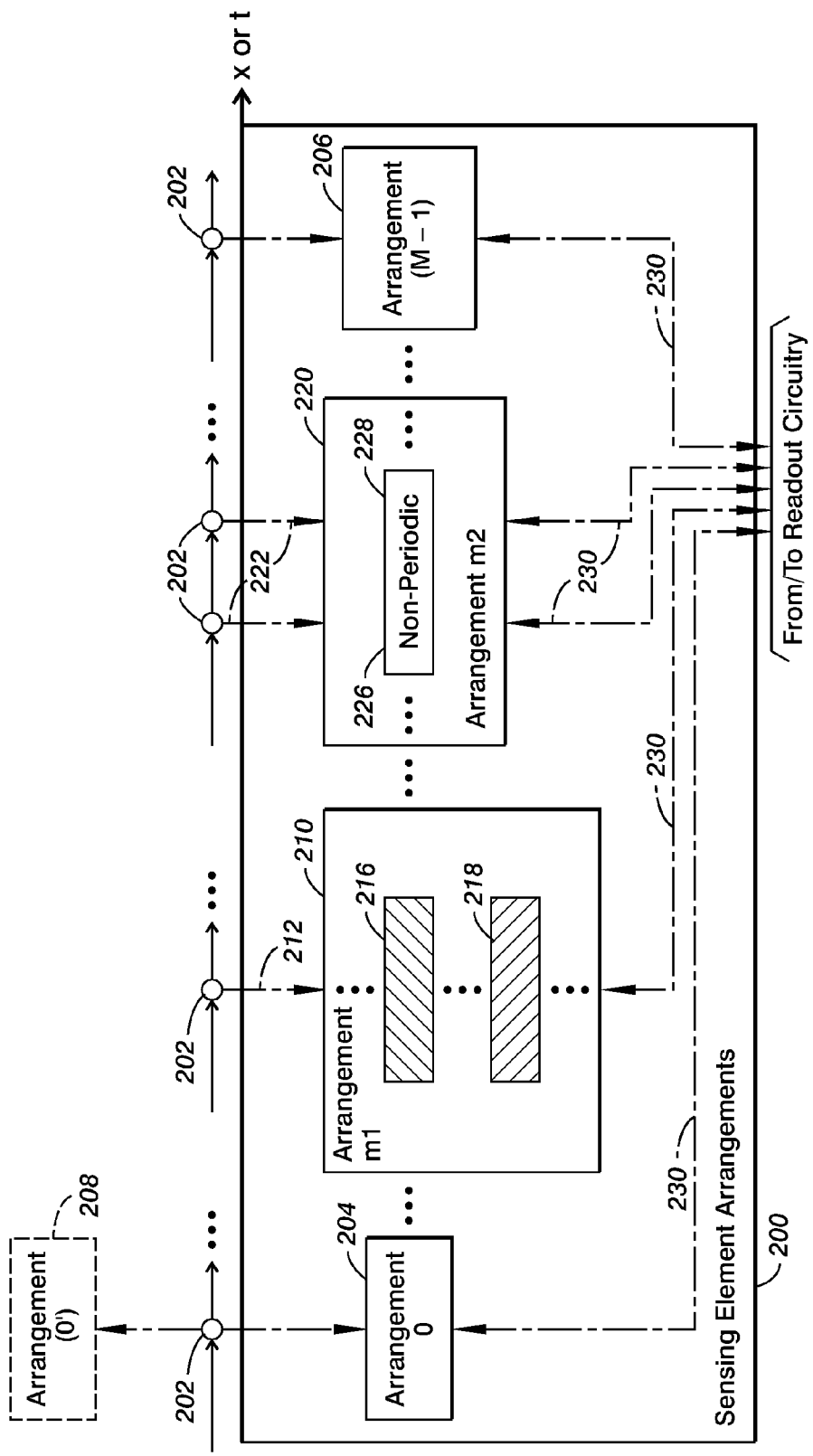
FIG. 3 is a schematic diagram of a sensing element arrangement in an encoding/sensing component as in FIG. 2.
Figure 4:
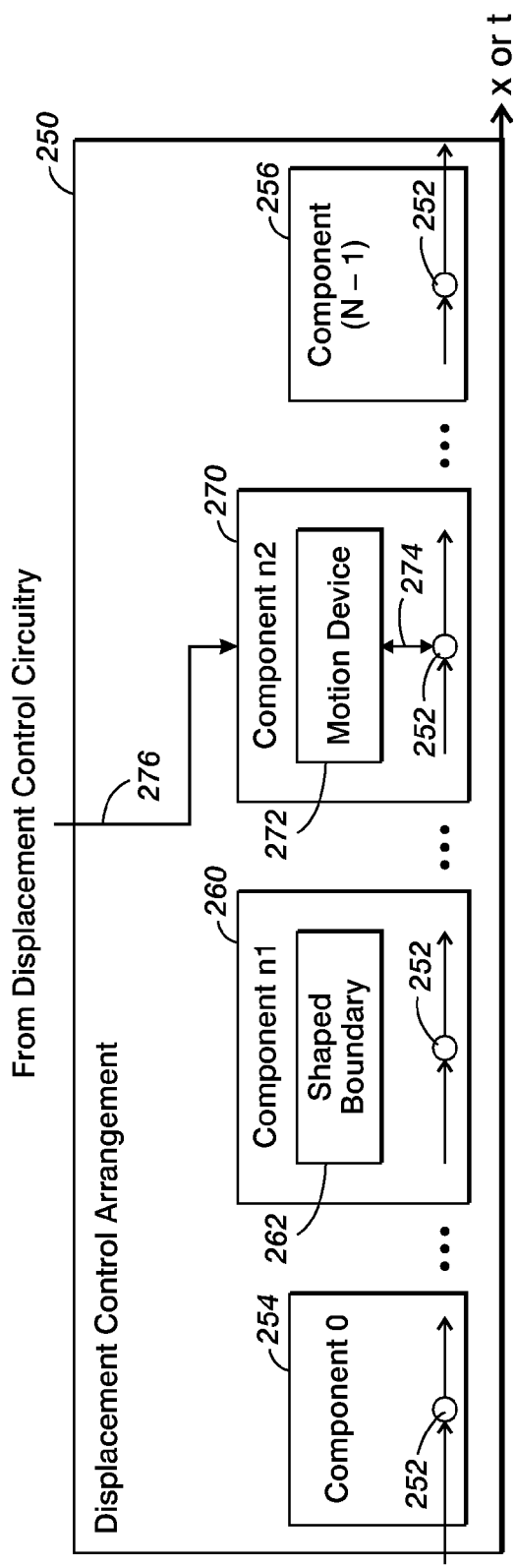
FIG. 4 is a schematic diagram of a displacement control arrangement in an encoding/sensing component as in FIG. 2.

Each of components 102 and 106 and arrangement 120 in FIG. 2 could be implemented in a wide variety of different ways. FIGS. 3 and 4 illustrate several general features of implementations of encoding/sensing component 102, each of which involves one or more arrangements along a path of an object having relative motion.

In FIG. 3, sensing element arrangements 200 are along a path of object 202 as it has relative motion within one or more encoding/sensing regions, each relative to a respective sensing element arrangement within an encoding/sensing component such as component 102 in FIG. 2. As suggested by the one-dimensional coordinate axis labeled "x OR t", the path can be treated either as extending in space, such as along an x-direction, or as occurring over time, t; unless otherwise indicated hereafter in relation to a specific exemplary implementation, the x-direction refers to an object's path and therefore might not in some cases follow a straight line relative to the environment. Although the speed or other rate of displacement of object 202 may vary along the path, information about its speed or other rate of displacement can be sufficient to allow an approximate mapping between its x-direction positions and times t; more generally, mapping between an object's x-direction positions and times t can be based on any suitable system, such as with trigger detection techniques as described in U.S. Pat. No. 7,358,476, entitled "Sensing Photons from Objects in Channels", and in co-pending U.S. patent application Ser. No. 12/337,771, entitled "Obtaining Sensing Results and/or Data in Response to Object Detection", both incorporated herein by reference in their entireties, or from other techniques, including obtaining information such as a trigger signal from an object's encoded signal. In general, however, trigger detection is not necessary for exemplary implementations described herein, except as otherwise indicated, because sensing results indicating time variation can be obtained in response to relative motion of objects within an encoding/sensing region that has a fixed pattern or environment.

Although sensing element arrangements could be positioned in any appropriate way along a path, the exemplary implementations described below generally involve arrangements along the x OR t axis, and FIG. 3 shows several exemplary cross sections of sensing elements within a longitudinal sequence of M arrangements 204 through 206, with each cross section being taken parallel to the x OR t axis and with arrangement 204 labeled "0" and arrangement 206 labeled "(M−1)". As suggested above, sensing element arrangements need not, however, be arranged on only one side of the path as shown, but rather could be positioned at any suitable positions around the path. Also, two or more parallel sensing element arrangements could be at the same position or in overlapping position ranges along the x OR t axis, but displaced in a rotation direction; a configuration of sensing element arrangements that are sufficiently displaced in a rotation direction so that they are around the path is suggested by dashed-line box 208 in FIG. 3, representing a possible position of another sensing element arrangement labeled "(0')", on the opposite side of the path of object 202 from arrangement 204, providing parallel sensing element arrangements.

Arrangement 210, labeled "m1", is illustratively a longitudinal sequence of sensing elements with a combined sensing pattern that is approximately equal to a superposition or scaled superposition of a set of two or more simpler sensing patterns. As object 202 has relative motion within an encoding/sensing region relative to arrangement 210, interaction can occur, as represented by arrow 212; arrangement 210 can, for example, perform photosensing or impedance-based sensing and obtain sensing results that indicate a superposition time-varying waveform with time variation in accordance with all of the simpler sensing patterns in the set. The combined sensing pattern of arrangement 210 could result from any appropriate number of simpler sensing patterns, with patterns 216 and 218 being shown in FIG. 3.

The overall sequence of arrangements 204 through 206 illustrates another longitudinal sequence. Further, non-periodic arrangement 220, labeled "m2" could also be implemented as a longitudinal sequence of sensing elements with which object 202 can interact as it has relative motion within their encoding/sensing region, as represented by arrows 222; arrangement 220 can, for example, perform photosensing or impedance-based sensing and obtain sensing results that indicate a non-periodic time-varying waveform with time variation in accordance with non-periodic arrangement 220. Whether or not it is a longitudinal sequence, arrangement 220 could include non-periodic sensing pattern 226, and the non-periodic time-varying waveform could accordingly be produced in accordance with non-periodic pattern 226.

In general, arrangements 210 and 220 and others of arrangements 200 can have any suitable lengths in the x OR t direction that allow recovery of the encoded information by photosensing and signal processing, including lengths smaller than the apparent extent of object 202 in the x OR t direction that may result in some loss of resolution analogous to blurriness or smearing. As described in relation to some exemplary implementations below, however, each of arrangements 210 and 220 can have length in the x OR t direction greater than or equal to an apparent extent of object 202 in the x OR t direction, while the lengths of arrangements 210 and 220 (and others of arrangements 200) can be sufficiently small that characteristics of object 202 indicated by sensing results do not change while object 202 has relative motion within encoding/sensing regions relative to arrangement 200.

In some specific implementations, sensing elements have parallel sides extending in a direction transverse to the path, and an arrangement of such sensing elements is sometimes referred to herein as a "striped sensor" in which each stripe can be specified by its sensing characteristics (e.g. sensing spectrum and sensed intensity ratio) and its length (or width) in the lengthwise direction.

FIG. 3 also illustrates lines 230 through which each of arrangements 204 through 206 can receive control signals from and provide signals indicating photosensed quantities to readout circuitry (not shown). For example, one or more of arrangements 200 could include trigger detecting circuitry (not shown), and the readout circuitry could, in response to the trigger detecting circuitry, provide control signals causing appropriate readout of photosensed quantities; as noted above, however, trigger detecting circuitry is not required in exemplary implementations described herein except as otherwise noted. As described below in relation to exemplary implementations, readout from IC-implemented sensing elements can include encoded information in a way similar to readout of sensing elements implemented with discrete photosensors.

Sensing element arrangements similar to those shown in FIG. 3 may find application not only in fluidic implementations as described below but also in implementations in which objects in an array move relative to other components due, for example, to scanning movement. One such area of application is in image scanning, such as with scanning sheets of paper or other media that can bear images. In particular, object 202 could be a colored spot on a sheet of paper or other medium, and a sensing element arrangement could be used to obtain information about small differences in color of light emanating from object 202, e.g. color of reflected light in response to broadband illumination. Such information could be used to obtain position and/or color of object 202; for example, if object 202 is a registration mark with a color unique to registration marks, its color could be accurately distinguished from spots of other colors using techniques as described herein and its position could be obtained with sufficient accuracy to allow registration of the sheet, whether for image sensing or for printing or another operation on the sheet. Very high accuracy sensing of color is sometimes referred to as "hyperspectral color sensing".

In FIG. 4, displacement control arrangement 250 is similarly along a path of object 252 as it has relative motion within one or more encoding/sensing regions relative to sensing element arrangements (not shown) in an encoding/sensing component such as component 102 in FIG. 2. Displacement control arrangement 250 includes a combination of one or more displacement control components, each of which is illustratively shown enclosing a respective segment of the path of object 252 as it has relative motion within encoding/sensing regions. It would, of course, be possible to implement displacement control components in other ways, such as where an object has relative motion along a path that is not enclosed within a channel or fluidic structure.

Although displacement control components could be positioned in any appropriate way along a path, the exemplary implementations described below generally involve arrangements of displacement control components along the x OR t axis, and FIG. 4 shows several exemplary components within a sequence of control components 254 through 256, with component 254 labeled "0" and component 256 labeled "(N−1)". Although each displacement control component in the sequence illustratively contains a respective segment of the path, it may be possible to implement displacement control components that affect displacement in overlapping segments of a path or that interact in other ways.

Control component 260, labeled "n1", illustratively includes shaped boundary 262, meaning that a boundary that extends partially or completely around the path, such as the boundary of a fluidic channel, has a shape that affects or controls displacement of object 252 as it has relative motion along the path, such as by affecting its speed or other rate of displacement. Several examples of boundary shapes are described below in relation to exemplary implementations.

Control component 270, labeled "n2", illustratively includes motion device 272. Device 272 can illustratively cause lateral motion of a boundary in its segment of the path, as suggested by bidirectional arrows 274. Line 276 shows that device 272 can receive control signals from displacement control circuitry (not shown). Component 270 could also include trigger detecting circuitry (not shown), and the displacement control circuitry could respond to the trigger detecting circuitry by initiating operation of device 272, either in a steady state or time-varying manner; as noted above, however, trigger detection is not required for exemplary implementations described herein except as otherwise noted. Examples of how device 272 could be implemented are described below in relation to specific implementations.

Figure 5:
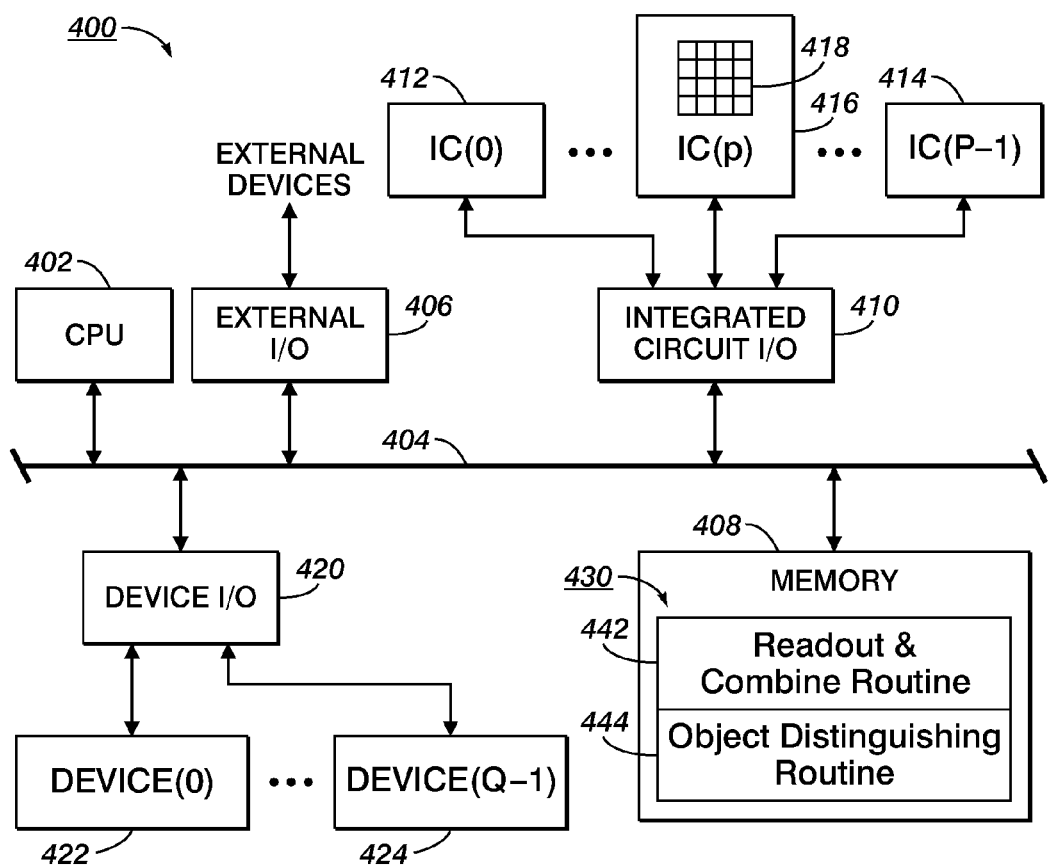
FIG. 5 is a schematic block diagram of a system in which components as in FIG. 2 can be implemented.

FIG. 5 illustrates system 400, an exemplary system that could implement components as in system 100 in FIG. 2. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402. Furthermore, CPU 402 could be the CPU component of any suitable machine such as a laptop or desktop computer, a specialized computer for system 400, and CPU 402 and other digital components as shown could be replaced by other specialized circuitry, such as an analog signal processor; in a relatively simple application, CPU 402 could be implemented with a single digital signal processor or a CPU of a laptop or other personal computer receiving time-varying signals. On the other hand, in some applications, it may prove advantageous to implement all signal processing with analog circuitry, including operations that compare time-varying waveforms and that obtain their derivatives or other related waveforms, making it possible to replace substantially all the digital components as shown if appropriate.

System 400 also includes external input/output (I/O) component 406 and memory 408, both connected to bus 404. External I/O 406 permits CPU 402 to communicate with devices outside of system 400.

Additional components connected to bus 404 are within or connected to system 400. In the illustrated implementation of system 400, IC I/O 410 is a component that permits CPU 402 to communicate with ICs such as ICs with arrays that include photosensing cells; M ICs are illustrated in FIG. 5 by a series extending from IC(0) 412 to IC(P−1) 414. ICs 412 through 414 illustratively include IC(p) 416 with array 418, which includes photosensing cells. Similarly, device I/O 420 is a component permitting CPU 402 to communicate with various devices in system 400, such as sensing and control devices; Q devices in system 400 are represented in FIG. 5 by device (0) 422 through device (Q−1) 424. In addition to discrete sensing elements that photosense or perform impedance-based sensing as described above in relation to FIG. 3 and displacement control components as described above in relation to FIG. 4, devices 422 through 424 can include fluidic devices such as pumps, metering electrodes, smart gates, and other devices for gating and bifurcating, valves, flow or pressure sensors, and so forth. Such fluidic devices could be implemented in various ways; smart gates, for example, could be implemented with MEMS-style microgates or by using electromagnetic forces, which are effective because most particles are charged such that an electric field can be used to direct them as desired in a channel.

Memory 408 illustratively includes program memory 430 although instructions for execution by CPU 402 could be provided in various other forms of software or hardware, on or off of CPU 402. The routines stored in program memory 430 illustratively include readout and combine routine 442 and object distinguishing routine 444. In addition, program memory 430 can also store a number of subroutines (not shown) that CPU 402 can call in executing routines 442 and 444, and can also store additional routines for encoding by techniques other than sensing patterns. Examples of such additional encoding routines and of exemplary implementations of object distinguishing routine 444 are described in co-pending U.S. patent application Ser. No. 12/022,485, entitled "Obtaining Information from Time Variation of Sensing Results"; in co-pending U.S. patent application Ser. No. 12/023,436, entitled "Providing Time Variation in Emanating Light"; and in co-pending U.S. patent application Ser. No. 12/024,490, entitled "Transmitting/Reflecting Emanating Light with Time Variation", all of which are incorporated herein by reference in their entireties.

In executing routine 442, CPU 402 can, for example, perform pre-sensing readout, obtain object information and sensing periods, perform sensing readout with sensing periods and analog adjustment, digitally adjust sensing results and store quantities for an object, and combine the quantities for an object to produce its characteristic data. Routine 442 could, for example, call a subroutine implemented as described in U.S. Pat. No. 7,358,476, entitled "Sensing Photons from Objects in Channels", and in U.S. Patent Application Publication No. 2007/0146704, entitled "Sensing Photons Energies Emanating from Channels or Moving Objects", each of which is incorporated herein by reference in its entirety. Such a subroutine can be implemented for single objects moving past arrays or for spaced multiple objects moving past arrays, provided spacings between objects are sufficient to avoid interference; such a subroutine could also be implemented for objects moving past arrangements of discrete sensing elements. Also, such a subroutine can follow a general strategy of performing a series of readout operations, after which information for an object is combined and its characteristic data is provided, although it would also be possible to provide the information from each readout operation immediately.

Figure 6:
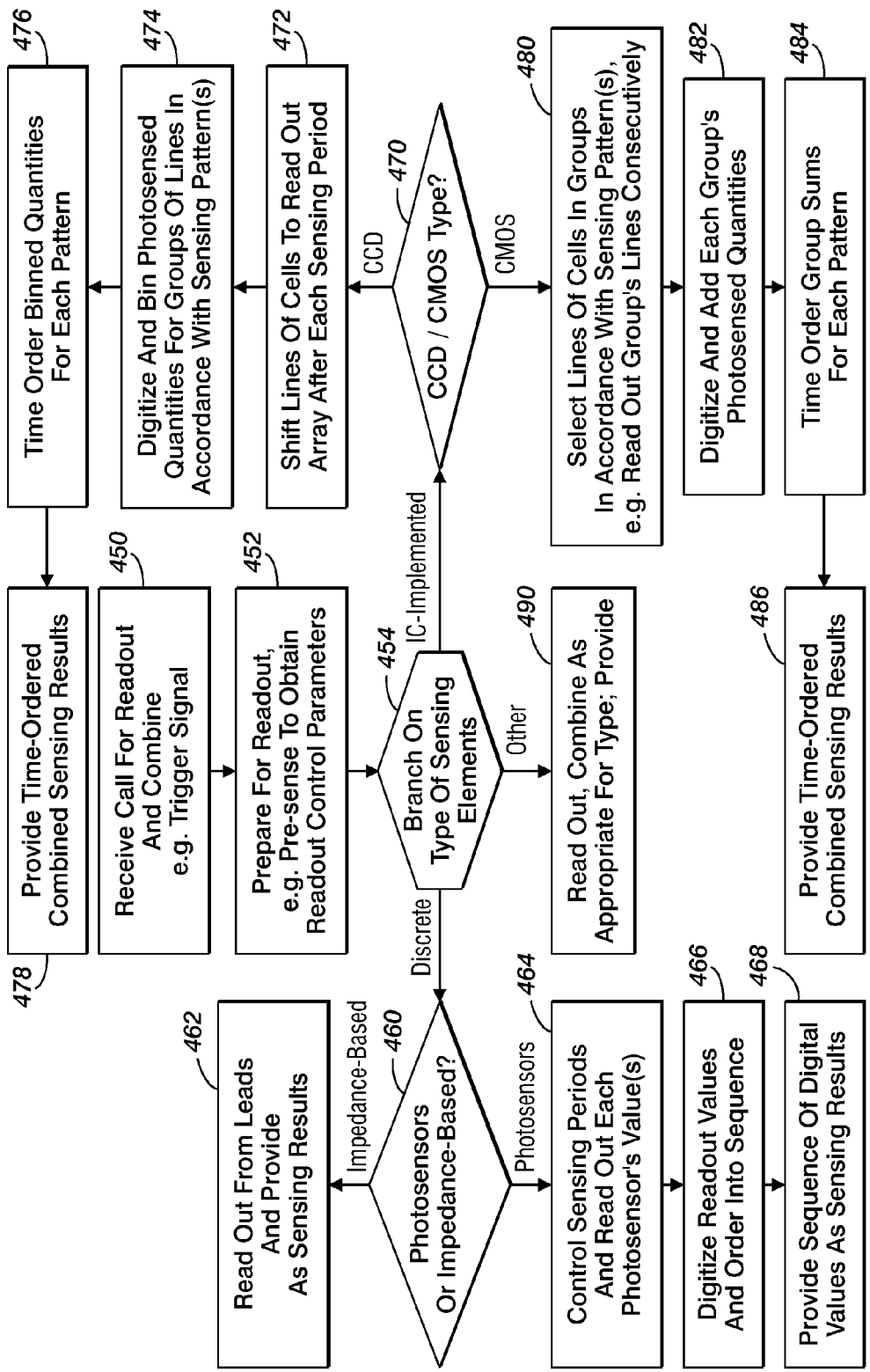
FIG. 6 is a flow chart showing general operations in an implementation of a readout and combine routine as in FIG. 5.

FIG. 6 illustrates features in exemplary implementations of readout and combine routine 442. Operations as in FIG. 6 could be implemented for a variety of different types of encoder/sensors, with sensing elements in a variety of arrangements, including arrangements that include, for example, discrete photosensing elements, impedance-based sensing elements such as electrodes and Hall effect sensors, and IC-implemented sensing elements. Techniques as in FIG. 6 are not limited to fluidic relative motion as described above, but could be used with other types of relative motion, some of which are described below.

The implementation of FIG. 6 begins with the operation in box 450 receiving a call to perform readout and combine operations. This call could come from another routine and/or, as suggested in box 450, could result from a trigger signal received from trigger detector circuitry, as in implementations in which readout and combine operations are performed separately for each of a series of distinguishable objects that have relative motion into a trigger detection region of a trigger detector upstream from an arrangement of sensing elements. In other types of implementations, the call received in box 450 could depend on occurrence of some other event or on passage of time, such as an interval between periodic readout and combine operations, in which case trigger detection would not be necessary.

The operation in box 452 then prepares for readout, such as by initializing data structures and obtaining values to be used during readout. As suggested in box 452, this operation could include a pre-sensing readout operation from which readout control parameters are obtained. Exemplary readout control parameters might include object position and speed, object size, fluid speed, sensing periods, and so forth.

After the operation in box 452, appropriate subsequent operations can be performed for the type of sensing elements in the encoder/sensor, with a branch between alternative types of sensing elements represented by box 454; an actual implementation might be specialized for a specific type of sensing element, in which case the branch in box 454 and other branches described below would not need to be implemented as separate decision operations—only the operations for the specific type of sensing element would be required. Exemplary subsequent operations are illustrated for discrete photosensing elements, for discrete impedance-based sensing elements, and for CCD-type and CMOS-type photosensing arrays, but the techniques of FIG. 6 could also be implemented for other types of encoder/sensors, including types with more than one type of sensing elements or sensing elements of other types.

If the encoder/sensor includes discrete sensing elements that are photosensors or that are impedance-based sensing elements, appropriate subsequent operations can be performed, with a branch between photosensing and impedance-based sensing elements represented by box 460. As noted above, the branch in box 460 might not need to be implemented as a separate decision operation.

For impedance-based sensing elements such as electrodes, Hall effect sensor, inductors, etc., the operation in box 462 reads out and combines sensed values in an appropriate way. In the illustrated example, sensed values from impedance-based sensing elements are combined by being read out from leads through appropriate circuitry as an object has relative motion within the encoding/sensing region. Although the combined analog signal could be provided directly as sensing results or can be digitized and then provided. With appropriate circuitry, the use of common leads can effectively add or multiply analog values from all the sensing elements in a sensing pattern, with the analog value from each sensing element at a given time indicating an object's effect on the sensing element at that time; therefore, if the object is sufficiently small relative to the minimum feature size of the arrangement's sensing pattern and if its relative motion within the encoding/sensing region does not exceed an appropriate maximum speed, the combined analog signal indicates a time-varying waveform for the object. Other circuitry could be used, for example, with implementations in which impedance-based sensors are read out in parallel.

For discrete photosensors, the operation in box 464 reads out sensed values in an appropriate way and the operation in box 466 combines them, also in an appropriate way, before they are provided in box 468. In the illustrated example, the operation in box 464 provides control signals that determine sensing periods for each photosensor, and, after each sensing period, can read out an analog value indicating a photosensed quantity during the sensing period; various alternative readout techniques could be used with discrete photosensors having appropriate features; for example, if a photosensor has analog output that is continuously available and that, at any given time, indicates a photosensed quantity during a preceding interval, the analog output could be read out by sampling at appropriate intervals to obtain a series of analog values. To combine analog values read out in box 464 for a number of discrete photosensors, the operation in box 466 can illustratively digitize the readout analog values and then order the resulting digital photosensed quantities into a sequence in accordance with positions and extents of the photosensors and, if appropriate, an object's relative position and relative speed, resulting in a sequence of digital values that indicate one or more time-varying waveforms. The operation in box 468 can then provide this sequence of digital values as sensing results, such as for the object that had relative motion in the encoding/sensing region.

In ordering photosensed quantities into a sequence, the operation in box 814 performs a simple example of "time ordering", a term that refers herein to any operation that begins with a set of digital values or subsequences of digital values obtained from sensing results during a given period of time and that a resulting sequence of digital values that approximates an actual sequence of photosensed quantities or other sensed values that occurred in the period of time. Time ordering can therefore include, in addition to simple concatenation of digital values or subsequences, various operations in which digital values are smoothed, interpolated, combined at subsequence overlaps, or otherwise adjusted to produce the resulting sequence of digital values. The resulting sequence could exist in any appropriate form, e.g. as digital values stored in a sequence of actual or virtual memory locations, as a data structure in which digital values are in sequence, or as any other suitable type of sequence of digital values; where the raw sequence includes information that is redundant or unnecessary or that is unusable for some reason, the resulting sequence could be in a compressed form, e.g. with data indicating position in sequence and/or duration for each digital value or with any other suitable compression technique.

If the arrangement includes IC-implemented sensing elements that include photosensing cells in arrays on one or more ICs, different subsequent operations can be performed, with a branch depending on readout type being represented by box 470. As noted above, the branch in box 470 might not need to be implemented as a separate decision operation. Also, if arrays with other readout types are used, the subsequent operations could be implemented as appropriate for the particular readout types involved—CCD-type readout and CMOS-type readout are two exemplary approached that are now commonly used, but other types might be developed in the future. Whatever type of readout is performed, an arrangement of IC-implemented sensing elements, such as with arrays of photosensing cells, can be used to flexibly approximate a number of different sensing patterns that could alternatively be implemented with discrete sensing elements.

The term "CCD" is an abbreviation for "charge-coupled device", which describes a type of circuitry that can operate as a photosensing cell in an array. Arrays of CCD devices, sometimes referred to herein as "CCD arrays", are typically readout with shifting techniques, sometimes referred to as "bucket brigade" techniques, in which photosensed quantities are shifted along a line of cells, whether a row or column; the term "CCD-type readout" therefore is used herein to encompass any readout technique in which photosensed quantities are shifted along a line of cells toward an end of the line at which they are received by readout circuitry. CCD-type readout could thus be implemented with an array of cells that are not CCDs, if the array includes appropriate circuitry so that it can be read out in this way, and all the lines of such an array could be shifted in parallel to read out the entire array.

To perform CCD-type readout, the operation in box 472 can shift lines of cells in an array to read out photosensed quantities from the array after each of a series of one or more appropriate sensing periods. The operation in box 474 can digitize photosensed quantities as they are shifted out of the array and can combine the photosensed quantities from groups of lines in accordance with one or more sensing patterns by "binning", which refers herein to an operation that obtains a combined value such as a value indicating a sum or product of the photosensed quantities shifted out of one or more lines of an array after one sensing period; photosensed quantities, such as from groups of lines, are combined "in accordance with" a sensing pattern if the photosensed quantities are combined in substantially the same way the sensing pattern would combine them. For each pattern's binning in box 474, the operation in box 476 can then combine the binned quantities for the groups of lines by ordering them into an appropriate sequence to obtain a series of binned quantities that indicates one or more time-varying waveforms encoded in accordance with the pattern; for example, the binned quantities can be ordered into a sequence in accordance with positions and longitudinal widths of the groups in the pattern and, if appropriate, an object's position and speed relative to the encoding/sensing region, resulting in a sequence of digital values that indicate one or more time-varying waveforms encoded in accordance with the pattern. After the time-ordered combined sensing results for each pattern are obtained in box 476, the operation in box 478 can then provide them as sensing results.

The term "CMOS" is similarly an abbreviation for "complementary metal oxide semiconductor", which describes another type of circuitry that can operate as a photosensing cell in an array. In contrast to CCD-type readout, arrays of CMOS devices, sometimes referred to herein as "C MOS arrays", are typically read out in response to signals that can select any single line of cells of the array to be directly read out in parallel; in effect, a line of cells, such as a row, can be addressed and then read out. The term "CMOS-type readout" therefore is used herein to encompass any readout technique in which a single line of cells of the array can be selected and read out in parallel. CMOS-type readout could thus be implemented with an array of cells that are not CMOS devices, if the array includes appropriate circuitry so that it can be read out in this way; the entire array could be read out by selecting and reading out every line of the array in turn.

To perform CMOS-type readout, the operation in box 480 can select lines of cells in an array for readout in groups in accordance with one or more sensing patterns, e.g. a longitudinal sequence: readout of cells is "in groups in accordance with" a sensing pattern if groups of the cells are read out in a way that groups them in substantially the same way the sensing pattern would group them. For example, lines can be read out after each sensing period in a sequence in which the lines of each group in a pattern can be read out consecutively, one after another, so that they can be more easily combined than if lines of different groups were intermixed; as photosensed quantities for the lines of a group in a pattern are read out, the operation in box 482 can digitize and add them to obtain a sum of photosensed quantities for each group from a given sensing period. In an alternative approach, all the lines in the array can be read out and their photosensed quantities can be stored, after which the lines of groups in each pattern can be combined. As in box 476, the operation in box 484 can then combine the photosensed quantity sums for the groups of lines by ordering them into an appropriate sequence to obtain a series of sums that indicates one or more time-varying waveforms encoded in accordance with the pattern; for example, the photosensed quantity sums can be ordered into a sequence in accordance with positions and longitudinal widths of the groups and, if appropriate, an object's position and speed relative to the encoding/sensing region, resulting in a sequence of digital values that indicate one or more time-varying waveforms encoded in accordance with the pattern. After the time-ordered combined sensing results for each pattern are obtained in box 484, the operation in box 486 can then provide them as sensing results.

After time ordering in either of boxes 476 or 484, the operation in box 486 can then provide one or more time-ordered sequences of combined values as sensing results. Sensing results provided in this way can have substantially the same form as those provided in either of boxes 462 and 468, and appropriate scaling, shifting, normalization, and other suitable operations can be performed so that time-varying waveforms indicated by sensing results from different types of sensing elements have magnitudes and phases that allow comparison with each other or with reference waveforms.

Sensing results provided in boxes 478 and 486 can have substantially the same form as those provided in either of boxes 462 and 468. Appropriate scaling, shifting, normalization, and other suitable operations can be performed so that time-varying waveforms indicated by sensing results from different types of sensing elements have magnitudes and phases that allow comparison with each other or with reference waveforms.

If the encoder/sensor includes another type of sensing elements other than those handled as described above, an appropriate operation for the type of sensing elements can be performed, as shown in box 490. The operation in box 490 can read out and combine sensed values in any appropriate way to obtain sensing results, and the sensing results can then be provided in any appropriate way.

The operations in FIG. 6 are only exemplary, and various other combinations of operations could be performed to read out and combine sensed values from sensing elements of various types. Additional features of readout and combine operations are described below in relation to specific implementations.

Figure 7:
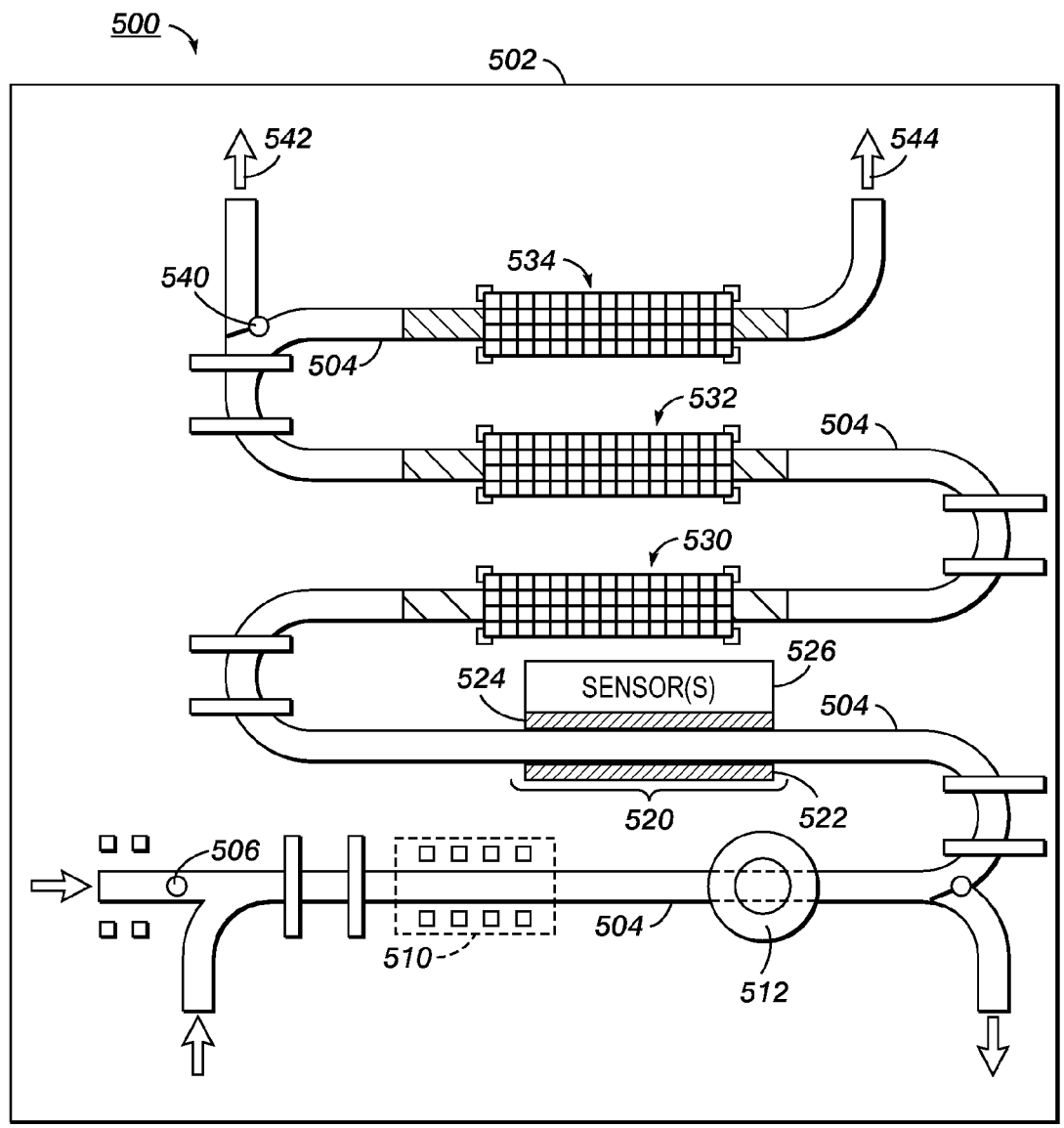
FIG. 7 is a schematic diagram of an analyzer in a fluidic structure, where the analyzer can include a system that can be implemented as in FIGS. 5 and 6.

FIG. 7 illustrates an application of a system as in FIGS. 5 and 6 in analyzer 500 on support structure 502, a fluidic structure. Defined in support structure 502 is serpentine channel 504 through which object 506 can have relative motion, carried by fluid such as liquid, gas, or aerosol or moved in some other appropriate way. Object 506 can, for example, be a biological cell or another object of any of the types mentioned above.

The manner in which object 506 enters channel 504 and is carried by fluid can be the same as described in U.S. Pat. No. 7,358,476, entitled "Sensing Photons from Objects in Channels", and U.S. Patent Application Publication No. 2007/0146704, entitled "Sensing Photons Energies Emanating from Channels or Moving Objects", each of which is incorporated herein by reference in its entirety. As explained there, object 506 can be carried through channel 504 by operation of propulsion components and can be purged or otherwise caused to exit, together with fluid that is carrying it, from one of several outlets, such as through toggling of valves. While in channel 504, object 506 can have relative motion within interaction regions relative to a series of object interaction components, each of which can obtain information about object 506.

The first two interaction components after object 506 enters channel 504 are illustratively Coulter counter 510, an electrically based particle size detector, and Mie scatter sensor 512, also a particle size detector. Information about size of object 506 from Coulter counter 510 and Mie scatter sensor 512 can be used in obtaining information about its other characteristics. Various other techniques could also be used to obtain particle size information, including techniques that use chirped filter patterns, random filter patterns with small feature size, staircase periodic filter patterns, and so forth, and such techniques could make it unnecessary to use specialized components to determine particle size. If the particle size is much smaller than the features of the patterning, the time-varying signal can reflect all features of the patterning; but if the particle size is larger than some features of the patterning, then some features will be weaker or even missing in the time-varying signal. For example, in chirped patterning, time variation will occur as a relatively large particle has relative motion past pattern features that are even larger than the particle, but then will weaken and stop occurring as the particle passes progressively smaller pattern features; in random patterning that includes both large and small features, time variation will occur across the entire pattern as a very small, point-like particle has relative motion past the pattern, but time variation will occur only where there are large pattern features for a relatively large particle—in this case, the effect is similar to filtering out high frequency components of the time-varying signal. Therefore, particle size information is encoded in the time-varying signal.

The next interaction component along channel 504 is object interaction component 520, shown schematically in a cross-sectional view along an axis similar to the x OR t axis in FIGS. 3 and 4, although it would typically be implemented instead with components above and below channel 504, similarly to other object interaction components described below. The schematic illustration of component 520 includes excitation/displacement component 522, filter component 524, and a sensing component that includes one or more sensors 526, all of which might be implemented in a variety of ways, including some of those described above and below; one or more of components 522, 524, and 526 could be omitted or replaced in specific implementations.

After passing through component 520, object 506 could be characterized without obtaining further information, or, as in the illustrated implementation, object 506 can continue through subsequent object interaction components, illustratively including components 530, 532, and 534. These could, for example, include first and second fluorescence sensing components and a Raman scatter sensing component. Information obtained from any combination of the object interaction components can be used to distinguish between types of objects, such as different types of biological cells; to distinguish objects from environment or background; or to obtain information about excitation or environmental features. Based on a distinction between types of objects or between objects and environment or background, valve 540 at a bifurcation junction can be toggled between two positions, with object 506 exiting as indicating by arrow 542 if valve 540 is in one position and exiting as indicated by arrow 544 if valve 540 is in another position.

The fluidic implementation in FIG. 7 is merely illustrative of a wide variety of implementations of the techniques described herein. For example, any appropriate fluidic or nonfluidic techniques could be used with a wide variety of different types of objects and various types of relative motion to obtain various types of motion-affected sensing results, such as with information about object characteristics.

Figure 8:
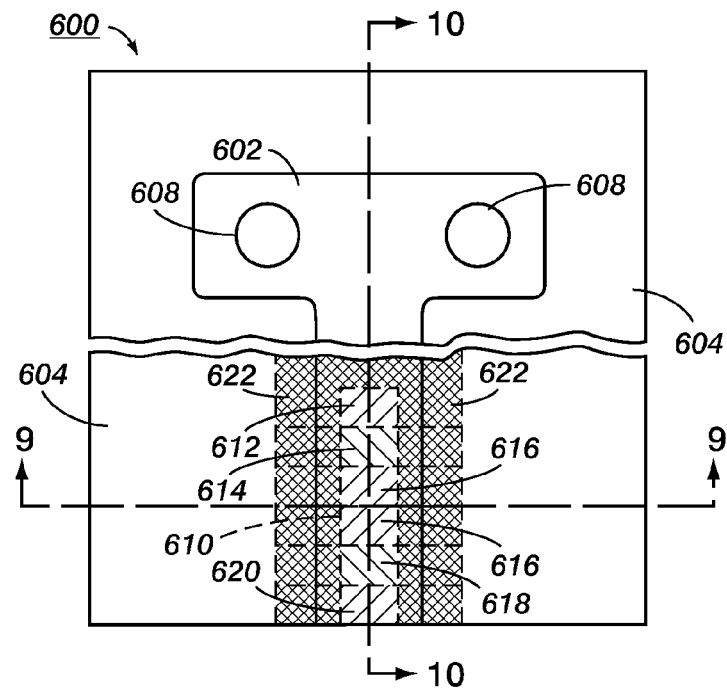
FIG. 8 is a top view of an article that can include a sensing arrangement and that can be included in an encoding/sensing component as in FIG. 2.

FIG. 8 illustrates an example of article 600 with components that could be operated similarly to object interaction component 520 in FIG. 7. Some features of article 600 can be understood from description in co-pending U.S. patent application Ser. No. 11/777,712, entitled "Producing Fluidic Waveguides", incorporated herein by reference in its entirety. For example, article 600 includes a "fluidic structure", used herein to refer to a structure that depends for its operation on fluid positioning or fluid flow, such as, for liquids or gases, in response to pressure or, for liquids, as a result of surface tension effects; in general, the term "fluid" is used herein to encompass all media that can flow, including liquids, gases, aerosols, and so forth. The related term "channel" refers herein to any tube or other enclosed passage within a fluidic structure through which fluid flows during operation. A channel is therefore an example of a "fluidic region", used herein to refer to a region that can contain fluid. An operation "positions" fluid in a channel if it changes the fluid's position in any way that leaves the fluid in the channel.

A channel or portion of a channel through which objects can have relative motion along paths are treated herein as having the directional orientation described above in relation to a path. In addition, a "cross section" lies in a plane perpendicular to a direction in which a local net flow of fluid through the channel or portion can occur; a direction in which a cross section extends can be referred to as a "transverse direction" or a "lateral direction." A channel or portion with approximately uniform cross section and substantially linear longitudinal direction can be referred to as "straight", and the channels and portions described herein are generally straight unless otherwise indicated.

In order to contain fluid, a channel or other fluidic region is typically "bounded", meaning that surfaces or surface areas bound it on at least some sides. A "boundary" of a channel or portion is the surface or combination of surfaces within which fluid contained in the channel is confined. A "port" is an opening that extends through the boundary of a channel or portion such that fluid can enter or exit through the port; in general, a port is relatively small compared to the length of the channel or portion, and the boundary is treated as extending across the port as if the port did not exist.

As described below, article 600 can include two light-transmissive components, and FIG. 8 shows article 600 in a top view through one light-transmissive component. In this view, the inner region between the light-transmissive components includes two main portions, channel portion 602 that can contain fluid and non-channel portion 604 that surrounds channel portion 602; channel portion 602 is illustratively shaped like a "T", but could instead have an L-shape or any other suitable shape, including a serpentine shape as in FIG. 7. Ports 608 are openings through one of the light-transmissive components, allowing entry and exit of fluid into and out of channel portion 602.

FIG. 8 also shows sensing element arrangement 610 in dashed outline, an arrangement with a sensing pattern resulting, for example, from an appropriate arrangement of discrete sensing elements or from operation of an IC-implemented sensing element that is read out in accordance with the sensing pattern. Arrangement 610 illustratively includes a longitudinal sequence of sensing elements 612, 614, 616, 618, and 620. Sensing elements 612, 616, and 620 are illustratively cross-hatched similarly to each other to indicate that they have the same or approximately the same sensing spectra, sensed intensity ratio, extent, and/or other sensing characteristics, while sensing elements 614 and 618 are also cross-hatched similarly to each other, illustrating that they also have the same or approximately the same sensing spectra, sensed intensity ratio, extent, or other sensing characteristic, sensing characteristics that are different than those of sensing elements 612, 616, and 620. In other words, arrangement 610 has a striped sensing pattern in which each of sensing elements 612 through 620 can be specified by its sensing characteristics and its length in the x-direction in FIG. 8.

Surrounding arrangement 610, blocking material 622 can be structured and positioned to provide an aperture for emanating light. Blocking material 622 can, for example, be a material with approximately zero light transmission that prevents scattering and reflection of light, also preventing light entering arrangement 610 from nearby fluorescing objects. Blocking material 622 can be produced during the same operation that produces sensing elements 612 through 620 and can in effect be part of arrangement 610.

Figure 9:
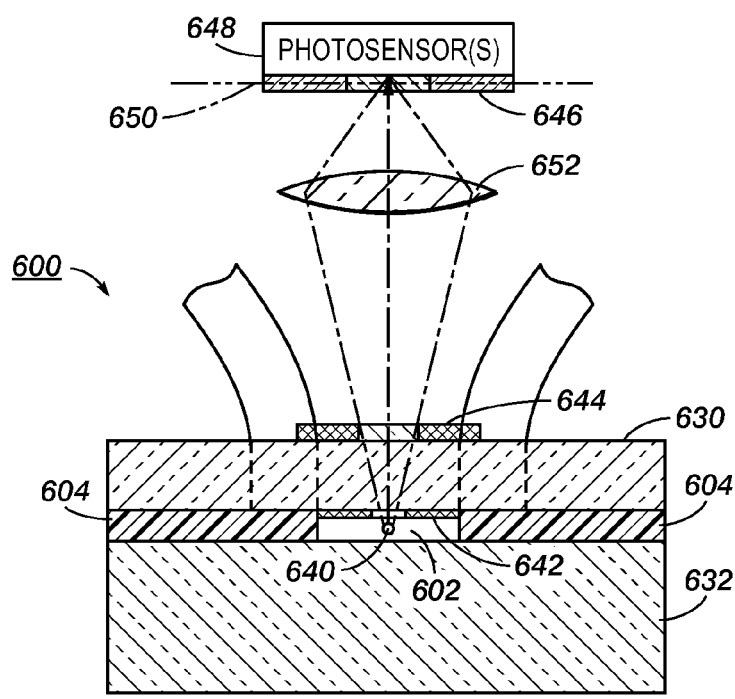
FIG. 9 is a cross-sectional view of an implementation of an article similar to that in FIG. 8, taken along the line 9-9.

The cross section in FIG. 9 shows how light-transmissive components 630 and 632 are separated by material in non-channel portion 604. For example, components 630 and 632 can each include quartz or another suitable material such as glass or acrylic with an appropriate thickness; in a successful implementation, for example, component 630 has a thickness of approximately 0.3 mm, while component 632 has a thickness of approximately 1.0 mm. The distance between them can be approximately 50 μm, maintained by material in non-channel portion 604, which could, for example, be a suitable photoresist material such as SU-8 or another polymer material. Alternatively, a wall (not shown) could be formed around channel portion 602, and non-channel portion 604 could then be filled with epoxy material that seals a lateral boundary around channel portion 602. Various other techniques could be used to produce a similar fluidic structure, including hot embossing, nano-imprinting, or injection molding, and channel portion 602 can have appropriate dimensions, such as for waveguiding as described in co-pending U.S. patent application Ser. No. 11/777,712, entitled "Producing Fluidic Waveguides", incorporated herein by reference in its entirety.

FIG. 9 also shows object 640 from which light is illustratively emanating upward, as illustrated by an emission cone. Although the emission cone is illustratively shown as a single cone, the actual emission cone would depend on angles of total internal reflection at surfaces through which emanating light is transmitted in article 600. FIG. 9 illustrates three alternative filter assembly positions, with filter assembly 642 facing channel portion 602, on the lower surface of component 630; with filter assembly 644 being outside of channel 602 on the upper surface of component 630; and with filter assembly 646 being spaced apart from the upper surface of component 630, adjacent photosensing arrangement 648, which could, as in other implementations, be implemented with one or more discrete large area photosensors in a sensing pattern (such as photo-diodes, avalanche photo-diodes (APDs), or photo-multiplier tubes (PMTs)), or with ICs that include one or more appropriate arrays of photosensing cells whose sensed quantities can be read out and combined to obtain sensing results in accordance with one or more sensing patterns. As suggested in FIG. 9, the emission cone from object 640 is imaged onto image plane 650 extending through filter assembly 646 by optical component 652, illustratively shown as a single lens, but which could be any suitable lens, lens system, or other optical component. Additional explanation of feature size considerations is set forth in co-pending U.S. patent application Ser. No. 12/024,490, entitled "Transmitting/Reflecting Emanating Light with Time Variation", incorporated herein by reference in its entirety.

Figure 10:
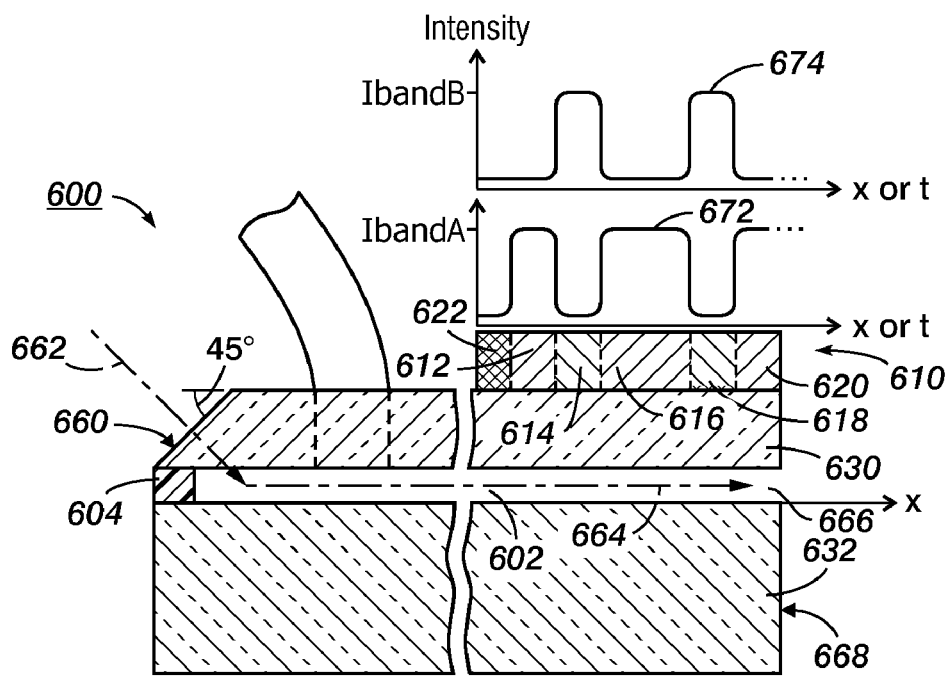
FIG. 10 is a cross-sectional view of another implementation of an article similar to that in FIG. 8, taken along the line 10-10, together with graphs of sensing results.

The cross section in FIG. 10 further illustrates how component 630 has oblique surface 660, a light interface surface that is illustratively at an angle of approximately 45° to the inward-facing surfaces of components 630 and 632. As a result, incident excitation light at a direction approximately perpendicular to surface 660, as illustrated by arrow 662, can cause and couple with light propagating through channel portion 602, as illustrated by arrow 664, as described, for example, in co-pending U.S. application Ser. No. 11/777,712, entitled "Producing Fluidic Waveguides", incorporated herein by reference in its entirety. Excitation light could have any appropriate wavelength, such as 266 nm, for example. The distance from surface 660 to obtain appropriate homogeneity can be determined, as described, for example, in U.S. Patent Application Publication No. 2008/0013877, incorporated herein by reference; the distance can also be sufficient to allow integration of blocking material 622.

In the illustrated implementation, the end of channel portion 602 at right in FIG. 10 is open, providing an additional port 666 through which fluid can enter into or exit out of channel portion 602. Alternatively, article 600, instead of ending at transverse end-surface 668, could extend to another area with ports similar to ports 608, such as with a part symmetrical about the position of surface 668; in this case, fluid could flow through channel portion 602 between ports 608 and similar ports at the opposite end of channel portion 602.

In the implementation in FIG. 10, sensing elements such as discrete photosensing devices within arrangement 610 are schematically shown in cross section with different hatching patterns indicating different sensing spectra, and, in this implementation, the sensing elements alternate along the longitudinal direction of channel portion 602, alternating between two sensing spectra that respond to two different photon energy subranges referred to as "band A" and "band B". The sensing elements could also be surrounded on all sides by a layer of blocking material 622. The size of the gap, if any, between adjacent sensing elements depends, for example, on the resolution of the technique used to position and/or attach sensing elements within arrangement 610. If sensing elements with two different sensing spectra are produced by printing, on alternating discrete photosensing areas, two different light-absorbing materials that have different absorption spectra (in which case a surrounding layer of shadow or transparent material could also be printed around them), the registration and gaps between filters depend on the resolution of the printing technique used; examples of such techniques are described in U.S. Pat. No. 7,365,022, entitled "Additive Printed Mask Process and Structures Produced Thereby", and in co-pending U.S. patent application Ser. No. 11/755,717, entitled "Surface Energy Control Methods for Color Filter Printing", each of which is incorporated herein by reference in its entirety. In general, however, the techniques described herein do not require highly precise positioning of filters and discrete photosensing elements—a small gap between filters or photosensing elements should not significantly affect time-varying signals that result from an object having relative motion past such filters or photosensing elements while it emanates light.

The upper part of FIG. 10 includes two graphs illustrating intensities detected by arrangement 610 in response to two types of objects, one emanating light in "band A", the other emanating light in "band B". Sensing elements 612, 616, and 620 have sensing spectra that are highly responsive to "band A" but not to "band B", while sensing elements 614 and 618 have sensing spectra that are highly responsive to "band B" but not to "band A".

Curve 672 illustrates intensities indicated by sensing results from arrangement 610 if object 640 emanates light in "band A" as it has relative motion within an encoding/sensing region in channel portion 602. In other words, the emanating light's photon energy distribution matches the sensing spectra of sensing elements 612, 616, and 620 so that curve 672 is high along those sensing elements but low along sensing elements 614 and 618; its high value is indicated on the vertical axis as "IbandA".

Curve 674, on the other hand, illustrates intensity indicated by sensing results from arrangement 610 if object 640 emanates light in "band B" as it has relative motion within the encoding/sensing region. In this case, the emanating light has a photon energy distribution that matches the sensing spectra of sensing elements 614 and 618 but not of sensing elements 612, 616, and 620, so that curve 674 is at a high intensity along sensing elements 614 and 618, "IbandB", and at a low intensity elsewhere.

Curves 672 and 674 illustrate an example in which two different types of objects provide signals that are approximately complementary, except at the far left along blocking material 622 where both curves are at approximately zero intensity. In a simple implementation, for example, sensing elements 612, 616, and 620 could be covered by red band pass filters, sensing elements 614 and 618 could be covered by green band pass filters, each object could either be a red fluorescing particle or tag, i.e., emanating light in "band A", or a green fluorescing particle or tag, i.e., emanating light in "band B". As suggested, curves 672 and 674 could be plotted based on the x-direction position of object 640 or based on the t-position within the sensing results obtained from arrangement 610, which could be provided continuously with suitable circuitry combining time-varying analog photosensed quantities from all sensing elements or by any suitable form of sampling, such as by periodic readout and combine operations performed on the sensing elements at an appropriate frequency. The high intensities of curves 672 and 674 would be reduced to the extent that blocking material 622 prevents light from reaching arrangement 610.

As a result, output signals from arrangement 610 can be used to distinguish types of objects, in this case to distinguish objects that emanate light in "band A" from objects that emanate light in "band B", and examples of techniques that distinguish types of objects in various ways are mentioned below in relation to exemplary implementations. In some examples, emanating light encoded by an arrangement with stripe-like sensing elements of random lengths can be analyzed by comparing a resulting time-varying signal with one or more templates or other signals to determine an object's type, displacement, and position to a high level of precision.

Figure 11:
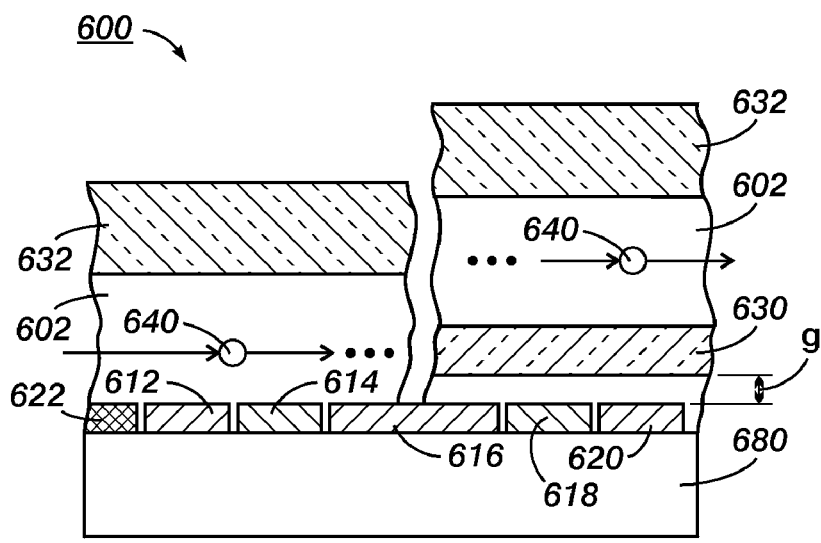
FIG. 11 is a partially schematic cross-sectional view of an article showing two ways in which a sensing arrangement can be configured in an encoding/sensing component as in FIG. 2.

FIG. 11 illustrates two alternative implementations similar to those in FIGS. 8-9, and with the same reference numerals, but with arrangement 610 on a surface of support structure 680, which could be a substrate on which photosensors are fabricated or a structure on which they are mounted after fabrication. For example, fabrication could include printing or otherwise depositing and patterning circuitry of sensing elements 612, 614, 616, 618, and 620 and also blocking material 622, with or without filters over them as described above, or by producing a longitudinal sequence of sensing elements in any other appropriate way, with some possible techniques being described below in relation to other exemplary implementations. In the implementation at left in FIG. 11, support structure 680 also operates as one side of channel portion 602, replacing light-transmissive component 630 along at least a portion of the channel. In other words, arrangement 610 is positioned on an inside channel surface similarly to filter assembly 642 in FIG. 9. In the implementation at right in FIG. 11, support structure 680 and sensing elements on it are outside of channel portion 602 separated from the outer surface of component 630 by a small gap of height g as shown. In this implementation, arrangement 610 is positioned similarly to filter assembly 644 in FIG. 9, but not directly on the outer surface of component 630. The gap between component 630 and sensing elements on support structure 680 can be maintained by spacers or other appropriate support components, and can be sufficiently large that sensing elements and support structure 680 do not interfere with anti-resonant waveguiding within channel portion 602, which can be implemented, for example, in the ways described in U.S. Pat. No. 7,386,199, entitled "Providing Light to Channels or Portions", incorporated herein by reference in its entirety.

Absorption filters that provide appropriate sensing spectra for photosensing elements, as described above in relation to FIG. 9, can be implemented in a multitude of ways. For example, rather than only two types of band pass filters that have bands for respective colors, three or more types of filters with three or more respective colors could be used. Similarly, a filter assembly can include band pass filters and other types of absorption filters as would be found in a shadow mask. Furthermore, with printed filters as described above or with other filters produced with layers of material, overlapping band pass filters could be produced, providing additional information. In addition, absorption filters could be combined with reflection filters, as described below in relation to some exemplary implementations.

Figure 12:
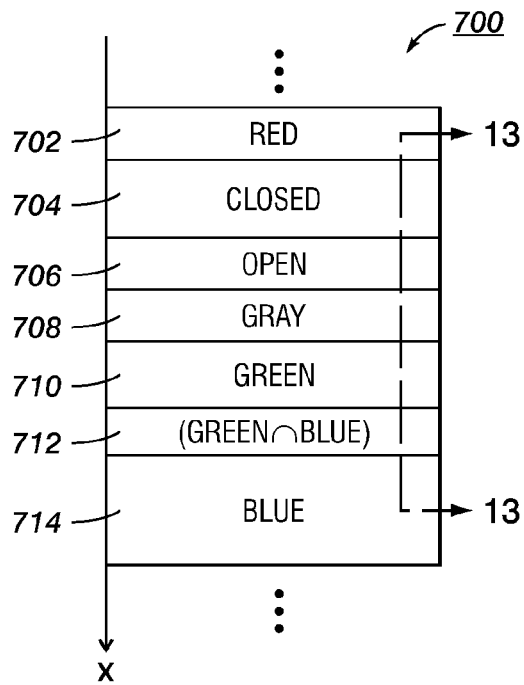
FIG. 12 is a schematic top view of another sensing arrangement that can be included in an encoding/sensing component as in FIG. 2.

Filter assembly 700 in FIG. 12 illustrates some of these variations. In the illustrated assembly, each stripe is labeled with a description of its filter criterion. Stripe 702 is a red band pass filter; stripe 704 is a closed filter, meaning that it allows no transmission; stripe 706 is an open filter, meaning that it allows full transmission; stripe 708 is a gray filter, meaning that it passes all photon energies across a range of interest, but at an intensity in between an open filter and a closed filter; stripe 710 is a green band pass filter; stripe 712 is a combined band pass filter that passes only the intersection of blue and green; and stripe 714 is a blue band pass filter. In addition, as can be seen, the widths of the stripes are random rather than periodic; although it would be possible to implement striped filters of random widths so that their boundaries are aligned with boundaries of striped discrete photosensors underneath them, this approach would face technical difficulties that might drive up cost.

Figure 13:
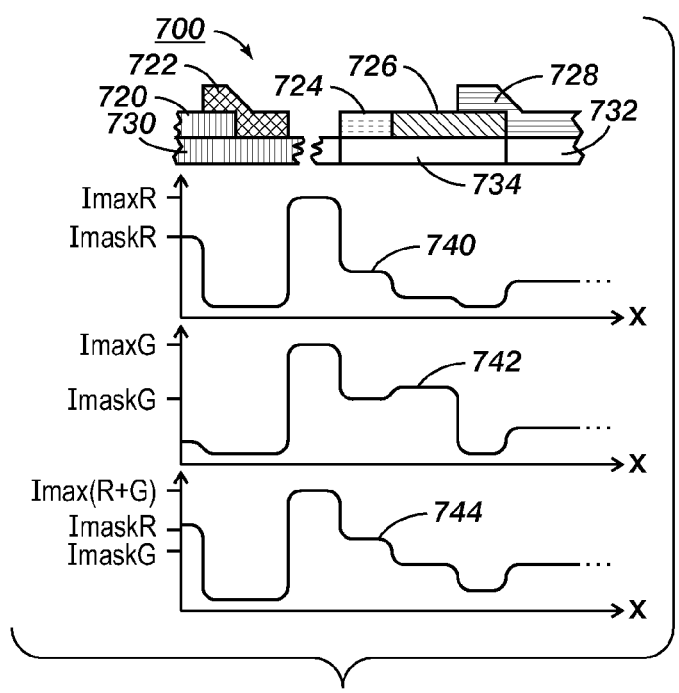
FIG. 13 is a cross-sectional view of exemplary implementations of sensing arrangements similar to that in FIG. 12, taken along the line 13-13, together with graphs of transmitted intensities.

The cross section in FIG. 13 illustrates two alternative ways of implementing filter assembly 700 in FIG. 12 using ICs with arrays that include photosensing cells. Assembly 700 itself is illustratively implemented using patterned layers of light absorbing material to produce different types of filters directly on an IC's photosensitive surface or with one or more appropriate separating layers. The implementations in FIG. 13 could, for example, be implemented by printing or otherwise depositing and patterning layers of material as described above.

In the cross section at the top of FIG. 13, filter assembly 700 includes red layer part 720, black layer part 722 overlapping layer part 720, gray layer part 724, green layer part 726, and blue layer part 728 overlapping layer part 726. Where overlaps occur, the result is the intersection of two absorption filters: the intersection of layer parts 720 and 722 is a closed filter, while the intersection of layer parts 726 and 728 is a filter with a band that is the intersection of the bands of the green and blue filters.

Under filter assembly 700, at left in FIG. 13, is a cross section of part of array 730, in which photosensing cells are sufficiently small that any feature (i.e. stripe) of assembly 700 has at least one photosensing cell or line of photosensing cells that are entirely under it and therefore will receive only a limited amount of emanating light through other features of assembly 700; for applications in which high signal-to-noise ratios are required, the maximum amount of emanating light that can be received through other features could be specified in accordance with the required ratio. This way of implementing assembly 700 on an IC avoids difficulties with alignment as described above, and can take into account relevant requirements for sampling frequencies.

Under filter assembly 700, at right in FIG. 13, is a cross section of part of array 732, in which photosensing cells are sufficiently large that each photosensing cell receives emanating light through more than one feature of assembly 700; cell 734, for example, receives emanating light through stripes 708, 710, and 712 in sequence, and therefore will provide photosensed quantities with time variation as a light-emanating object has relative motion through an encoding/sensing region relative to array 732. Although cell 734 is illustratively shown with its boundaries approximately aligned with the boundaries between stripes 706 and 708 on one side and between stripes 712 and 714 on the other, alignment might not be necessary—a cell boundary between stripe boundaries might beneficially facilitate time ordering, concatenation, or other combining into a sequence of photosensed quantities from adjacent cells.

The three graphs below the array cross sections show expected intensity signals similar to those in the graphs in FIG. 10. Curve 740 would be for a red fluorescing particle or tag, with photosensed quantities at intensity ImaskR when passing red stripe 702; curve 742 would be for a green fluorescing particle or tag, with photosensed quantities at intensity ImaskG when passing green stripe 710; and curve 744 would be for an example where object 640 is tagged both with a red and a green fluorescing particle so that curve 744 is a scaled sum of curves 740 and 742. More generally, the techniques of FIGS. 12 and 13 would make it possible to distinguish not only red, green, and blue particles and tags, but also objects tagged with combinations such as red and green, green and blue, red and blue, and red and green and blue. Each combination results in a distinguishable time varying signal that can be analyzed to obtain information about the color or colors that are emanating.

Intensity signals as described above in relation to FIG. 10 could also be obtained using an IC with an array that includes photosensing cells as in FIG. 13 rather than using an arrangement of discrete photosensors as in FIG. 10. In general, if an array is used, and photosensing cells of the array are covered with different features of a filter assembly or with different filter assemblies, it may be possible to distinguish many different types of particles concurrently based on photosensed quantities read out from the cells. The number of types of particles to be distinguished can be much larger than the number of photosensing cells in the array, since each measurable distinguishing feature can provide one axis in a principal component analysis, and multiple particles can be distinguished along each such axis. Additional techniques that can be used to track and distinguish objects are described in U.S. Patent Application Publication No. 2008/0186488, entitled "Distinguishing Objects", incorporated herein by reference in its entirety. Objects can be distinguished, for example, from their environment or background or from objects of other types; an operation "distinguishes" objects if the operation locates, selects, sorts, counts, or otherwise identifies an object or controls or directs an object according to type or separates objects or otherwise treats objects differently in some way.

Various other types of photosensors and band pass filters of other types can also be used to implement photosensing elements with filter assemblies as described in some of the exemplary implementations herein. For example, interference-based filters can have different bands similar to the bands described above in relation to FIGS. 8-13. Examples of interference-based filters are described in co-pending U.S. patent application Ser. No. 12/024,490, entitled "Transmitting/Reflecting Emanating Light with Time Variation", incorporated herein by reference in its entirety.

The configurations in FIGS. 8-13 are merely exemplary, and components could be positioned in any suitable way along a fluidic channel or other region that includes encoding/sensing regions within which objects have relative motion. A photosensing element could be positioned, for example, as at right in FIG. 11, spaced from an outer channel surface by spacers or other structures, or operating as one side of a channel as at left in FIG. 11, in which case it must be structured so that its photosensitive surfaces are not damaged or prevented from operating properly by materials in the channel and also so that it provides an appropriate boundary for fluids or other contents of the channel. Similarly, a filter assembly or other filter arrangement or other transmission structure to determine sensing spectra could be on a photosensor's photosensitive surface in any of the photosensor positions mentioned above, could be positioned in any of the ways shown in FIG. 9, or could be positioned in any other appropriate way.

Also, a wedge-shaped layer of transparent material or of a Fabry-Perot filter could have filter assemblies formed at its upper surface such as by techniques described above. In other words, in addition to having filters of the types described above, there could also be a continuously varying thickness across a filter component so that, in addition to the time-varying effects of each filter assembly, additional spectral information is contained in the encoded emanating light, and can be obtained by appropriate processing. With techniques such as this, it may be possible to measure the entire spectrum with a loss of not more than 50% (assuming full modulation) of the light, which would be advantageous in comparison with conventional linear variable filter approaches.

Figure 14:
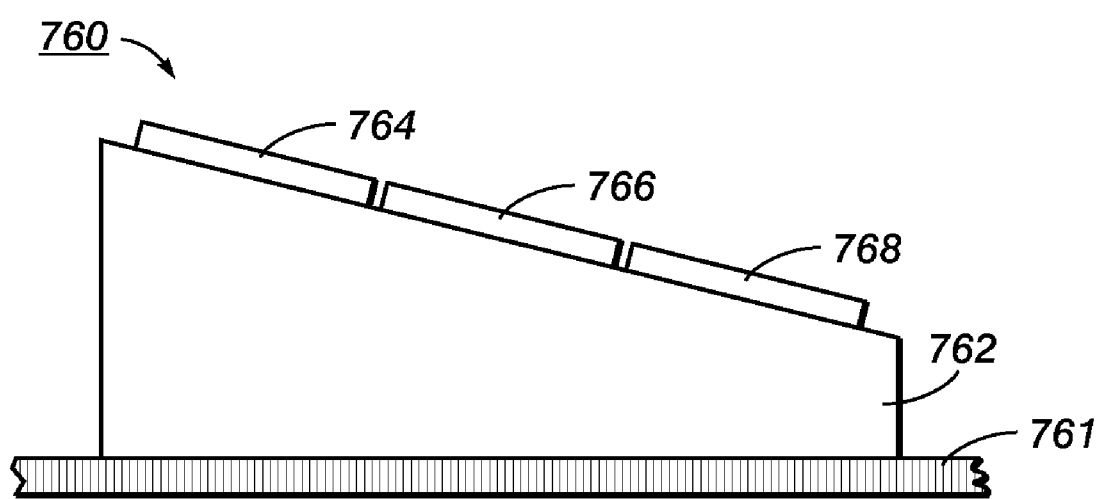
FIG. 14 is a cross-sectional view of yet another implementation of a sensing arrangement that can be included in an encoding/sensing component as in FIG. 2.

FIG. 14 illustrates an additional technique that could be used together with other filter techniques such as those described in co-pending U.S. patent application Ser. No. 12/024,490, cross-referenced above. Filter component 760 on a part of array 761 of photosensing cells includes a wedge-shaped layer of transparent material or Fabry-Perot filter, but with filter assemblies 764, 766, and 768 formed at its upper surface. In other words, in addition to having filters of the types described above, there is also a continuously varying thickness across component 760 so that, in addition to the time-varying effects of each filter assembly, additional spectral information is contained in the encoded emanating light, and can be obtained by appropriate processing of sensing results read out from photosensing cells in array 761, which are sufficiently small that they can obtain many samples along each of assemblies 764, 766, and 768. With techniques such as this, it may be possible to measure the entire spectrum with a loss of not more than 50% (assuming full modulation) of the light, which would be advantageous in comparison with conventional linear variable filter approaches.

Figure 15:
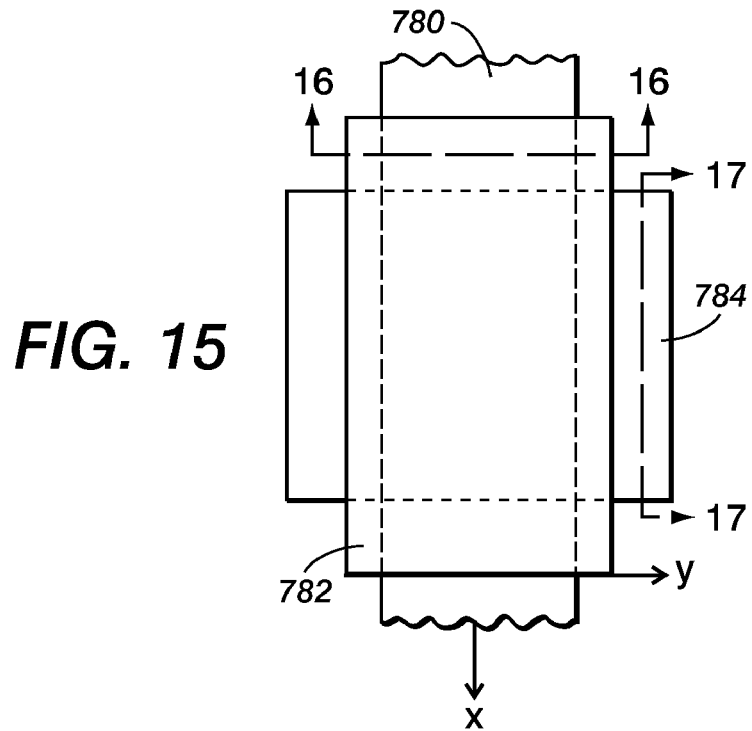
FIG. 15 is a top view of an implementation of a fluidic channel with an encoding/sensing component that can be included in an implementation with features as in FIG. 2.
Figure 16:
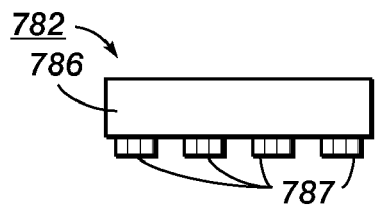
FIG. 16 is a cross-sectional view of a component in FIG. 15, taken along the line 16-16.
Figure 17:
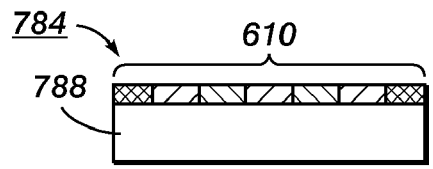
FIG. 17 is a cross-sectional view of another component in FIG. 15, taken along the line 17-17.

FIGS. 15-17 illustrate photosensing implementations in which sensing element arrangements are on opposite sides of channel 780. Sensing element arrangement 782 is illustratively on the near side of channel 780 while sensing element arrangement 784 is on the far side of channel 780. Although each arrangement could be implemented in a wide variety of different ways, to obtain information about emanating light and objects from which light emanates, FIGS. 16 and 17 illustrate an example in which arrangement 782 includes a periodic sensing pattern with periodicity in a direction transverse to channel 780, labeled the y-direction, and arrangement 784 includes a random sensing pattern that includes sensing elements with two different types of sensing spectra in a longitudinal sequence in the x-direction, though other angles between the x- and y-directions might also be useful including, in some cases, implementations in which they are parallel. In the illustrated case, sensing results from arrangement 782 include signals modulated in the y-direction, while sensing results from arrangement 784 indicate signals modulated in the x-direction. The two modulations can be used to obtain information about an object from which light is emanating.

As shown in FIG. 16, arrangement 782 can be implemented with support structure 786 on a surface of which are sensing elements 787, periodic in the y-direction; each of sensing elements 787 illustratively has a sensing spectrum that is highly responsive in a red band, but they could instead be highly responsive to any other color or could have a specific sensed intensity ratio, and could be implemented with absorption, reflection, or interference-based filters over photosensors as described above. Similarly, FIG. 17 shows an implementation of detector 784 in which support structure 788 has arrangement 610 (FIG. 8) on its surface; in addition, an appropriate periodic filter assembly, e.g. with green filters, could be superimposed on arrangement 610, or arrangement 610 could be replaced with a periodic arrangement of sensing elements with sensing spectra that are highly responsive in another band, e.g. a green band.

A wide variety of other arrangements similar to FIGS. 15-17 would be possible, and sensing results obtained from such arrangements could be used in a wide variety of ways, including those described in co-pending U.S. patent application Ser. No. 12/022,485 entitled "Obtaining Information from Time Variation of Sensing Results", incorporated herein by reference in its entirety. In the illustrated implementation, for example, the periodic signal from arrangement 782 could be constantly analyzed to obtain values indicating displacement of an object currently flowing through channel 780, which could be used to determine an appropriate time scale for correlation with the signal from arrangement 784. In another possible variation, emanating light from fluorescence could be photosensed on one side of channel 780 and emanating light due to scattering, for example, could be photosensed on the other side. If appropriate, time-varying waveforms indicated by sensing results from photosensing element arrangements on opposite sides of a channel could be compared, such as by correlation techniques.

Some of the exemplary implementations described herein involve sensing element arrangements that combine photosensed quantities in accordance with two or more concurrent sensing patterns, such as a periodic sensing pattern together with one or more non-periodic sensing patterns, such as patterns similar to some of those described above. The resulting time-varying signal after reading out and combining photosensed quantities has two or more different spatially varying patterns imposed on it. To produce such a signal, for example, a superposition of sensing patterns similar to that shown in FIG. 3 could be used.

Figure 18:
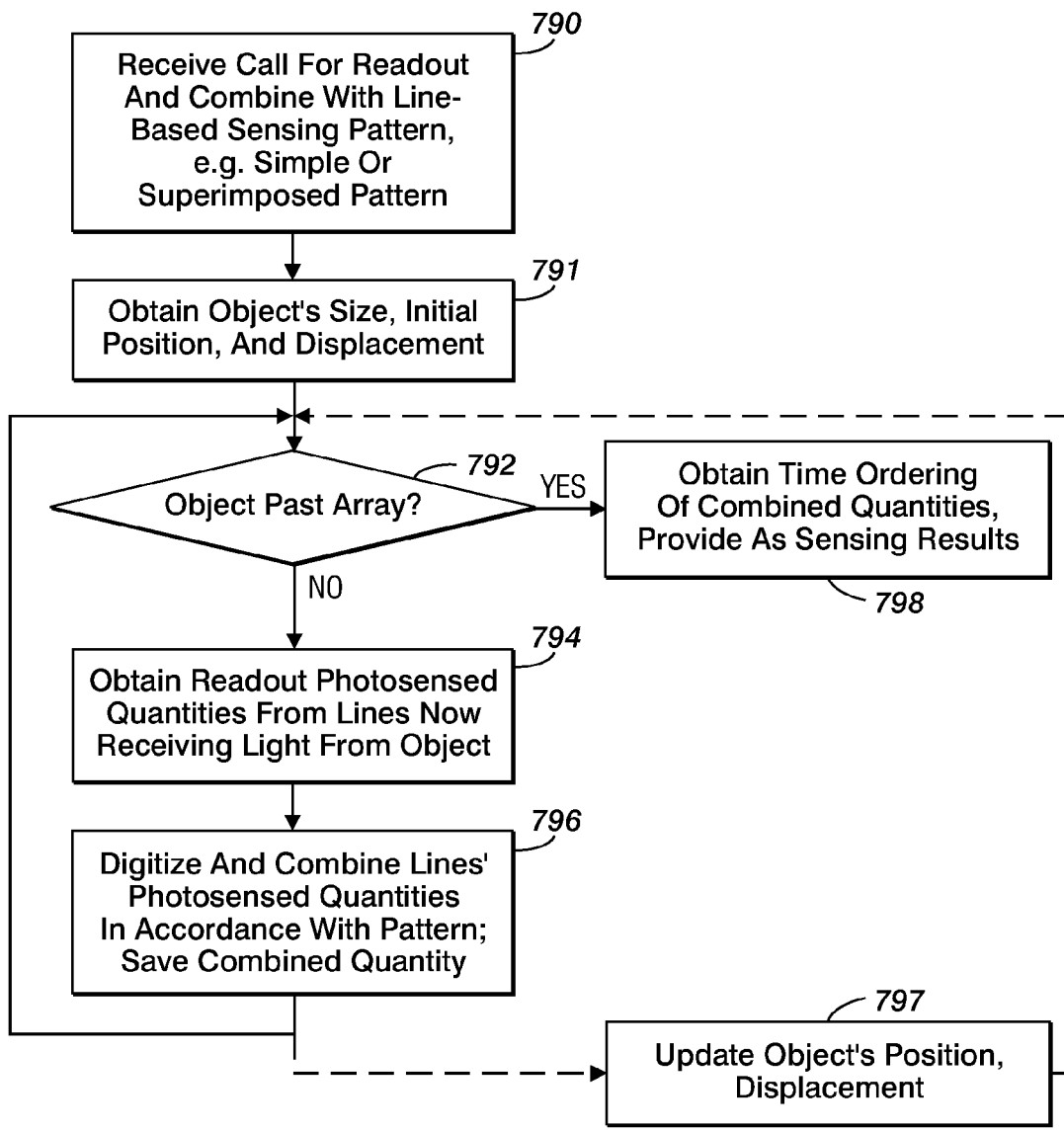
FIG. 18 is a flow chart showing specific operations in an implementation of operations in FIG. 5 with a line-based sensing pattern.

Some superpositions (or scaled superpositions) of various types of spectrum-independent photosensing patterns (e.g. patterns that are binary or, at most, intensity-dependent) can be straightforwardly obtained using IC-implemented monochromatic sensing elements with appropriate techniques for reading out and combining photosensed quantities; superpositions of spectrum-dependent photosensing patterns might also be obtained using IC-implemented multichromatic sensing elements (e.g. arrays with cells that photosense red-green-blue). FIG. 18 illustrates features of one general technique along these lines that is also an implementation of features described above in relation to FIG. 6 and which could similarly be implemented by operations of CPU 402 (FIG. 5); various other techniques could be implemented to obtain sensing results in accordance with sensing patterns that are superpositions or scaled superpositions of simpler sensing patterns.

The implementation of FIG. 18 begins with the operation in box 790 receiving a call to perform readout and combine operations; the call can include, be accompanied by, or somehow explicitly or implicitly refer to a sensing pattern to be used during the readout and combine operation. This call could originate in any of the ways described above in relation to FIG. 6, and could result from a trigger signal or in another appropriate way, such as from a call that is provided periodically. As shown, however, the sensing pattern is "line-based", meaning that readout can be performed in accordance with the sensing pattern by reading out lines of an array of photosensing cells; in effect, the sensing pattern can be specified by specifying sensing characteristics for a sequence of lines, whether by specifying a repeating subsequence as in a periodic pattern, a single non-repeating sequence as in a non-periodic pattern, another type of sequence or subsequence, or even values for generating a sequence algorithmically or otherwise. In general, a line-based sensing pattern can be obtained that approximates another type of sensing pattern in which variation is predominantly in the longitudinal direction, e.g. a sensing pattern with parallel stripes, each having respective sensing characteristics and a respective width in the longitudinal direction; for complex patterns, all variations that are non-longitudinal could be ignored, and a respective digital value could be obtained for each position in the longitudinal direction, approximating the longitudinal variation to a desired level of resolution. The sensing pattern could be a "simple" pattern, in the sense that it is not a superposition of simpler patterns, such as a simple periodic or non-periodic pattern; the sensing pattern could also, however, be a superposition or scaled superposition of simpler patterns, e.g. if the simpler patterns are "parallel", meaning that the simpler patterns are all line-based patterns with lines sufficiently parallel that they can therefore be combined into a single line-based pattern, possibly after appropriate scaling of one or more patterns. When a line-based sensing pattern is obtained as a series of digital values, its relation to a particular array can also be specified by indicating the number of lines of the array that are included in each digital value of the pattern; this approach also makes it possible to use arrays with different but related cell sizes to implement a given sensing pattern at the same actual scale.

The operation in box 791 then prepares for readout, and can in general be implemented similarly to box 452 (FIG. 6). In particular, the operation in box 791 can obtain an object's size, initial position, and displacement, e.g. relative speed, and these values can later be used to identify lines of a photosensing array that are receiving emanating light from the object as it subsequently has relative motion within an encoding/sensing region from which light emanates to the array. The operation in box 791 can include appropriate signals to and from one or more of ICs 412 through 414 through IC I/O 410 (FIG. 5), and can also include appropriate signals to and from other devices through device I/O 420 (FIG. 5).

After the operation in box 791, the implementation of FIG. 18 performs a series of iterations, each of which begins with the operation in box 792, which determines whether the object has gone out of the encoding/sensing region, such as based on the object's current position. Unless the object has left the encoding/sensing region, the next iteration is performed, obtaining combined quantities using photosensed quantities read out from lines receiving emanating light from the object. Assuming sufficient separation between objects, similar iterations could be concurrently but independently performed for more than one object, but the implementation of FIG. 18 relates to only one such object in an encoding/sensing region. In general, the operations in each iteration are similar to operations described above in relation to boxes 472, 474, 480, and 482 (FIG. 6), and could accordingly be implemented as appropriate for the readout type of the array, e.g. CCD-type readout, CMOS-type readout, or other, with appropriate signals to and from one or more of ICs 412 through 414 through IC I/O 410 (FIG. 5).

Each iteration begins with the operation in box 794, which obtains readout photosensed quantities from lines of photosensing cells that are receiving emanating light from the object at the time the iteration is performed; the term "readout photosensed quantities" is used herein to refer to photosensed quantities that have been read out. The operation in box 794 could be implemented in many different ways: At one extreme, all lines of the array could be read out as in box 472 (FIG. 6) and then only readout photosensed quantities could be selected that are from lines now receiving emanating light from the object; at another extreme, lines now receiving emanating light could first be identified and then only the identified lines could be consecutively selected and read out as in box 480 (FIG. 6); and other approaches could be intermediate between these extremes. In general, the operation in box 794 somehow identifies lines now receiving emanating light from the object, such as based on object size, position, displacement, and other information from box 791, possibly updated as described below. The operation in box 794 thus results in readout photosensed quantities from the identified lines being available for subsequent operations, which can be performed in real time or later, after read out is completed. In any case, readout photosensed quantities can be stored in memory 408 (FIG. 5) for further processing.

The operation in box 796 operates on readout photosensed quantities from box 794, digitizing and combining them in accordance with the sensing pattern from box 790, and then saving the resulting combined quantities in memory 408 (FIG. 5) or in another appropriate way so that they can be provided as sensing results, as described below. In the case of CCD-type readout, for example, readout photosensed quantities can be digitized as they are shifted out of the array and the digitized quantities for each line can be added to obtain a respective sum for the line; then, when the lines now receiving emanating light are identified, the respective sums of those lines can be similarly combined in accordance with the sensing pattern from box 790, such as by binning as in box 474 (FIG. 6) and/or performing other operations as appropriate. Similarly, in the case of CMOS-type readout, the lines now receiving emanating light can first be identified and then those lines can be read out consecutively in parallel into sample and hold circuitry (not shown), with each line's readout photosensed quantities then being similarly being digitized and added to obtain a respective sum for the line; then, the sums can be combined in accordance with the sensing pattern from box 790, such as by adding as in box 482 (FIG. 6) and/or performing other operations as appropriate.

The operation in box 796 can take into account various features of the sensing pattern from box 790. For example, when emanating light is being received on both sides of a boundary between stripes within the sensing pattern, photosensing results could simply be discarded; in a more complex implementation, lines on each side of the boundary could be separately binned or added and saved for subsequent operations. Where a sensing pattern is intensity-dependent, photosensed quantities could be scaled in accordance with the specified intensity of each stripe of the pattern at any appropriate time, such as by analog operations immediately when read out or by digital operations after being digitized, after being combined for a line, or after being combined for a group of lines within the stripe. Similarly, where a sensing pattern is spectrum-dependent and readout photosensed quantities include spectral information such as by being in an RGB pattern, readout photosensed quantities could be selected for binning or adding in accordance with the specified spectrum of each stripe of the pattern.

After the operation in box 796, the operation in box 797 can be optionally performed as indicated by the dashed lines to and from box 797. This operation updates information about the object's position and displacement, making it possible to more accurately identify lines that are receiving emanating light from the object in the next iteration. This operation could be performed in every iteration or it might never be performed; also, each iteration could include a decision whether to perform this operation based, e.g., on photosensed quantities read out and combined in boxes 794 and 796 or on other information obtained in the current iteration.

When the operation in box 792 determines that the object is past the array, i.e. has left the encoding/sensing region, the operation in box 798 orders the combined quantities from iterations of box 796 and provides the resulting time-ordered combined quantities as sensing results that indicate one or more time-varying waveforms, such as to external circuitry through external I/O 406 or by storing the sensing results in appropriate data structures in memory 408 or in one of devices 422 through 424 by appropriate signals to device I/O 420 (FIG. 5). The time ordering operation in box 798 can include various appropriate adjustments to obtain improved sensing results. For example, where emanating light from an object is approximately constant across each stripe of a sensing pattern, the combined quantities from iterations of box 796 that include values from that stripe can be used to obtain a single value that is provided for each frame of that stripe, where the term "frame" is used herein to refer to a unit of time for which one value or one set of concurrent values is provided in the time-ordered combined quantities; if the iterations occur with a constant period, each frame could have the same proportionality relationship to the length of each iteration, with, e.g., j iterations per frame or with k frames per iteration. More generally, the time-ordered combined quantities that form the sensing results can be time scaled or otherwise adjusted in any appropriate way so that they accurately reflect light emanating from the object as a function of time.

If the sensing pattern from box 790 is purely binary, it can be treated, in effect, as two complementary patterns that can both be applied in operations in box 796; in other words, line groups that are on in the sensing pattern would be binned together in a first binning operation, while line groups that are off would be omitted, while line groups that are off in the sensing pattern would be binned together in a second binning operation, while line groups that are on would be omitted, with the result that all photosensed quantities are binned in one of the two operations. As a result, the operation in box 798 can produce two complementary sequences of values, one for each of the complementary patterns, and appropriate further operations can be performed to combine the complementary sequences into a single combined sequence of values, such as to improve signal-to-noise ratio due to redundant information in the complementary sequences. This technique may be especially useful with rapid CCD-type readout in which all lines are being read out in any case, so that the only additional operations are the digitization and binning after each shifting operation; high quality CCD-type readout devices are currently available with peak quantum efficiency exceeding 90% and with sampling rates as fast as 30 MHz.

Some techniques as in FIG. 18 can be implemented without filters or masks, because binning or other appropriate operations on photosensed quantities from selected lines takes the place of masking. More flexible techniques could be implemented by saving each line's respective combined quantity in box 796, and then further combining those quantities in accordance with any appropriate number of sensing patterns in box 798 prior to time ordering; in a particularly useful example, the respective quantities of lines could first be binned or otherwise selected and/or combined in accordance both with a periodic pattern (e.g. every nth line) and a random, chirp, or other non-periodic pattern—the periodic sensing results could be used to obtain speed or other displacement information about an object, and the non-periodic sensing results (from binning or from a non-periodic filter as in FIG. 13) could be used, together with time-scaled comparison based on the displacement information, to obtain information about the object's position or type, such as with techniques as described in co-pending U.S. patent application Ser. No. 12/022,485, entitled "Obtaining Information from Time Variation of Sensing Results", incorporated herein by reference in its entirety. Also, since it is not necessary to optimize, make, and align a mask for a specific cell diameter or other object size or characteristic, it is possible to combine the respective combined quantities of groups of lines as appropriate for different object sizes or other characteristics after the lines' combined quantities have been obtained and saved; in effect, a pre-analysis operation could be performed on the lines' combined quantities to extract information about an object, e.g. by binning in accordance with a chirp pattern or a random pattern with small feature size or even with a staircase periodic pattern. After pre-analysis, a technique according to these variations could branch based on the extracted information, such as by binning the combined quantities as appropriate for the object size obtained in pre-analysis. It might be possible to implemented variations of the technique in FIG. 18 to efficiently replace techniques previously used for detecting object size and position, such as Mie scattering and so forth.

While the implementation of FIG. 18 is relatively general, it may not be optimal or otherwise appropriate in all situations. Similar features of sensing patterns could be implemented in other ways, such as with filters over photosensing arrangements, examples of which are described above in relation to FIGS. 9 and 12-14. Furthermore, it might be advantageous in some cases to provide a filter arrangement that includes an actual superposition of filter patterns over a suitable photosensing element arrangement; such a filter arrangement could be obtained using a radial sequence or "stack" of filters or a "stack-equivalent" filter; techniques for producing stack-equivalent filters are described in co-pending U.S. patent application Ser. No. 12/025,394, entitled "Producing Filters with Combined Transmission and/or Reflection Functions", incorporated herein by reference in its entirety. Within a stack of filters or a stack-equivalent filter, for example, one layer could be a template layer with an appropriate pattern to produce a template signal, while another layer could be a periodic layer with an appropriate pattern to produce the periodic signal; each of the template layer and periodic layer could have rectangles or other closed polygons of zero opacity surrounded by regions with opacity 0.5.

Figure 19:
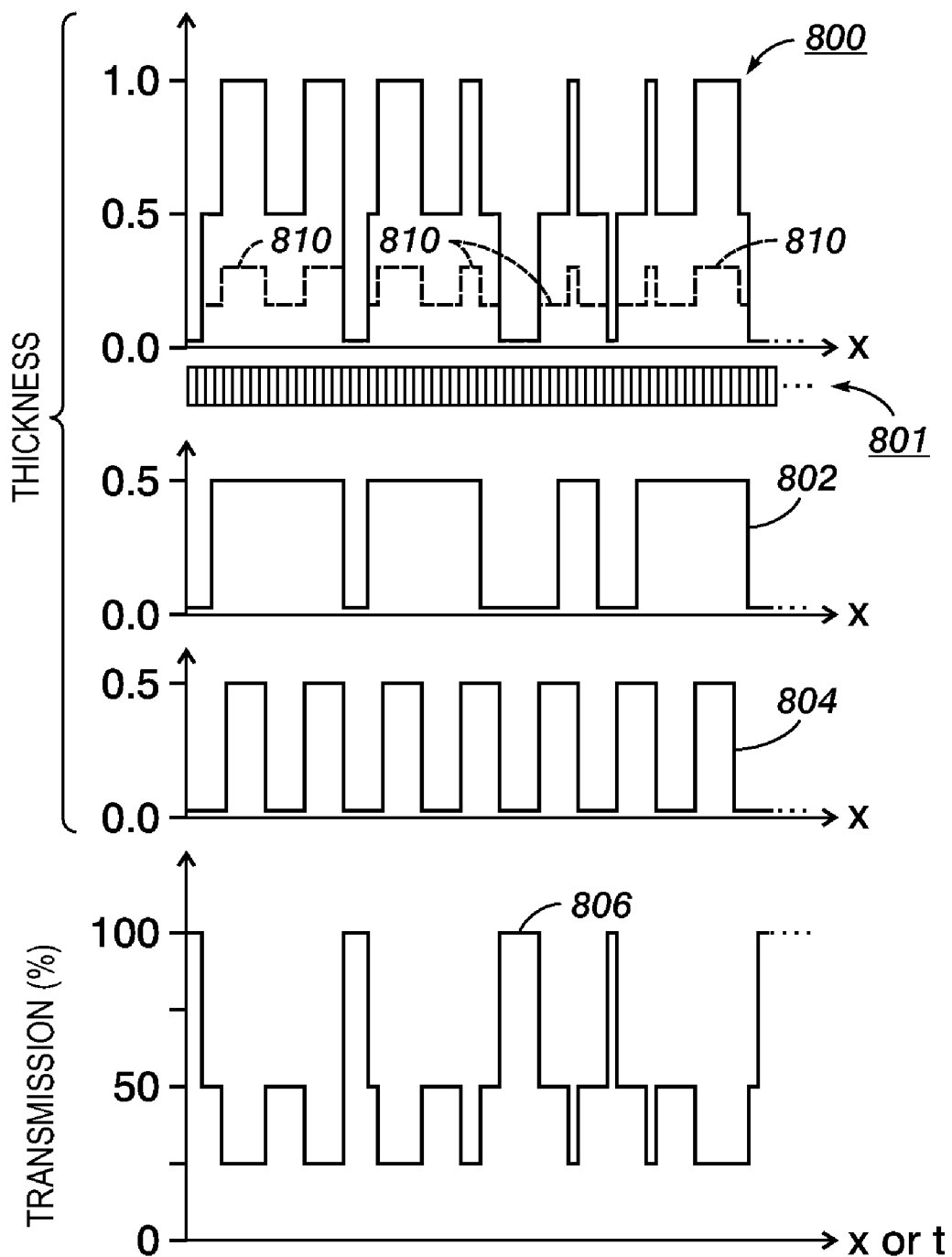
FIG. 19 includes a set of graphs showing discrete sensing elements and array-based approximations of discrete sensing elements as a function of position in an x-direction and showing sensing results as a function of position in the x-direction or as a function of time t.
Figure 20:
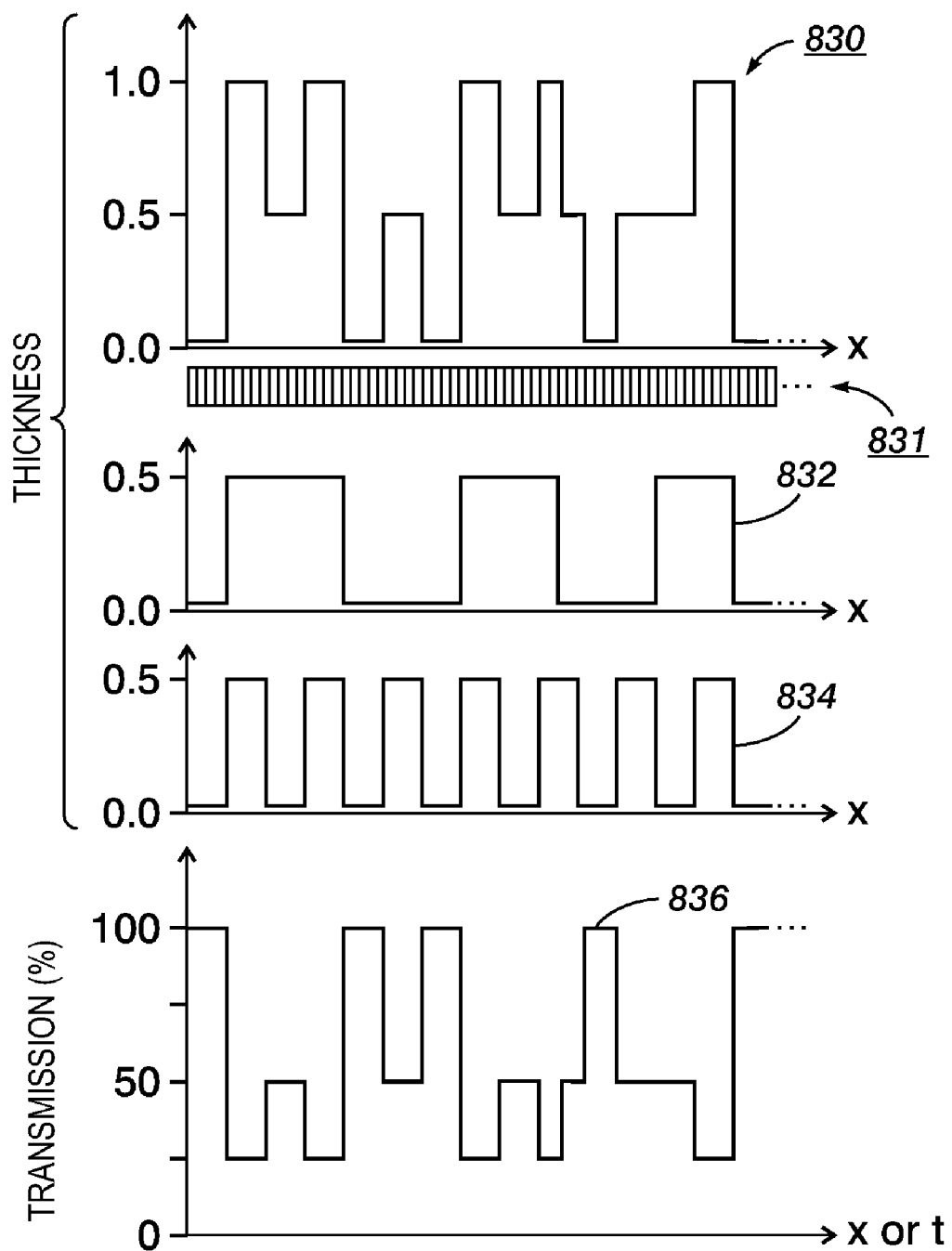
FIG. 20 includes another set of graphs showing discrete sensing elements and array-based approximations of discrete sensing elements as a function of position in an x-direction and showing sensing results as a function of position in the x-direction or as a function of time t.

FIGS. 19 and 20 illustrate an alternative approach that can be used with reflective gray scale stack-equivalent filters equivalent to a desired radial sequence or stack of filters, over a photosensing element arrangement such as an array that includes photosensing cells. To obtain filters as in FIGS. 19 and 20, thickness definitions of two filter layers can be overlaid using software tools and the thicknesses of overlapping regions can be added, resulting in regions with thicknesses of 0, 0.5, and 1 in the example given above; the two filter layers could both be oriented with variation in the same direction as in FIGS. 19 and 20, similar to the techniques of FIGS. 8 and 12, or could be oriented with variation in different directions, e.g. orthogonal to each other. For implementations in which layer thickness does not appropriately define or determine the desired equivalent filter's structure or its optical variation, the techniques in FIGS. 19 and 20 could be modified to first overlay optical feature definitions of the filters in which regions have defined optical feature values that determine the desired variation, thus obtaining an optical feature definition of the desired equivalent filter; the optical feature definition could then be converted to a layout-type description of the equivalent filter in which each region has a defined optical thickness or other characteristic that can be produced to provide the region's value for the optical feature.

The techniques of FIGS. 19 and 20 take advantage of the fact that, in general, superpositions of filters are commutative, in the sense that the resulting transmission or reflection function is the same regardless of the order in which filters are superimposed. There are, of course, exceptions, such as where interference effects can occur if filters are in a specific order, or where alignment or other relationship of filter features can result in loss of different information depending on the order of the filters. Where, however, superpositions of filters are commutative, a filter that is equivalent to a superposition of filters can also be used to implement the equivalent of a superposition or scaled superposition of simpler sensing patterns; more specifically, within appropriate constraints, each simpler sensing pattern can be used to obtain a respective equivalent filter pattern, and the equivalent filter patterns can then be combined by superposition or scaled superposition to obtain a combined filter pattern that is approximately equivalent to the combined sensing pattern.

If the equivalent filter definition of the combined sensing pattern is a thickness definition to produce a purely transmissive/reflective filter with no color variation or other spectral dependence, and if partial etching can be performed, an equivalent filter that approximates the equivalent filter definition can be constructed by first depositing a highly reflective material, such as chromium, over the entire filter assembly, and by then partially etching the reflective material away in regions with thickness 0 or 0.5 to an appropriate extent, leaving a thin, partially transmitting layer, after which the remaining reflective material can be etched away in regions with thickness of 0. Where partial etching is unreliable, other techniques may be used, such as by depositing a first patterned layer of thickness 0.5 with any suitable patterning technique, then depositing over it a second patterned layer of thickness 0.5 that is patterned without etching, such as with liftoff or other patterning techniques that do not require etching. Furthermore, similar techniques might be applied to produce layered filter structures that include DBRs of varying transmission/reflectivity and/or cavities of varying optical thickness; variation in cavity thickness could result from any appropriate combination of thickness variation and refractive index variation, produced with any appropriate techniques.

Filter assembly 800 in FIG. 19 is equivalent to the combination of a random filter and a periodic filter, superimposed one on the other and positioned over a sensing element arrangement, illustratively array 801 of photosensing cells. Curve 802 shows the shape of the random filter, while curve 804 shows the shape of the periodic filter; as can be seen, the random and periodic filters both have only two thickness levels, either 0 or 0.5, but filter assembly 800 has three thickness levels, corresponding to 0, 0.5, and 1. Curve 806 shows a resulting transmission function. Emanating light passing through filter assembly 800 includes both displacement and position information about an object from which it emanates, and allows time-scaling techniques to extract that information provided that photosensing cells in array 801 are sufficiently small relative to the minimum feature size (MFS) of filter 800 to provide adequate resolution.

The technique illustrated in FIG. 19 can be adjusted as suggested by dashed lines 810 within filter assembly 800. In other words, total light output can be changed by scaling the amplitude of the thickness levels: rather than 0, 0.5, and 1, for example, thickness levels of 0, 0.2, and 0.4 could be used, allowing greater light transmission. It may be necessary, however, to make a tradeoff between greater light output, and therefore total signal intensity, on the one hand, and greater light modulation on the other—greater light modulation may facilitate calculation of displacement and position within a given observation region. The mask suggested by dashed lines 810 emphasizes total light output because it has reduced thickness and, conversely, increased transmission, with a thickness of 0 being equivalent to transmission of 1 and vice versa. The scaling suggested by dashed lines 810 may require great precision: the x-direction scale of features in assembly 800 may be as great as 10 µm, while a useful thickness may be as thin as 10 nm of chromium.

Similarly, filter assembly 830 on array 831 in FIG. 20 is equivalent to the combination of a chirp filter represented by curve 832 and a periodic filter represented by curve 834. A combination of chirp and periodic filters can make it possible to more efficiently extract displacement and position information about objects that may have different speeds. Curve 836 shows a resulting transmission function, which allows information extraction.

A stack-equivalent filter assembly as in FIGS. 19 and 20 can in some cases have a smaller MFS than either of the simpler non-uniform filters or their counterpart sensing patterns. Loss of resolution can occur for light emanating from objects approximately as large as the MFS.

Figure 21:
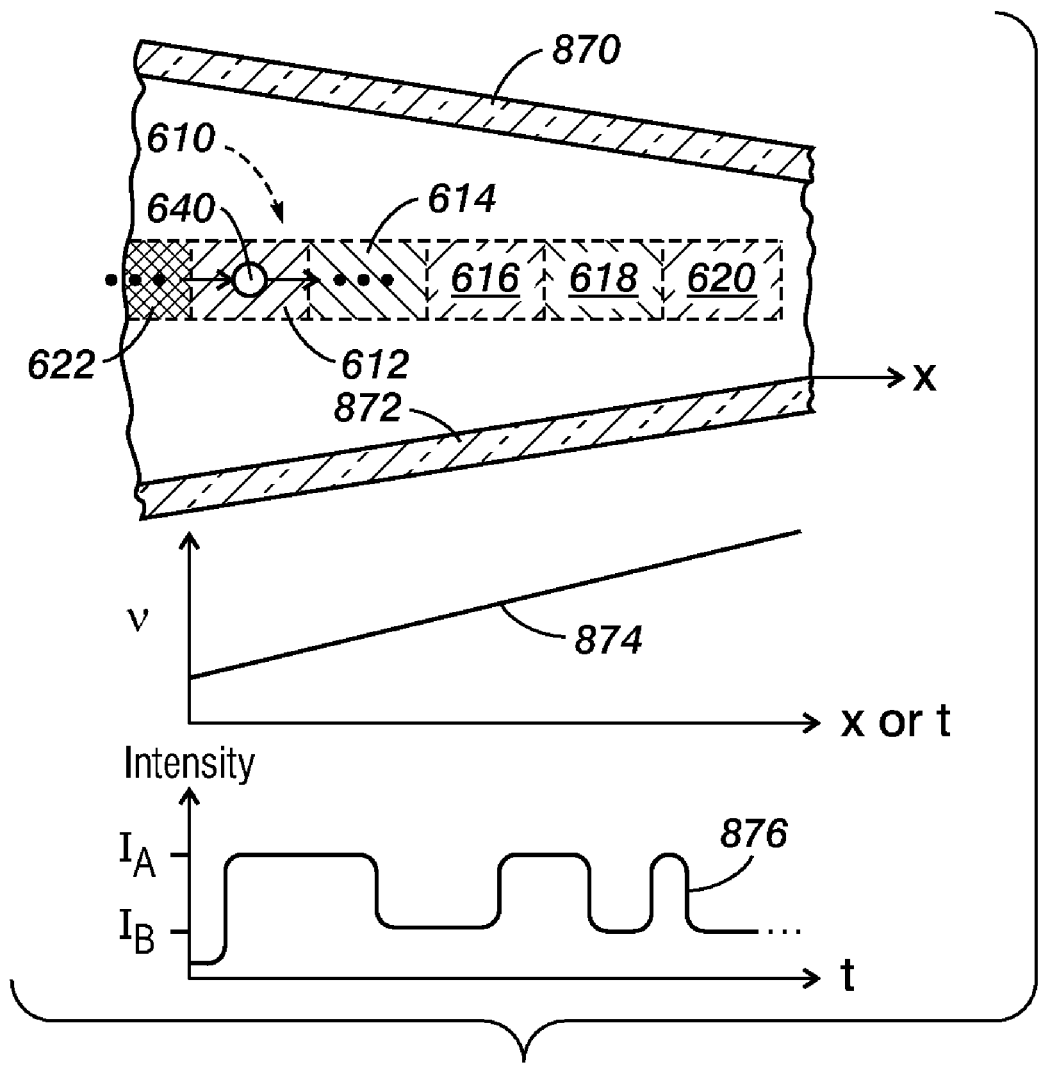
FIG. 21 is a partially schematic cross-sectional view showing a displacement control arrangement that can be included in an encoding/sensing component as in FIG. 2 and that includes shaped boundaries, together with graphs showing velocity of an object and also showing exemplary sensing results as a function of time.
Figure 22:
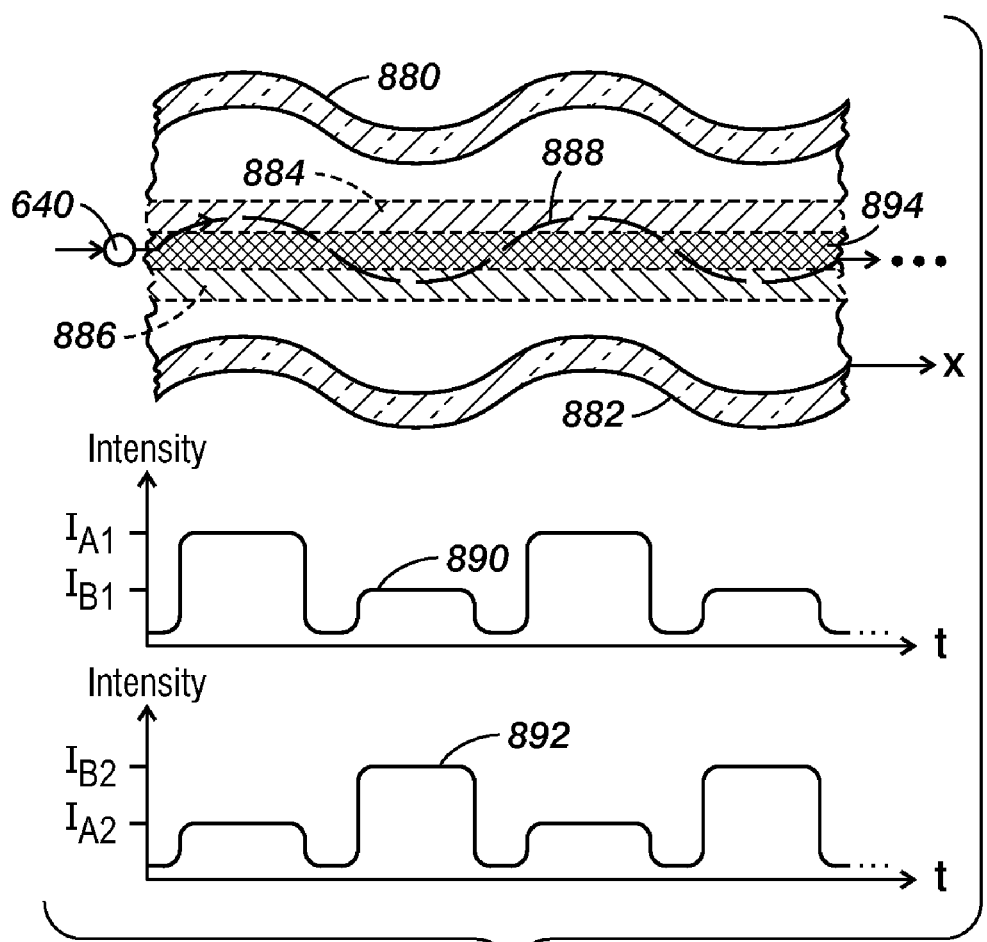
FIG. 22 is a cross-sectional view of another displacement control arrangement that can be included in an encoding/sensing component as in FIG. 2, together with a graph showing exemplary sensing results for exemplary types of objects.
Figure 23:
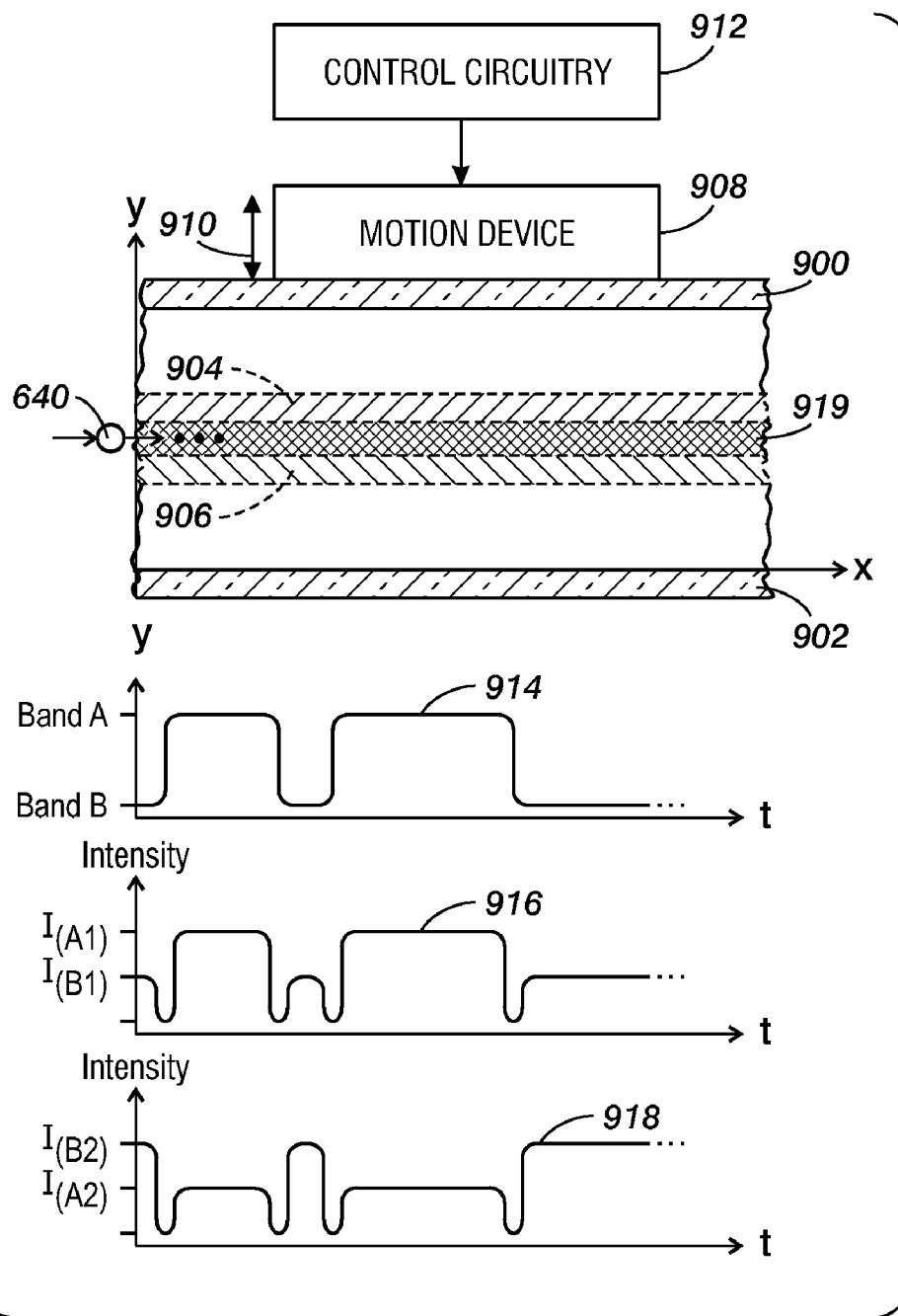
FIG. 23 is a partially schematic cross-sectional view of another displacement control arrangement that can be included in an encoding/sensing component as in FIG. 2, together with a graph showing displacement as a function of time and graphs showing sensing results as a function of time for exemplary types of objects.

In addition to various techniques employing filter arrangements, displacement control techniques can also be used to obtain desired sensing patterns in some situations. FIGS. 21-23 illustrate examples in which laminar flow can produce non-uniform displacement or can be modified in other ways.

FIG. 21, which could be taken along a line through a channel similar to that in FIG. 11, shows wall-like parts 870 and 872 with linearly decreasing distance between them. As a result, as object 640 passes along sensing element arrangement 610 (with sensing elements 612, 614, 616, 618, and 620 illustratively periodic rather than random as in FIG. 11), its velocity increases linearly as indicated by curve 874, either as a function of position or of time. Therefore, rather than a periodic time-varying signal, the resulting time-varying signal is chirped, meaning that the periods decrease linearly due to change in velocity of object 640 due to change in the flow speed of fluid in the channel resulting from the changing channel dimensions. Curve 876 illustrates how the resulting chirped signal, which can be obtained by appropriately reading out and combining photosensed quantities from arrangement 610, has intensity I(A) along elements 612, 616, and 620, and intensity I(B) along elements 614 and 618. As can be seen, the duration of the signal along each successive sensing element is shorter than along the preceding element, resulting in the chirped pattern. For the sake of illustration, the linear decrease in transition time is exaggerated in curve 876 in comparison to the narrowing of the channel.

The technique in FIG. 21 is only one of a variety of ways of producing a chirped time-varying signal using displacement control, and various other techniques could be used. For example, more complex flow speed distributions could be obtained by modifying the channel walls in other ways or by providing devices that change the flow speed or flow pattern within the channel, any of which would produce more complex time-varying signals from different objects.

FIG. 22 illustrates, on the other hand, how relatively simple time-varying signals could be produced using more complicated techniques. In general, such techniques assume that geometry of a channel directs flow of object 640 in a defined manner such as periodic, chirped, or random, past a sequence of sensing elements, such as with different spectral-dependence. This allows redirection of particle flow past a simpler sensing pattern, and may be advantageous in cases where it is easier to redirect particle flow to produce a desired time variation of emanating light than it would be to produce a sensing pattern to produce the same time variation; for example, it might be easier to change channel wall shapes than to produce a desired sensing element arrangement. In other cases, on the other hand, it might be advantageous to obtain more abrupt or rapid signal transitions with a well-defined sensing element arrangement. In addition to the techniques described below, which involve shaping or moving walls, an object's flow within a channel could also be redirected by other techniques; an electrically charged object such as a particle, for example, could be redirected by electrical field variations. In general, however, the Reynolds number in typical microfluidic and nanofluidic implementations are so small that laminar flow conditions are, as a practical matter, always present.

In the example in FIG. 22, wall-like parts 880 and 882 are parallel but each of them is shaped like a sinusoidal wave, resulting in a sinusoidal flow pattern in the channel between them. Sensing elements 884 and 886 are each homogeneous but have different sensing spectra that respond strongly to different bands, illustratively labeled "A" and "B". As object 640 follows sinusoidal path 888, it moves back and forth between elements 884 and 886, passing through a small gap between them twice during each period. Curves 890 and 892 illustrate exemplary time-varying signals that could result from an object having relative motion along path 888, after appropriate readout and combining of photosensed quantities from elements 884 and 886. Curve 890 illustrates an example of an object of a type with a spectrum similar to band A but different from band B, while curve 862 illustrates an example of an object of a type with a spectrum similar to band B and different from band A. As a result, the curves are somewhat complementary, although each curve goes to approximately 0 while path 888 is crossing stripe 894 of blocking material between elements 884 and 886. Blocking material could also be provided outside elements 884 and 886.

Wall-like parts 900 and 902 in FIG. 23 are substantially straight and parallel, with sensing elements 904 and 906 between them, similar to elements 884 and 886 in FIG. 22. Motion device 908, which could be an electrically controlled device such as a solenoid or motor-driven piston, produces lateral relative motion between object 640 and stripe-like elements 904 and 906, as indicated by bi-directional arrow 910. Control circuitry 912 provides signals to control operation of motion device 908, which need not be periodic, but could take any appropriate pattern, resulting in arbitrary time-varying signals with features indicating different types of objects. An alternative would be to move elements 904 and 906; more generally, any combination of relative motions between walls 900 and 902 on the one hand and elements 904 and 906 on the other could produce movement as indicated by bi-directional arrow 910. Furthermore, additional variations could be produced by changing fluid flow within the channel so that the speed or other displacement of object 640 changes as a function of time relative to the other movements. Motion device 908 could be set up to produce variations in response to trigger signals indicating incoming objects.

Curve 914 illustrates movement of object 640 in the y-direction between element 904, which responds strongly in a band labeled "Band A", and element 906, which responds strongly in a band labeled "Band B". As illustrated, object 640 spends different lengths of time along each sensing element and can spend a random amount of time along each sensing element, resulting in a random excitation pattern. Curves 916 and 918 illustrate exemplary time-varying signals that could be produced by the technique of FIG. 23 after appropriately reading out and combining photosensed quantities from elements 904 and 906. One type of object has a spectrum more similar to Band A of element 904, as illustrated by curve 916, while the other has a spectrum more similar to Band B of element 906, as illustrated by curve 918. As each object has relative motion between elements 904 and 906, it passes over stripe 919 of blocking material between them, resulting in a brief interruption of the emanating light, so that each curve goes briefly to 0. In curve 916, the intensity along element 904 is I(A1), while the intensity along element 906 is I(B1), a lower value. Conversely, curve 918 illustrates that the intensity is higher along element 906, at intensity I(B2), and lower along element 904, at intensity I(A2). The two curves are, in general, complementary, except for times when they are passing stripe 919 between element 904 and 906; object 640 can be moved instantaneously between Band A and Band B, moving very quickly across stripe 919, so that the times in which it is passing stripe 919 are very brief.

Figure 24:
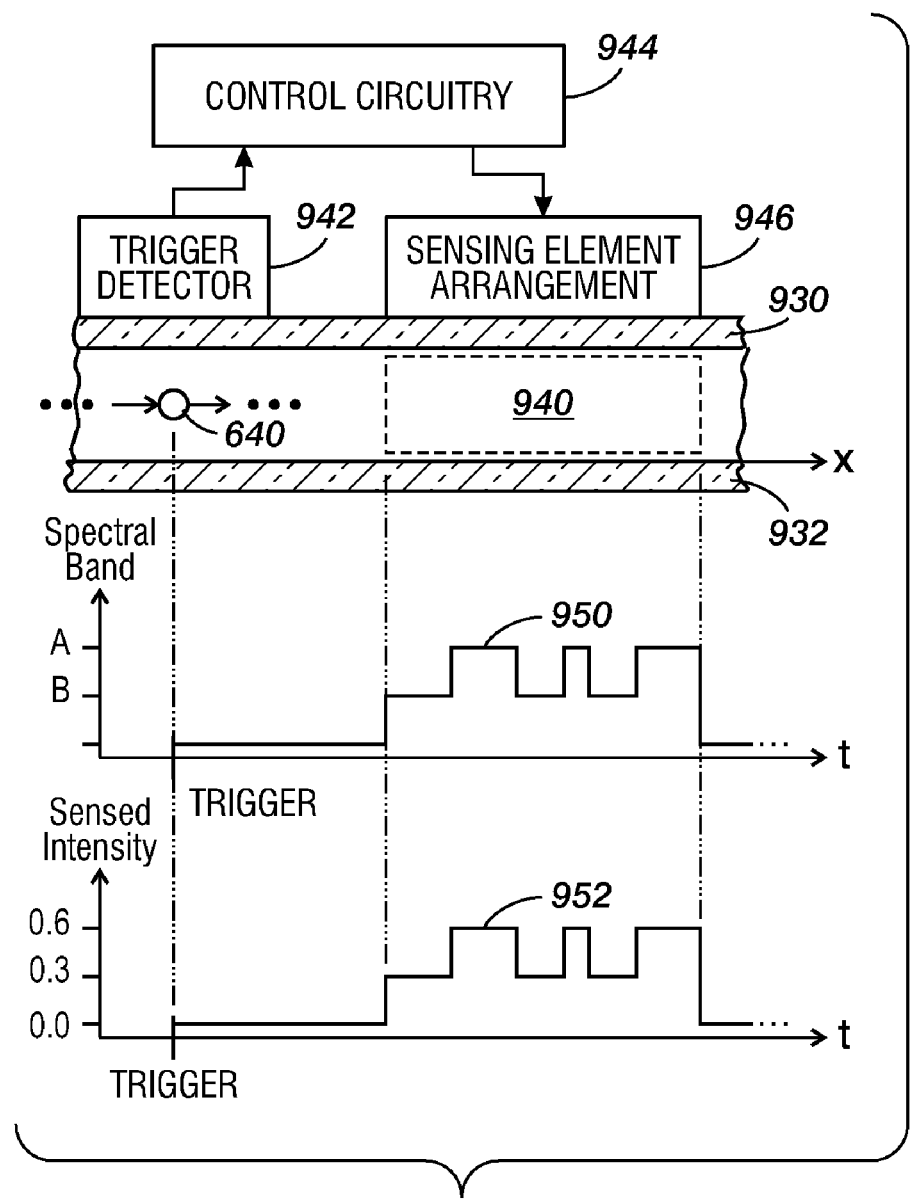
FIG. 24 is a partially schematic cross-sectional view of another sensing component that can be included in the encoding/sensing component as in FIG. 2, together with a graph showing sensing results as a function of time.

FIG. 24 illustrates a technique in which time-varying signals resulting from one or more sensing patterns can be produced with relatively precise timing based on position of an object having relative motion within an encoding/sensing region relative to an arrangement that includes the sensing pattern(s). As object 640 is carried by laminar flow through the channel between wall-like parts 930 and 932 toward encoding/sensing region 940, it passes trigger detector 942. In response to relative motion of object 640 into its trigger detection region, detector 942 provides a trigger signal to control circuitry 944, precisely indicating position of object 640 at the time of the trigger signal. Control circuitry 944 can then provide appropriately timed control signals to sensing element arrangement 946 based on position of object 640, such as signals to obtain readout in accordance with the sensing pattern(s) in one of the ways described above. Trigger detector 942 could be implemented, for example, as described in co-pending U.S. Pat. No. 7,358,476, entitled "Sensing Photons From Objects in Channels", and in co-pending U.S. patent application Ser. No. 12/337,771, entitled "Obtaining Sensing Results and/or Data in Response to Object Detection", both incorporated herein by reference in their entireties.

Curve 950 in FIG. 24 illustrates one example of how sensing results could vary over time due to spectral-dependence of arrangement 946, with some sensing elements responding strongly to a spectral band labeled as "A" and others responding strongly to a spectral band labeled as "B". As shown, elements that respond strongly to bands "A" and "B" alternate in a random sensing pattern, although such elements could instead be configured in a periodic or chirp pattern rather than in a random pattern as shown, and could be read out in any appropriate pattern if arrangement 946 is IC-implemented. In general, bands A and B could be non-binary spectral bands, or could alternatively be black and white, in which case one band is broadband (white) and the other is off (black). Also, the illustrated technique could be implemented with more than two different spectral bands.

Curve 952 illustrates another example, in which sensing results vary over time due to intensity-dependence of arrangement 946, with some sensing elements having greater sensed intensity levels than others, the resulting photosensed quantities having magnitude levels illustratively labeled 0.3 and 0.6 to indicate that they are between minimum sensed intensity of zero (i.e., black or off) and maximum sensed intensity of 1.0 (i.e., white or on). Different intermediate intensities could be provided in a similar manner with sensing elements with other intermediate sensed intensity levels.

In general, accuracy of the technique of FIG. 24 depends on obtaining trigger signals that accurately indicate position of object 640, such as from a Coulter counter or from a backward- or forward-scattered signal, so that time variations are correlated to object positions during readout of photosensed quantities; accuracy can also depend on the presence of only one object in encoding/sensing region 940 at any given time. The trigger signal from detector 942 can provide additional information about object 640, such as particle size, and this information can be used by control circuitry 944 to select a specific sensing pattern for readout, such as to optimize information encoded in sensing results; for example, control circuitry 944 could scale the longitudinal widths of sensing pattern stripes that are binned or otherwise combined, based on the dimension of object 640.

Figure 25:
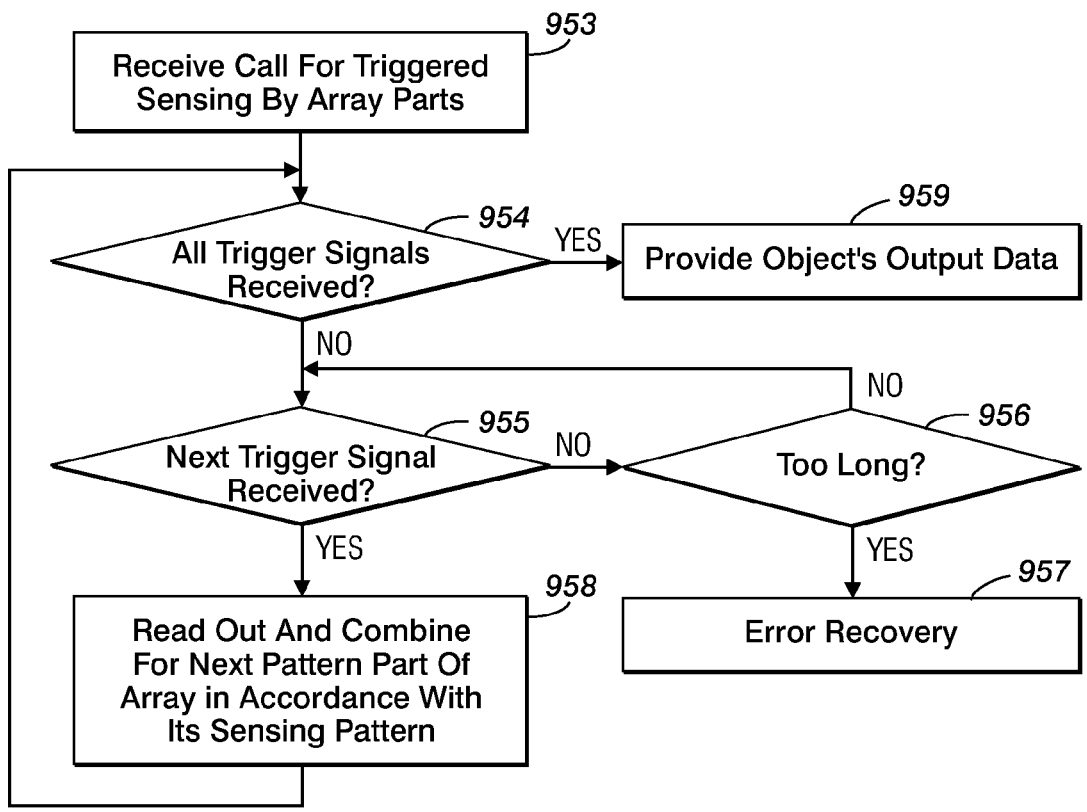
FIG. 25 is a flow chart showing readout operations in an implementation as in FIG. 24 with a photosensing array.

The flow chart in FIG. 25 illustrates how triggered sensing techniques similar to those in FIG. 24 could be implemented in an IC-implemented sensing element arrangement without separate trigger detector circuitry, such as with CPU 402 (FIG. 5) operating as control circuitry. In other words, an array of photosensing cells on the IC includes parts that operate as trigger detectors and other parts that operate as encoder/sensors. As noted above, trigger detection is not in general necessary for exemplary implementations described herein, and this is also true for CCD arrays, CMOS arrays, and other arrays of photosensing cells, but the technique illustrated in FIG. 25 employs trigger detection.

The technique of FIG. 25 illustratively reads out some parts of an array, i.e. "trigger parts", to obtain trigger signals that can be used to control readout operations for respective other parts of the same array, i.e. "pattern parts"; the pattern parts can implement respective sensing patterns. The technique of FIG. 25 could be implemented, for example, in an additional triggered sensing routine that could be executed by CPU 402, in the course of which appropriate calls to routine 442 could be made to perform readout and combine operations. Although suitable for CPU 402, operations in FIG. 25 could be implemented with a wide variety of different types of circuitry with or without a CPU, possibly including circuitry integrated on the same IC with an array that includes the trigger parts and the pattern parts.

In the operation in box 953, CPU 402 receives a call for triggered sensing by array parts. In flexible implementations, the call could specify or otherwise indicate which parts of the array are to serve as trigger parts and which parts are to serve as pattern parts; the call could similarly specify, for each pattern part, the respective sensing pattern, such as a periodic pattern with a given period or a random, chirp, or other appropriately specified non-periodic pattern. In response, the operation in box 953 can perform appropriate initialization and other preliminary operations, such as to set appropriate values indicating the first trigger and pattern parts on the array.

The operation in box 954 then begins an outer iterative loop that can continue until all trigger parts provide photosensed quantities indicating that the object has entered their respective trigger detection regions. Each outer iterative loop includes one or more iterations of an inner iterative loop, which begins with the operation in box 955 testing the next trigger part along the array to determine whether its photosensed quantities indicate detection of the object in its trigger detection region. If not, the operation in box 956 can use an appropriate time limit or other criterion to determine whether it has been too long for the object to be detected by the next trigger part, in which case the operation in box 957 can initiate appropriate error recovery operations (not shown). If it has not been too long, the operation in box 955 is again performed.

When the operation in box 955 determines that the next trigger part's photosensed quantities indicate detection of the object, the outer iterative loop continues to the operation in box 958. In box 958, CPU 402 can provide appropriate calls, e.g. to readout and combine routine 442 (FIG. 5), so that photosensed quantities from the next pattern part of the array are appropriately read out in accordance with its sensing pattern. The operation in box 958 might be implemented to use information from previous pattern parts of the same array to determine parameters of the sensing pattern, such as its time scale.

Finally, when all the trigger parts have provided appropriate trigger signals and all the pattern parts have been read out, the operation in box 959 provides the object's output data in any appropriate form. The output data could include characteristic data about the object's characteristics, type data about the object's type, sensing results data indicating one or more time-varying waveforms, excitation data indicating excitation characteristics, environmental data indicating environmental characteristics, or other data obtained from sensing results from the pattern parts.

The technique of FIG. 25 is similar to a trigger and gate mechanism that records portions of an object's emanation intensity that exceed a threshold magnitude, then applies a window function to this finite signal. A trigger and gate mechanism could be used where objects are sufficiently spaced that each object's time-varying signal can be isolated from those of preceding and following objects. After application of the window function, appropriate other operations could be performed, such as a Fourier transform to obtain a scaling factor for use in time-scaled comparison.

If two or more objects concurrently have relative motion into a trigger detection region relative to a trigger detector as in either of FIG. 24 or 25, a triggering technique as described above might blindly produce overlapping sensing results for the objects as if they were one object. To resolve this problem, a Fourier transform of sensing results can be analyzed to find subpeaks that have a high probability of resulting from periodic signals from multiple objects having relative motion at different speeds. Each subpeak's scaling factor can be obtained for use in time-scaled comparison, and correlation or other comparison can be performed with each scaling factor to obtain correlation results for each object. Even if an error is made, such as by identifying a spurious subpeak, the correlation results can be analyzed to determine whether a signal emanating from an object moving at the counterpart speed was sensed.

More generally, photosensing in accordance with sensing patterns as described above can be modified and extended in various ways to handle a variety of situations. Such situations can, for example, involve sensing multiple objects and sensing without correlation to rapidly obtain object position.

Figure 26:
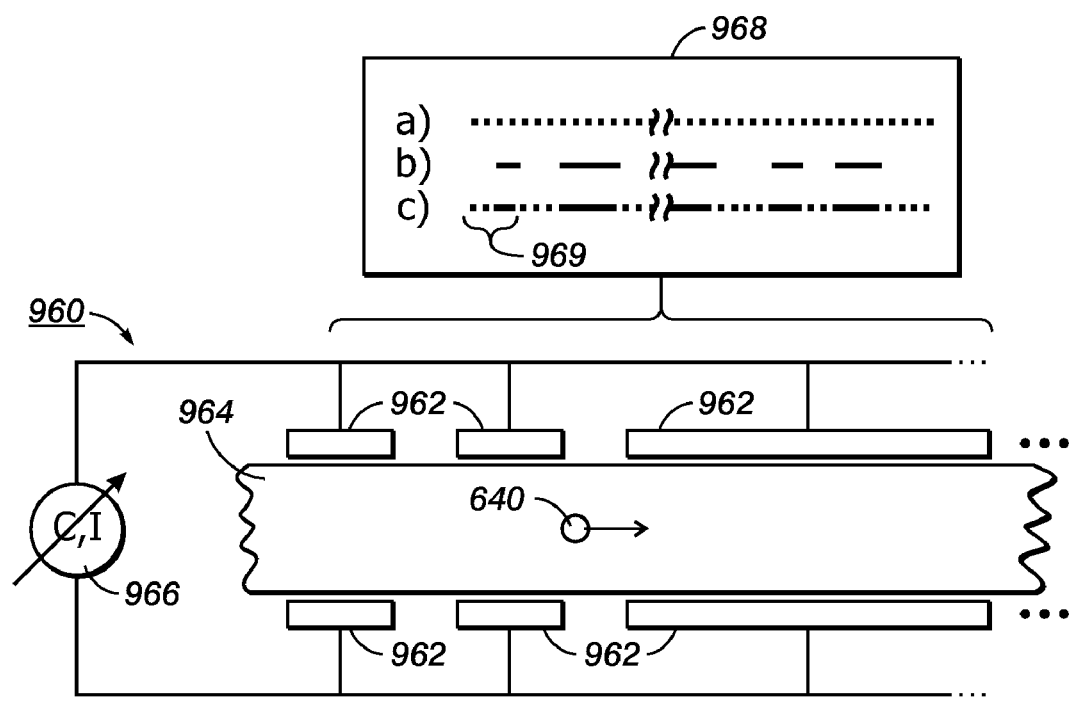
FIG. 26 is a partially schematic cross-sectional view of an encoding arrangement that includes an encoding/sensing component as in FIG. 2 with impedance-based sensing elements.

FIG. 26 shows an example of a non-optical impedance-based sensing pattern technique that can be used to obtain sensing results that indicate one or more time-varying waveforms. The technique illustrated in FIG. 26 is similar to a technique described in co-pending U.S. patent application Ser. No. 11/698,409, entitled "Method and System Implementing Spatially Modulated Excitation or Emission for Particle Characterization with Enhanced Sensitivity", incorporated herein by reference in its entirety. Impedance spectroscopy flow cytometry is further described in Cheung, K., Gawad, S., and Renaud, P., "Impedance Spectroscopy Flow Cytometry: On-Chip Label-Free Cell Differentiation", *Cytometry Part A*, Vol. 65A, 2005, pp. 124-132, also incorporated herein by reference.

Encoding/sensing component 960 in FIG. 26 includes an array of electrodes 962 along walls of channel 964, within which object 640 can have relative motion, such as by being carried by a fluid. Electrodes 962 are connected to measurement device 966, which could be implemented as described in the Cheung, et al. article cited above. As suggested, device 966 could record or provide a time dependent signal such as a measure of capacitance or current, or any other impedance-related electrical or magnetic characteristic that can vary between electrodes on opposite sides of channel 964 or that can be sensed by other similar impedance-based sensors on one or both sides of channel 964. As object 640 has relative motion through channel 964 between electrodes 962 on either side, in other words, device 966 obtains a sensed time-varying waveform indicating a characteristic of object 640.

Although capacitance and conductance are illustratively shown in FIG. 26, a wide variety of different electrical and/or magnetic characteristics could be measured, providing information about a variety of characteristics such as, for a biological cell, cell size, membrane capacity, cytoplasm conductivity, cytoplasm permittivity, and so forth. In particular, electrodes 772 could be replaced with an implementation of Hall effect sensors in a similar pattern to provide impedance-based sensing of magnetic characteristics. Furthermore, device 966 can provide an electrical wobble frequency to electrodes 962 to determine frequency at which a given characteristic is measured by encoding the time-varying waveform.

Electrodes 962 form a pattern that can be understood from the binary signals in box 968. The upper signal, labeled "a)", is a simple periodic binary signal; the middle signal, labeled "b)", is a random binary signal, with varying ON and OFF durations; and the lower signal, labeled "c)" can be obtained by logically combining signals like a) and b) in an alignment similar to that shown—in the illustrated example, the logical combination is an OR operation, so that a given point of signal c) is ON (black) when one or both of the aligned points of a) and b) is ON, but is OFF (white) whenever neither of the aligned points of a) and b) is ON. The positions and lengths of electrodes 962 are proportional to the lengths of ON segments of the binary signal c), and therefore concurrently encode the sensed time-varying wave form both periodically according to signal a) and randomly according to signal b); the proportionality of ON segments of c) with electrodes 962 can be seen by comparing lengths of the first three ON segments of signal c), reference number 969, with lengths of the three upper electrodes 962. As a result of the concurrent encoding described above, information can be extracted from the sensed time-varying waveform, such as about position, speed, and other characteristics of object 640.

The arrangement of electrodes 962 in FIG. 26 is merely illustrative, and could be varied in many ways. For example, electrodes 962 could form a similar pattern along only one side of channel 964 with no electrodes on the other side or with a single, large unpatterned electrode on the other side. Similarly, rather than only being opposite each other, electrodes could be positioned around a channel. Furthermore, different materials could be used for different electrodes and electrodes could be spaced at different distances from the walls of channel 964 in order to obtain more complicated patterns and therefore encode additional information. In general, electrodes 962 could be implemented in various ways, including as a non-periodic arrangement of structured electrodes. Also, simpler binary signals as in box 968 could be combined in any appropriate logical combination other than the OR combination, as appropriate in a given application.

The general technique illustrated in FIG. 26 could also be applied in other contexts. For example, a superposition sensing pattern as illustrated in box 968 could be implemented with Hall effect sensors along one side of channel 964 or in other appropriate arrangements on both sides or around channel 964; also, the pattern could be implemented with photosensing elements in ways described above, such as with discrete photosensing elements with extents as shown or a filter arrangement having a similar pattern. An implementation with an arrangement of magnetic sensors, such as structured or patterned Hall effect sensors, could, for example, obtain time-dependent sensing results that indicate time variation in response to magnetic particle or objects such as magnetic beads that have relative motion within a respective encoding/sensing region, whether with beads passing by the arrangement or with immobilized beads that the arrangement moves past. It should be noted, however, that impedance-based sensing elements generally do not perform remote sensing effectively in the way photosensors, acoustic sensors, and certain other types of signal sensors can, so that constraints on positioning are greater for impedance-based sensing elements.

Some techniques as described above have been successfully applied to simulated time-varying waveforms. In particular, time scaling techniques have been found to improve S/N ratio of a simulated observed signal that contains both an encoding based on a template and also additive noise, and where the observed signal has an unknown time scaling that occurs before it is observed; S/N ratio of 0.5 has been obtained and 0.1 appears achievable. These results could be obtained with particle speeds up to 0.5 m/sec and higher speeds up to a few m/sec appear to be feasible, with particles having effective sizes down to 0.6 μm, and with particle separations down to a given implementation's MFS. A demonstration included counting CD4 in a whole blood sample; single tag detection was shown to be feasible.

Implementations as described above in relation to FIGS. 1-26 could be advantageously applied in a wide variety of sensing applications, possibly including, for example, fluorescence- or impedance-based flow cytometry or other biodetector applications that seek a signature of a particle of unknown velocity; such biodetectors often use microfluidic channels with inhomogeneous flow profiles, causing variation in particle velocity. The techniques can be used to count or obtain ratios between fluorescing objects of different types, such as different types of tagged cells, particles, tagged DNA, and so forth. In such an application, calibration can be performed using known objects, e.g. tagged beads, with known velocities to obtain template waveforms that include deviations caused by fabrication tolerances but can then be compared with sensed waveforms to obtain information about unknown objects. To improve S/N, known and sensed waveforms can be correlated, such as after time scaling of each known waveform. If a sensed waveform includes or is accompanied by periodic modulation, a periodicity value such as a frequency can be used to obtain a scaling factor for time scaling before correlation, allowing more rapid correlation than if a brute force technique is used to find a satisfactory time scaling.

Implementations described above may be advantageous in biodetector applications that require compact, low-cost components without critical optics and with high sensing efficiency. Such applications might include point-of-care flow cytometry (such as with an integrated flow cytometer), DNA analysis, proteomics, and so forth.

Also, implementations described above could be applied in scanning of bio-chips or documents where objects have different emanation spectra, and so forth. The techniques may also be applicable in various low S/N ratio systems in which a known signal is bounced off an object having relative motion at an unknown velocity, such as where object velocity is on the order of signal propagation velocity, as in SONAR. The techniques may be especially advantageous where precise information about position, speed, or type of objects is sought.

Implementations described above might also be useful in obtaining information about characteristics of environment (e.g. substances in water, blood, or other fluid) or of excitation. Possible characteristics of water, for example, might include turbidity or color, which might be measurable from scattering of emanating light. Calibration could be performed with a known fluid that carries beads with known characteristics through an encoding/sensing region; then the same beads could be carried through the encoding/sensing region by an unknown but homogeneous fluid that is being analyzed. Absorption or other characteristics of the unknown fluid could change measurements of the beads' characteristics, such as their fluorescence or scattering spectra. Information might also be obtained from a speed profile of the unknown fluid. If a certain constituent (e.g. a protein) is present in the unknown fluid and if the beads are functionalized to interact with that constituent, the constituent could affect emanating light characteristics by interacting with the beads, e.g. switching fluorescence on or off, changing intensity, or even changing color of emanating light.

Some of the implementations described in relation to FIGS. 1-26 are examples of an article that includes an encoding/sensing component and a relative motion component. The encoding/sensing component includes sensing elements and obtains sensing results from objects in a respective encoding/sensing region relative to the encoding/sensing component. The relative motion component causes respective relative motion of each of a subset of the objects, and each has respective relative motion within the encoding/sensing region. In response to the relative motion within the encoding/sensing region, the sensing results indicate one or more time-varying waveforms. The encoding/sensing component includes a non-periodic arrangement of sensing elements, a longitudinal sequence of sensing elements, and/or one or more IC-implemented sensing elements. The sensing elements in the non-periodic arrangement perform photosensing or impedance-based sensing and obtain sensing results that indicate a non-periodic time-varying waveform with time variation in accordance with the non-periodic arrangement. The longitudinal sequence has a combined sensing pattern that is approximately equal to a superposition or scaled superposition of a set of simpler sensing patterns; its sensing elements perform photosensing or impedance-based sensing and obtain sensing results indicating a superposition time-varying waveform with time variation in accordance with all of the simpler sensing patterns. Each IC-implemented sensing element includes one or more arrays, each on a respective IC, and each including photosensing cells; the IC-implemented sensing element also includes readout/combined circuitry that reads out photosensed quantities from a set of the photosensing cells in groups in accordance with one or more cell-group sensing patterns and combines the readout photosensed quantities to obtain sensing results indicating one or more time-varying waveforms with time variation in accordance with the cell-group sensing patterns.

In specific implementations, the article can also include a fluidic structure that includes a channel through which objects travel during operation. If an impedance-based sensor, the sensing elements can be electrodes in a pattern that is approximately equal to a superposition or scaled superposition of a periodic pattern and a non-periodic pattern. If a non-periodic arrangement, it can be a random pattern or a chirp pattern. In the longitudinal sequence or in the set of simpler sensing patterns, each pattern can be a periodic pattern, a random pattern, or a chirp pattern, and the set can include combinations. Also, the patterns in the set can be positioned so that their respective variation directions are at least approximately parallel, and each can be a one-dimensional pattern.

In specific implementations with IC-implemented sensing elements, each array can have CCD-type readout circuitry or CMOS-type readout circuitry; the readout/combined circuitry can include circuitry on an IC with at least one of the arrays, circuitry external to ICs that include arrays, and/or a programmed CPU. An IC-implemented sensing element can also include a filter arrangement with the array's cell size range and the filter arrangement's feature size range being sufficiently separated that light passing through a sequence of filter arrangement features reaches a cell of the array or light passing through a feature reaches a combination of cells of the array; in the first case, the cell's photosensed quantities can be read out to obtain sensing results that indicate a time-varying waveform in accordance with the sequence of filter features, but in the second case, the combination of cells can be read out in a sensing pattern and combined to produce sensing results that indicate a time-varying waveform in accordance with the sensing pattern.

In further specific implementations, more generally, sensing elements can have different respective extents. Also, the encoding/sensing component can have a minimum feature size approximately as large as or larger than the largest of the respective interaction cones of the objects.

In further specific implementations with photosensing elements, different photosensing elements can photosense in different respective subranges of photon energies. The encoding/sensing component can also include different filter arrangements that transmit light in the different photon energy subranges. Also, different photosensing elements can have different ratios between photosensed quantity and received light intensity.

In further specific implementations, the encoding/sensing component can include a photosensing array IC with CMOS-type or CCD-type readout circuitry, an arrangement of discrete photosensors in the non-periodic arrangement and/or the longitudinal sequence, an arrangement of electrodes, a longitudinal sequence of sensing elements that vary in a random or chirped pattern, a longitudinal sequence of sensing elements with a combined sensing pattern that is approximately equal to a superposition or scaled superposition of simpler sensing patterns, sensing elements with different sensing areas, sensing elements that photosense different subranges of photon energies, sensing elements that photosense light received through a filter arrangement, sensing elements with different sensed intensity ratios, parallel sensing elements that extend lengthwise, and/or sensing elements on opposite sides of a fluidic channel. Each sensing element can bound a side of a channel, be on an outside surface of a part that bounds a channel, be spaced by a gap from an outside surface of such a part, or be positioned outside a channel so that an optical element provides light from the channel to it.

In further specific implementations, the article can be a flow cytometer, and the time-varying waveforms can include information about objects. Fluid carrying objects through a channel can include gas, liquid, and/or aerosol. The article can also include a processing component that obtains data indicating information about speed of objects, position of objects, characteristics of objects, types of objects, characteristics of excitation, and/or characteristics of environment.

Some of the implementations described above in relation to FIGS. 1-26 are examples of a method of using encoder/sensors that include sensing elements. The method operates an encoder/sensor to obtain sensing results from an object that has relative motion within an encoding/sensing region. The sensing results indicate time-varying waveforms that depend on the object's relative motion. The method can obtain sensing results that indicate a non-periodic time-varying waveform or a superposition time-varying waveform, or can read out photosensed quantities from a set of photosensing cells in groups in accordance with cell-group sensing patterns. The non-periodic time-varying waveform can at least approximate a time-varying waveform indicated by sensing results from a non-periodic arrangements of sensing elements; similarly, the superposition time-varying waveform can at least approximate a time-varying waveform that would be indicated by sensing results from a longitudinal sequence of sensing elements as described above. With readout photosensed quantities, the method can combine the quantities to obtain sensing results indicating one or more time-varying waveforms in accordance with the cell-group sensing patterns.

In specific implementations, the non-periodic waveform and the superposition time-varying waveform can be the same waveform. In general, the non-periodic time-varying waveform could be one of the types described above, and the simpler sensing patterns could include any of the pattern types described above.

In further specific implementations that include photosensing cells, the method could read out and combine photosensed quantities by reading out groups in accordance with a periodic sensing pattern, reading out groups in accordance with a non-periodic sensing pattern, reading out groups in accordance with a combined sensing pattern that is approximately equal to a superposition or scaled superposition, reading groups in accordance with complementary sensing patterns, obtaining sensing results indicating the non-periodic time-varying waveform, and/or obtaining sensing results that indicate the superposition time-varying waveform. The arrays could be CCD arrays with cells in each line capable of being read out by shifting, and, for each group, the method could shift a respective set of lines to read out photosensed quantities and could bin the quantities to obtain a binned photosensed quantity for the group, then time ordering the binned photosensed quantities for a sequence.

Some of the implementations described above in relation to FIGS. 1-26 are examples of an encoder/sensor that includes a longitudinal sequence of sensing elements as described above. In specific implementations, the encoder/sensor can be an impedance-based sensor and the longitudinal sequence can be a sequence of electrodes, with the combined sensing pattern approximately equal to a superposition or scaled superposition of a periodic pattern and a non-periodic pattern.

Some of the implementations described above in relation to FIGS. 1-26 are examples of a system that includes a sensing element arrangement and a processing component. The sensing element arrangement includes a non-periodic arrangement, a longitudinal sequence, and/or one or more IC-implemented sensing elements as described above. The processing component receives the sensing results and, in response, provides data indicating the information resulting from the respective relative motion of at least one object.

In specific implementations, in addition to other features described above, the processing component can provide signals causing the sensing element arrangement to produce the sensing results. For example, the processing component can provide signals that cause shifting of lines of CCD arrays as described above. The processing component can be programmed to perform a comparing operation on a set of time-varying waveforms to obtain comparison results, and can use the comparison results to obtain data indicating a spectral difference between time-varying waveforms.

Exemplary implementations described above employ photosensors or impedance-based sensors with specific features, but a wide variety of sensors could be used to obtain sensing results indicating values of various parameters other than emanating light intensity, parameters that can have time variation that indicates information such as about objects having relative motion within encoding/sensing regions relative to the sensors. Similarly, implementations described above involve sensing information in response to objects that are moving in fluidic channels or that are moving relative to a sensor such as in scanning, but various other types of fluidic implementations or other implementations in which objects move in various other ways could be sensed to obtain sensing results as in techniques described above.

Implementations as described above could be implemented together with triggering and other object detection techniques described in co-pending U.S. patent application Ser. No. 12/337,771, entitled "Obtaining Sensing Results and/or Data in Response to Object Detection", incorporated herein by reference in its entirety. Similarly, implementations as described above could be implemented together with relative motion techniques described in co-pending U.S. patent application Ser. No. /12/337,796, entitled "Causing Relative Motion", incorporated herein by reference in its entirety.

Components of exemplary implementations as described above could have various shapes, dimensions, or other numerical or qualitative characteristics other than those illustrated and described above. Similarly, although the exemplary implementations generally involve sensing from a single fluidic channel, implementations could readily include multiple parallel channels, allowing parallel sensing and readout and larger scale sensing.

Some of the above exemplary implementations involve specific types of encoding/sensing components, fluidic components, filter components, displacement control components, sensors, and so forth, but the invention could be implemented with a wide variety of other types of components. For example, some implementations use specific types of spatial modulation based on one or more of a sensing pattern, a filter assembly, trigger detector circuitry, and/or displacement control, but various other types of spatial modulation could be used, including any appropriate combination of color, gray scale, and black and white patterning and including other patterning techniques. Also, some exemplary implementations use specific types of processing, such as digital signals obtained after converting sensed analog values. In general, however, the invention could be implemented with any suitable signal processing techniques, including any appropriate combination of analog and digital processing; photosensed quantities could be combined either in analog or digital form; either or both of two compared waveforms could be obtained in analog or digital form; and any combination of time scaling could be performed before comparison. Further, some exemplary implementations use discrete, large area photosensors or impedance-based sensors, but various ICs with photosensing arrays might be used.

Some of the above exemplary implementations involve specific types of emanating light, e.g. fluorescence, and specific types of filtering and photosensing suitable to fluorescent light, but these are merely exemplary. The invention could be implemented in relation to various other types of emanating light with various other types of filtering and photosensing.

Some of the above exemplary implementations involve specific materials, such as in fluidic structures with light-transmissive components or in filtering arrangements with reflective material or light blocking material such as amorphous silicon, but the invention could be implemented with a wide variety of materials and with layered structures with various combinations of sublayers. Thicknesses of layers may vary across any suitable range.

The exemplary implementation in FIG. 5 employs a CPU, which could be a microprocessor or any other appropriate component. Furthermore, as noted above, operations could be performed digitally or with analog signals, and could be done either on the same IC as a photosensor array, on other components, or on a combination of the two, with any appropriate combination of software or hardware.

The above exemplary implementations generally involve use of encoding/sensing components, sensing element arrangements, sensors, photosensors, filter arrangements, displacement control arrangements, and so forth following particular operations, but different operations could be performed, the order of the operations could be modified, and additional operations could be added within the scope of the invention. For example, readout of sensed quantities from a sensor to obtain a sensed time-varying waveform could be performed serially or in parallel, and, with an array, could be performed cell-by-cell, line-by-line, or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. An article comprising:
   an encoding/sensing component that includes one or more sensing elements, the encoding/sensing component obtaining sensing results from objects in a respective encoding/sensing region relative to the encoding/sensing component; and
   a relative motion component that, in operation, causes respective relative motion of each of a subset of the objects; each of the objects in the subset having respective relative motion within the encoding/sensing region; in response to the respective relative motion of an object in the subset within the encoding/sensing region, the sensing results indicating one or more time-varying waveforms;
   the encoding/sensing component including at least one of:
      a non-periodic arrangement of sensing elements that, in operation, perform photosensing or impedance-based sensing and obtain sensing results that indicate a non-periodic time-varying waveform with time variation in accordance with the non-periodic arrangement;
      a longitudinal sequence of sensing elements, the longitudinal sequence having a combined sensing pattern that is approximately equal to a superposition or scaled superposition of a set of two or more simpler sensing patterns so that the sensing elements in the longitudinal sequence, in operation, perform photosensing or impedance-based sensing and obtain sensing results that indicate a superposition time-varying waveform with time variation in accordance with all of the simpler sensing patterns in the set; and
      one or more IC-implemented sensing elements, each IC-implemented sensing element including:
         one or more arrays, each on a respective IC; each array including photosensing cells; and
         readout/combine circuitry that reads out photosensed quantities from a set of the photosensing cells in groups in accordance with one or more cell-group sensing patterns and combines the readout photosensed quantities to obtain sensing results indicating one or more time-varying waveforms with time variation in accordance with the cell-group sensing patterns.

2. The article of claim 1 in which the objects emanate light, each sensing element being a photosensor.

3. The article of claim 1 in which the encoding/sensing component includes the non-periodic arrangement of sensing elements, the non-periodic arrangement including at least one of:
   a random pattern; and
   a chirp pattern.

4. The article of claim 1 in which the encoding/sensing component includes the IC-implemented sensing elements, each array being one of:
   an array with CCO-type readout circuitry; and
   an array with CMOS-type readout circuitry; the readout/combine circuitry including at least one of:
   circuitry on an IC that includes at least one of the arrays;
   circuitry external to ICs that include the arrays; and
   a programmed CPU.

5. The article of claim 1 in which the encoding/sensing component includes the IC-implemented sensing elements; one of the IC-implemented sensing elements further including:
   a filter arrangement through which light emanating from objects within the encoding/sensing region passes before reaching one of the arrays in the sensing element;
   the array having a cell size range and the filter arrangement having a feature size range; the cell size range and the feature size range being sufficiently separated that one of:
      light emanating from an object passes through a sequence of features of the filter arrangement before reaching a cell of the array and the cell's photosensed quantities are read out to obtain sensing results that indicate a time-varying waveform in accordance with the sequence of filter arrangement features; and
      light emanating from an object passes through a feature of the filter arrangement before reaching a combination of cells of the array and the combination of cells are read out in a sensing pattern and combined to produce sensing results that indicate a time-varying waveform in accordance with the sensing pattern.

6. The article of claim 1 in which light within a range of photon energies emanates objects within the encoding/sensing region; the encoding/sensing component including first and second photosensing elements; each of the first and second photosensing elements photosensing emanating light in a respective subrange of the range of photon energies, the respective subranges being different; the encoding/sensing component further including:

first and second filter arrangements, the first and second photosensing elements receiving emanating light through the first and second filter arrangements, respectively; light in the first photosensing element's respective subrange being transmitted by the first filter arrangement and light in the second photosensing element's respective subrange being transmitted by the second filter arrangement.

7. The article of claim 1 in which the encoding/sensing component includes at least one of:

an IC that includes a photosensing array with CMOS-type readout circuitry;
an IC that includes a photosensing array with CCO-type readout circuitry;
an arrangement of discrete photosensors in at least one of the non-periodic arrangement and the longitudinal sequence;
an arrangement of electrodes;
a longitudinal sequence of sensing elements that vary in a random or chirped pattern;
a longitudinal sequence of sensing elements with a combined sensing pattern that is approximately equal to a superposition or scaled superposition of two simpler sensing patterns;
sensing elements with different sensing areas;
sensing elements that photosense different subranges of a range of photon energies;
sensing elements that photosense light emanating from the channel and received by the sensing elements through a filter arrangement;
sensing elements with different sensed intensity ratios;
two or more parallel, lengthwise-extending sensing elements; and
sensing elements on opposite sides of a fluidic channel.

8. The article of claim 1 in which the article is a flow cytometer, the one or more time-varying waveforms having time variation that includes information about the objects.

9. The article of claim 1, further comprising:

a processing component that, in response to the sensing results, performs operations to obtain data indicating information about at least one of:
speed of objects;
position of objects;
characteristics of objects;
types of objects;
characteristics of excitation; and
characteristics of environment.

10. A method of using encoder/sensors that include sensing elements, the method comprising:

operating an encoder/sensor that includes one or more sensing elements to obtain sensing results from an object that has relative motion within an encoding/sensing region relative to the encoder/sensor; the sensing elements performing at least one of photosensing and impedance-based sensing; the sensing results indicating one or more time-varying waveforms that depend on the object's relative motion; the act of operating the encoder/sensor including at least one of:
obtaining sensing results that indicate a non-periodic time-varying waveform, the non-periodic time-varying waveform at least approximating a time-varying waveform that would be indicated by sensing results from a non-periodic arrangement of sensing elements;
obtaining sensing results that indicate a superposition time-varying waveform, the superposition time-varying waveform at least approximating a time-varying waveform that would be indicated by sensing results from a longitudinal sequence of sensing elements, the longitudinal sequence having a combined sensing pattern that is approximately equal to a superposition or scaled superposition of a set of two or more simpler sensing patterns so that the longitudinal sequence would provide sensing results that indicate a waveform with time variation in accordance with all of the simpler sensing patterns in the set; and
with one or more arrays that include photosensing cells in the encoder/sensor, each array being on a respective IC, reading out photosensed quantities from a set of the photosensing cells in groups in accordance with one or more cell-group sensing patterns and combining the readout photosensed quantities to obtain sensing results indicating one or more time-varying waveforms in accordance with the cell-group sensing patterns.

11. The method of claim 10 in which the act of operating the encoder/sensor includes both the act of obtaining sensing results that indicate the non-periodic time-varying waveform and the act of obtaining sensing results that indicate the superposition time-varying waveform; the non-periodic waveform and the superposition time-varying waveform being the same waveform.

12. The method of claim 10 in which the object emanates light during its relative motion within the encoding/sensing region, the act of operating the encoder/sensor further comprising:

operating the sensing elements to photosense emanating light and using photosensed quantities from the sensing elements to obtain the sensing results.

13. The method of claim 12 in which the sensing elements include the photosensing cells that are included in the one or more arrays; the act of reading out photosensed quantities and combining the readout photosensed quantities comprising at least one of:

reading out groups in accordance with a periodic sensing pattern;
reading out groups in accordance with a non-periodic sensing pattern;
reading out groups in accordance with the combined sensing pattern that is approximately equal to a superposition or scaled superposition of a set of two or more simpler sensing patterns;
reading out groups in accordance with first and second sensing patterns that are complementary to each other;
obtaining sensing results that indicate the non-periodic time-varying waveform; and obtaining sensing results that indicate the superposition time-varying waveform.

14. The method of claim 13 in which the arrays are CCD arrays that include lines of cells, with photosensed quantities from photosensing cells in each line capable of being read out by shifting the line; the act of reading out photosensed quantities and combining the readout photosensed quantities comprising:

for each group, shifting a respective set of the lines to read out photosensed quantities of photosensing cells and binning the readout photosensed quantities of the lines in the group's respective set to obtain a binned photosensed quantity for the group; and
time ordering the binned photosensed quantities for at least one sequence of the groups.

15. The method of claim 10 in which in which the act of operating the encoder/sensor includes the act of obtaining sensing results that indicate the non-periodic time-varying waveform, the non-periodic time-varying waveform being one of:

a random time-varying waveform;
a chirp time-varying waveform; and
a superposition time-varying waveform with time variation in accordance with a superposition or scaled superposition of a set of two or more sensing patterns.

16. The method of claim 10 in which in which the act of operating the encoder/sensor includes the act of obtaining sensing results that indicate the superposition time-varying waveform, the set of two or more simpler sensing patterns including at least one of:
a periodic sensing pattern;
a spectrally-dependent sensing pattern;
an intensity-dependent sensing pattern;
a random sensing pattern; and
a chirp sensing pattern.

17. An encoder/sensor that obtains sensing results from objects in an encoding/sensing region relative to the encoder/sensor, the encoder/sensor comprising:
a longitudinal sequence of sensing elements, the longitudinal sequence having a combined sensing pattern that is approximately equal to a superposition or scaled superposition of a set of two or more simpler sensing patterns so that the longitudinal sequence can perform photosensing or impedance-based sensing and obtain sensing results from objects in the encoding/sensing region in accordance with all of the simpler sensing patterns in the set; and the combined sensing pattern being approximately equal to a superposition or scaled superposition of a periodic pattern and a non-periodic pattern.

18. The encoder/sensor of claim 17 in which the encoder/sensor is an impedance-based sensor and the longitudinal sequence is a sequence of electrodes.

19. The encoder/sensor of claim 17 in which the set of two or more simpler sensing patterns includes at least one of:
one or more periodic patterns;
one or more random patterns;
one or more chirp patterns;
one or more periodic patterns and one or more non-periodic patterns; and
two or more non-periodic patterns.

20. The encoder/sensor of claim 19 in which each of the patterns in the set of two or more simpler sensing patterns is one of:
a periodic pattern;
a random pattern; and
a chirp pattern.

21. A system comprising:
a sensing element arrangement that obtains sensing results from objects in a respective sensing region relative to the sensing element arrangement; each of a subset of the objects having respective relative motion within the sensing region; in response to the respective relative motion of an object in the subset within the sensing region, the sensing results indicating one or more sensed time-varying waveforms; and
a processing component that receives the sensing results and, in response, provides data indicating the information resulting from the respective relative motion of at least one object in the subset;
the sensing element arrangement including at least one of:
a non-periodic arrangement of sensing elements that, in operation, perform photosensing or impedance-based sensing and obtain sensing results that indicate a non-periodic sensed time-varying waveform;
a longitudinal sequence of sensing elements that, in operation, perform photosensing or impedance-based sensing, the longitudinal sequence having a combined sensing pattern that is approximately equal to a superposition or scaled superposition of a set of two or more simpler sensing patterns so that the sensing elements in the longitudinal sequence, in operation, obtain sensing results that indicate a sensed waveform with time variation in accordance with all of the simpler sensing patterns in the set; and
one or more IC-implemented sensing elements, each including:
one or more arrays, each on a respective IC; each array including photosensing cells; and
readout/combine circuitry that reads out photosensed quantities from a set of the photosensing cells in groups in accordance with one or more cell-group sensing patterns and combines the readout photosensed quantities to obtain sensing results indicating one or more sensed time-varying waveforms with time variation in accordance with the cell-group sensing patterns.

22. The system of claim 21 in which the sensing element arrangement includes the IC-implemented sensing elements, each array being one of:
a CCO array; and
a CMOS array.

23. The system of claim 22 in which the arrays include one or more CCO arrays, each including lines of cells, with photosensed quantities of photosensing cells in each line capable of being read out by shifting the line;
the processing component, in operation: for each group, providing signals that cause shifting of a respective set of the lines to read out photosensed quantities of photosensing cells and binning of the readout photosensed quantities of the lines in the group's respective set to obtain a binned photosensed quantity for the group; and
time ordering the binned photosensed quantities for at least one sequence of the groups.

24. The system of claim 21 in which the processing component includes at least one of:
circuitry on an IC that includes at least one of the arrays;
circuitry external to ICs that include the arrays; and
a programmed CPU.

25. The system of claim 21 in which the processing component is programmed to:
perform a comparing operation on a set of time-varying waveforms to obtain comparison results, at least one of the set being a sensed time-varying waveform; and
use the comparison results to obtain data indicating at least one spectral difference between the time-varying waveforms in the set.

26. The system of claim 21 in which the objects are biological cells or viruses and the system is a flow cytometer.

* * * * *